US010011573B2

(12) United States Patent
Tcherkassov et al.

(10) Patent No.: US 10,011,573 B2
(45) Date of Patent: Jul. 3, 2018

(54) HUMAN ANDROGEN RECEPTOR DNA-BINDING DOMAIN (DBD) COMPOUNDS AS THERAPEUTICS AND METHODS FOR THEIR USE

(71) Applicant: The University of British Columbia, Vancouver (CA)

(72) Inventors: Artem Tcherkassov, Vancouver (CA); Paul Rennie, Richmond (CA); Fuqiang Ban, Markham (CA); Huifang Li, Vancouver (CA); Eric Joseph Jean LeBlanc, Vancouver (CA); Kush Dalal, Vancouver (CA); Anton V. Tverdokhlebov, Poltava (UA); Sergiy Babiy, Kyiv (UA); Evgeniia Bogomol, Kyiv (UA); Kateryna Dunayenko, Kyiv (UA)

(73) Assignee: The University of British Columbia, Vancouver (CA)

( * ) Notice: Subject to any disclaimer, the term of this patent is extended or adjusted under 35 U.S.C. 154(b) by 0 days.

(21) Appl. No.: 15/118,652

(22) PCT Filed: Feb. 13, 2015

(86) PCT No.: PCT/CA2015/000086
§ 371 (c)(1),
(2) Date: Aug. 12, 2016

(87) PCT Pub. No.: WO2015/120543
PCT Pub. Date: Aug. 20, 2015

(65) Prior Publication Data
US 2017/0183319 A1 Jun. 29, 2017

Related U.S. Application Data

(60) Provisional application No. 62/023,773, filed on Jul. 11, 2014, provisional application No. 61/940,275, filed on Feb. 14, 2014.

(51) Int. Cl.
C07D 417/04 (2006.01)
C07D 417/14 (2006.01)
C07D 413/04 (2006.01)
C07D 413/14 (2006.01)
A61K 31/422 (2006.01)
A61K 31/426 (2006.01)
A61K 31/427 (2006.01)
A61K 31/437 (2006.01)
A61K 31/4439 (2006.01)
A61P 35/00 (2006.01)
C07D 277/42 (2006.01)

(52) U.S. Cl.
CPC .......... C07D 277/42 (2013.01); A61K 31/422 (2013.01); A61K 31/426 (2013.01); A61K 31/427 (2013.01); A61K 31/437 (2013.01); A61K 31/4439 (2013.01); C07D 413/04 (2013.01); C07D 413/14 (2013.01); C07D 417/04 (2013.01); C07D 417/14 (2013.01)

(58) Field of Classification Search
CPC .. C07D 417/04; C07D 417/14; C07D 413/04; C07D 413/14; A61K 31/426; A61K 31/427; A61K 437/4439
USPC ...... 544/60, 111; 546/209; 514/227.5, 231.5, 514/317, 326
See application file for complete search history.

(56) References Cited

U.S. PATENT DOCUMENTS

| 7,384,966 B2 | 6/2008 | Stevens et al. |
| 8,445,507 B2 | 5/2013 | Jung et al. |
| 8,802,689 B2 | 8/2014 | Jung et al. |
| 2009/0131475 A1 | 5/2009 | Uesugi et al. |
| 2012/0004270 A1 | 1/2012 | Miller |
| 2014/0038984 A1 | 2/2014 | Uesugi et al. |

FOREIGN PATENT DOCUMENTS

| DE | 10 2007 040 243 A1 | 2/2009 |
| WO | 02/051821 A1 | 7/2002 |
| WO | 03/045930 A1 | 6/2003 |
| WO | 2005/000300 A1 | 1/2005 |
| WO | 2006/090167 A2 | 8/2006 |

(Continued)

OTHER PUBLICATIONS

Zhang et al., Expert Opin. Drug Discov. (2013) 8(2):191-218.*
Liao et al., Transl Androl Urol 2013;2(3):187-196.*
Narayanan et al. Cancers 2016, 8, 108, 1-17.*
Watson et al. Nat Rev Cancer. Dec. 2015; 15(12): 701-711.*
Cecil Textbook of Medicine, edited by Bennet, J.C., and Plum F., 20th edition,vol. 1, 1004-1010, 1996.*
Freshney et al.,Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*

(Continued)

Primary Examiner — Venkataraman Balasubramanian
(74) Attorney, Agent, or Firm — Christensen O'Connor Johnson Kindness PLLC

(57) ABSTRACT

A compound having the structure of Formula I, wherein A is a substituted or unsubstituted aryl or heteroaryl group, D is a substituted or unsubstituted 5- or 6-membered heteroaryl or heterocyclyl group and E is a substituted or unsubstituted aryl, heteroaryl, cycloalkyl or heterocyclyl group. The compounds are used for the treatment of androgen modulated indications including cancer (prostate, breast, ovarian, endometrial or bladder cancer), hair loss, acne, hirsutism, ovarian cysts, polycystic ovary disease, precocious puberty and age related macular degeneration. The use of the compounds for the manufacture of a medicament for modulating AR activity, a method of treatment using such compounds and a pharmaceutical composition and a commercial package comprising said compounds are also described.

16 Claims, 18 Drawing Sheets

(56) References Cited

FOREIGN PATENT DOCUMENTS

WO          2012/143599 A1     10/2012

OTHER PUBLICATIONS

Bhuva, H.A., et al., "Synthesis and Cytotoxic Activity of Some Novel Substituted 2-phenyl-1,3-benzothiazoles," Journal of Pharmacy Research 3(5):980-983, May 2010.

Chemical Abstracts Services, CAS Registry Numbers: Compounds having the structure of Formula I wherein D is isoxazolyl, Registry © 2015 ACS on STN, 9 pages.

Chemical Abstracts Services, CAS Registry Numbers: Compounds having the structure of Formula II, Registry © 2015 ACS on STN, 40 pages.

Chemical Abstracts Services, CAS Registry Numbers: Compounds having the structure of Formula I wherein D is 2,4-thiazolyl, Registry © 2015 ACS on STN, 36 pages.

Chemical Abstracts Services, CAS Registry Numbers: Compounds having the structure of Formula I wherein D is 2,5-thiazolyl, Registry © 2015 ACS on STN, 5 pages.

Chemical Abstracts Services, CAS Registry Numbers: Compounds having the structure of Formula I wherein D is 5-methyl-2-thiazolyl, Registry © 2015 ACS on STN, 10 pages.

Chemical Abstracts Services, CAS Registry Numbers: Compounds having the structure of Formula I wherein D is imidazolyl, Registry © 2015 ACS on STN, 4 pages.

Chemical Abstracts Services, CAS Registry Numbers: Compounds having the structure of Formula I wherein D is oxadiazolyl, Registry © 2015 ACS on STN, 1 page.

Chemical Abstracts Services, CAS Registry Numbers: Compounds having the structure of Formula I wherein D is pyrimidinyl, Registry © 2015 ACS on STN, 2 pages.

Chemical Abstracts Services, CAS Registry Numbers: Compounds having the structure of Formula I wherein D is thienyl, Registry © 2015 ACS on STN, 3 pages.

Dalal, K., et al., "Selectively Targeting the DNA-Binding Domain of the Androgen Receptor as a Prospective Therapy for Prostate Cancer," Journal of Biological Chemistry 289(38):26417-26429, Sep. 2014.

Goto, N., et al., "Identification of a Novel Compound That Suppresses Breast Cancer Invasiveness by Inhibiting Transforming Growth Factor-β Signaling via Estrogen Receptor α," Journal of Cancer 5(5):336-343, Mar. 2014.

Gupta, S.D., et al., "Synthesis, Cytotoxic Evaluation, In Silico Pharmacokinetic and QSAR Study of Some Benzothiazole Derivatives," International Journal of Pharmacy and Pharmaceutical Sciences 2(3):57-62, Jul. 2010.

Jiang, B., and X.-H. Gu, "Synthesis and Cytotoxicity Evaluation of Bis(indolyl)thiazole, Bis(indolyl)pyrazinone and Bis(indolyl)pyrazine: Analogues of Cytotoxic Marine Bis(indole) Alkaloid," Bioorganic & Medicinal Chemistry 8(2):363-371, Feb. 2000.

Li, H., et al. "Discovery of Small-Molecule Inhibitors Selectively Targeting the DNA-Binding Domain of the Human Androgen Receptor," Journal of Medicinal Chemistry 57(15):6458-6467, Aug. 2014.

Miayhoub, a.S., et al., "Optimization of the Aromatase Inhibitory Activities of Pyridylthiazole Analogues of Resveratrol," Bioorganic & Medicinal Chemistry 20(7):2427-2434, Apr. 2012.

Racanè, L., et al., "Synthesis and Antiproliferative Activity of Cyano and Amidino Substituted 2-Phenylbenzothiazoles," Monatshefte für Chemie 137(12):1571-1577, Dec. 2006.

Extended European Search Report dated Nov. 20, 2017, issued in corresponding European Application No. 15748487.4, filed Feb. 13, 2015, 66 pages.

Al-Azawe, S.S., "Synthesis of 2,5-Disubstituted Thiazoles and Their Reactions With Grignard Reagents," Journal of the Iraqi Chemical Society 13(1):1-13, 1988; and CAplus Accession No. 1991:61983 (6 pages).

Bahrin, L.G., et al., "4-Bromo-2-[5-methyl-2-(morpholin-4-yl)-1,3-thiazol-4-yl]phenol," Acta Crystallographics, Section E: Structure Reports Online 69(7):o1170, 2013, 7 pages; and CAplus Accession No. 2013:1057002 (2 pages).

Birsa, M.L., "Synthesis of Some New 4-(2'-hydroxyaryl)-5-methyl-2-(N, N-dialkylamino)-thiazoles," Analele Stiintitice ale Universitatii "Al. I. Cuza" din Iasi, Chimie 8(2):325-328, 2000; and CAplus Accession No. 2001:667947 (6 pages).

Brown, M.L., et al., "Discovery of Amide Replacements That Improve Activity and Metabolic Stability of a bis-Amide Smoothened Antagonist Hit," Bioorganic & Medicinal Chemistry Letters 21(18):5206-5209, Sep. 2011; and CAplus Accession No. 2011:1061049 (2 pages).

Calderòn-Ortiz, L.K., et al., "Hydroxythiazole-Based Fluorescent Probes for Fluoride Ion Detection," European Journal of Organic Chemistry 2012(13):2535-2541, May 2012; and CAplus Accession No. 2012:381796 (2 pages).

Chaudhari, D.T., et al., "Synthesis and Study of 4-(p-aminophenyl)Thiazoles for in vitro Antitubercular Activity and as Useful Chemotherapeutic Intermediates," Bulletin of Haffkine Institute 4(1):8-15, 1976; and CAplus Accession No. 1976:559962 (16 pages).

Corsaro, A., et al., "Trisubstituted Thiazoles by a 6π-Electrocyclization of Iminothiocarbonyl Ylides," Tetrahedron Letters 22(34):3305-3308, 1981; and CAplus Accession No. 1982:122675 (4 pages).

Demirayak, S., et al., "Synthesis of Some 4-Pyrrolylphenylthiazole Derivatives of Their Antimicrobial Activities," Acta Pharmaceutica Turcica 39(3):133-136, 1997; and CAplus Accession No. 1997:778913 (2 pages).

Eckert, K., et al., "Synthesis and Solvatochromic Properties of 5-dicyanovinyl- and 5-tricyanovinyl-Substituted 2-amino-thiazoles and 2-amino-thiophenes," Phosphorus, Sulfur and Silicon and the Related Elements 152:99-114, 1999; and CAplus Accession No. 1999:773614 (2 pages).

Fan, S., et al., "Copper-Catalyzed Dehydrogenative Cross-Coupling of Benzothiazoles With Thiazoles and Polyfluoroarene," Organic Letters 14(18):4950-4953, Sep. 2012; and CAplus Accession No. 2012:1352227 (2 pages).

Fink, B.E., et al., "Novel Structural Templates for Estrogen-Receptor Ligands and Prospects for Combinatorial Synthesis of Estrogens," Chemistry & Biology 6(4):205-219, Apr. 1999; and CAplus Accession No. 1999:327909 (2 pages).

Garcia, P., et al., "Easily Assembled, Modular N,O-Chelating Ligands for Ta(V) Complexation: A Comparative Study of Ligand Effects in Hydroaminoalkylation With N-methylaniline and 4-methoxy-N-methylaniline," Tetrahedron 69(27-28):5737-5743, Jul. 2013; and CAplus Accession No. 2013:747936 (2 pages).

Golubev, V., et al., "A Simple, Three-Component Synthesis of 2-Aminothiazoles Using Trimethylsilyl Isothiocyanate," Tetrahedron Letters 54(36):4844 4847, Sep. 2013; and CAplus Accession No. 2013:1135759 (2 pages).

Hatfield, J.M., et al., "Mono- and Trifluorination of the Thiazole Ring of 2,5-Diaryithiazoles Using N-fluorobenzenesulfonimide (NFSI)," Tetrahedron Letters 54(8):1025-1028, Feb. 2013; and CAplus Accession No. 2013:68847 (2 pages).

Kaspady, M., et al., "Synthesis, Antibacterial Activity of 2,4-Disubstituted Oxazoles and Thiazoles as Bioisosteres," Letters in Drug Design & Discovery 6(1):21-28, Jan. 2009; and CAplus Accession No. 2009:1018829 (4 pages).

Keil, D., and H. Hartmann, "Synthesis and Characterization of 1, 3-bis-(2-dialkylamino-5-thiazolyl)-Substituted Squaraines and Their 2-(dialkylamino)Thiazole Precursors," Liebigs Annalen 6:979-984, 1995; and CAplus Accession No. 1995:849155 (2 pages).

Kerdesky, F.A.J., et al., "4-Hydroxythiazole Inhibitors of 5-Lipoxygenase," Journal of Medicinal Chemistry 34(7):2158-2165, Jul. 1991; and CAplus Accession No. 1991:449482 (4 pages).

Kim, S.K., et al., "Synthesis of Trisubstituted Thiazoles by Ligand-Free Palladium-Catalyzed Direct 5-Arylation of 2,4-Disubstituted Thiazoles Under Conventional and Microwave-Assisted Heating," Tetrahedron 69(51):10990-10995, Dec. 2013; and CAplus Accession No. 2013:1783909 (2 pages).

(56) References Cited

OTHER PUBLICATIONS

Kulkarni, B.S., et al., "Chemotherapy of Tuberculosis. IX. Synthesis and Screening of New Thiazolyl Thiocarbanilides," Journal of Pharmaceutical Sciences 58(7):852-857, Jul. 1969; and CAplus Accession No. 1969:479422 (4 pages).
Li, H., et al., "Discovery of Small-Molecule Inhibitors Selectively Targeting the DNA-Binding Domain of the Human Androgen Receptor," Journal of Medicinal Chemistry 57(15):6458-6467, Aug. 2014.
Li, Z., et al., "Pd(II)-Catalyzed Direct C5-Arylation of Azole-4-Carboxylates Through Double C-H Bond Cleavage," Chemical Communications 48(31):3763-3765, Apr. 2012; and CAplus Accession No. 2012:411493 (2 pages).
Liu, X.-W., et al., "Regioselective Arylation of Thiazole Derivatives at 5-Position Via Pd Catalysis Under Ligand-Free Conditions," Organic Letters 15(22):5774-5777, Nov. 2013; and CAplus Accession No. 2013:1709680 (2 pages).
Lu, Y., et al., "Design, Synthesis, and SAR Studies of 4-Substituted Methoxylbenzoyl-Aryl-Thiazoles Analogues as Potent and Orally Bioavailable Anticancer Agents," Journal of Medicinal Chemistry 54(13):4678-4693, Jul. 2011; and CAplus Accession No. 2011:729990 (2 pages).
Mayhoub, A.S., et al., "Optimization of Thiazole Analogues of Resveratrol for Induction of NAD(P)H:Quinone Reductase 1 (QR1)," Bioorganic & Medicinal Chemistry 20(24):7030-7039, Dec. 2012; and CAplus Accession No. 2012:1666083 (8 pages).
Park, G., et al., "Pd Nanoparticle-Silica Nanotubes (Pd@SNTs) as an Efficient Catalyst for Suzuki-Miyaura Coupling and $sp^2$ C—H Arylation in Water," Green Chemistry 15(12):3468-3473, Dec. 2013; and CAplus Accession No. 2013:1802415 (6 pages).
Patel, A.D., and C.N. Patel, "Synthesis and Biological Evaluation of Substituted 4-phenyl-1,3-Thiazole Derivatives as Potential Anti-Inflammatory Agents," International Journal of Drug Development & Research 4(1):106-111, 2012; and CAplus Accession No. 2012:599253 (2 pages).
Patil, A.M., et al., "Synthesis and Study of 4-(3-amino-4-Methoxyphenyl) Thiazoles for in vitro Antituberculosis Activity and as Useful Chemotherapeutic Intermediates," Bulletin of Haffkine Institute 4(2):51-55, 1976; and CAplus Accession No. 1976:192613 (6 pages).
Pieroni, M., et al., "Design, Synthesis and Investigation on the Structure-Activity Relationships of N-Substituted 2-Aminothiazole Derivatives as Antitubercular Agents," European Journal of Medicinal Chemistry 72:26-34, Jan. 2014.
Pons, J.-F., et al., "Thiazole Formation Via Traceless Cleavage of Rink Resin," Tetrahedron Letters 41(25):4965-4968, Jun. 2000; and CAplus Accession No. 2000:443488 (1 page).
Rao, G.R., and K.S. Rao, "Synthesis and Anthelmintic Activity of 5(6)-[2-arylthiazol-4-yl)benzimidazole-2-Carbamates," Indian Journal of Pharmaceutical Sciences 50(6):349-351, 1988; and CAplus Accession No. 1989:470366 (2 pages).
Romagnoli, R., et al., "Microwave-Assisted Synthesis of Substituted 2,4-Diaryithiazoles and Their Evaluation as Anticancer Agents," Letters in Drug Design & Discovery 4(7):464-466, 2007; and CAplus Accession No. 2007:1220818 (4 pages).
Sanchez-Viesca, F., and R. Gomez, "Synthesis and Spectroscopic Study of New Diaryithiazoles," Revista de la Sociedad Quimica de Mexico 39(3):125-129, 1995; and CAplus Accession No. 1995:871461 (4 pages).
Sanchez-Viesca, F., et al., "/\1H NMR evidence of CO, C—N and Ch—C1 Hydrogen Bonds in New Thiazole Derivatives," Revista Latinoamericana de Quimica 28(2):72-78, 2000; and CAplus Accession No. 2000:879938 (2 pages).

Sanz-Cervera, J.F., et al., "Solution Versus Fluorous Versus Solid-Phase Synthesis of 2,5-Disubstituted 1,3-Azoles: Preliminary Antibacterial Activity Studies," Journal of Organic Chemistry 74(23):8988-8996, Dec. 2009; and CAplus Accession No. 2009:1380222 (6 pages).
Seliger, H., et al., "Synthesis of Some Aminated Thiazoles," Analele Stiintitice ale Universitatii "Al. I. Cuza" din Iasi, Chimie 5:123-128, 1997; and CAplus Accession No. 2000:28713 (4 pages).
Shelke, S.H., et al., "Synthesis and Antimicrobial Activities of Novel Series of 3-(4-(2-substituted thiazol-4-yl)phenyl)-2-(4-methyl-2-substituted thiazol-5-yl)thiazolidin-4-one Derivatives," Journal of Heterocyclic Chemistry 51(4):1151-1156, Jul. 2014.
Shendrik, O.H., et al., "Synthesis and Study of the Antioxidant Activity of 3',4'-dihydroxyphenyithiazoles," Zhumal Organichnoi ta Farmatsevtichnoi Khimii 9(4):61-64, 2011; and CAplus Accession No. 2012:256580 (2 pages).
Shukri, J., and A. Hassan, "New Thiazole Derivatives," Wissenschaftliche Zeitschrift—Martin-Luther-Universitaet Halle-Wittenberg, Mathematisch-Naturwissenschaftliche Reihe 33(3):81-85, 1984; and CAplus Accession No. 1984:630402 (4 pages).
Singh, H., et al., "N-Quaternary Heterocyclics. Part X. Add-Catalyzed Transformation of 2-(4-Quinazolinylthio)ketones to 2-[4-(3H)-Quinazolinylidene]Ketones and 2-(o-Aminophenyl) Thiazoles," Indian Journal of Chemistry, Section B: Organic Chemistry Including Medicinal Chemistry 20B(1):17-20, 1981; and CAplus Accession No. 1981:192268 (4 pages).
Taeuscher, E., et al., "Bis (4-Hydroxythiazoles): Novel Functional and Switchable Fluorophores," Synthesis 14(2011):2334-2339, Jul. 2011; and CAplus Accession No. 2011:1243461 (2 pages).
Tani, S., et al., "Programmed Synthesis of Arylthiazoles Through Sequential C—H Couplings," Chemical Science 5(1):123-135, 2014; and CAplus Accession No. 2013:1854631 (12 pages).
Teller, J., et al., "Substituted 2-Aminothiazoles From α-Thiocyanatoacetophenones and Dialkylamines," Journal fuer Praktische Chemie (Leipzig) 332(4):453-460, 1990; and CAplus Accession No. 1991:101814 (4 pages).
Turner, G.L., et al., "Direct Arylation of Thiazoles on Water," Angewandte Chemie, International Edition 46(42):7996-8000, Oct. 2007; and CAplus Accession No. 2007:1261660 (10 pages).
Uehara, T.N., et al., "Palladium-Catalyzed C—H and C—N Arylation of Aminothiazoles With Arylboronic Acids," Asian Journal of Organic Chemistry 2(11):938-942, Nov. 2013; and CAplus Accession No. 2013:1782463 (2 pages).
Varma, R.S., "Solvent-Free Synthesis of Heterocyclic Compounds Using Microwaves," Journal of Heterocyclic Chemistry 36(6):1565-1571, Nov.-Dec. 1999; and CAplus Accession No. 2000:93936 (4 pages).
Varma, R.S., et al., "Solid State Synthesis of 2-aroylbenzo[b]furans, 1,3-thiazoles and 3-aryl-5,6-dihydroimidazo[2,1-b][1,3]thiazoles From α-tosyloxyketones Using Microwave Irradiation," Journal of the Chemical Society, Perkin Transactions 1: Organic and Bio-Organic Chemistry 24:4093-4096, 1998; and CAplus Accession No. 1998:775997 (4 pages).
Wei, S., et al., "Convenient One-Pot Two-Step Synthesis of 1,3-Thiazoles Via Organocatalyzed Epoxidation of Nitroolefins," Synthesis 44(22):3441-3446, 2012; and CAplus Accession No. 2013:38081 (6 pages).
Xiao, J., et al., "Discovery, Synthesis, and Biological Evaluation of Novel SMN Protein Modulators," Journal of Medicinal Chemistry 54(18):6215-6233, Sep. 2011; and CAplus Accession No. 2011:1050786 (28 pages).
Zang, F., and M.F. Greaney, "Decarboxylative Cross-Coupling of Azoyl Carboxylic Acids With Aryl Halides," Organic Letters 12(21):4745-4747, Nov. 2010; and CAplus Accession No. 2010:1215397 (4 pages).
Zang, M.Q., et al., "Quinolone Antibacterials. 1. 7-(2-Substituted-4-thiazolyl and Thiazolicinyl)Quinolones," Journal of Heterocyclic Chemistry 28(3):673-683, Apr.-May 1991; and CAplus Accession No. 1991:471455 (2 pages).
Partial Supplementary European Search Report dated Aug. 9, 2017, issued in European Application No. 15748487.4, filed Feb. 13, 2015, 69 pages.

\* cited by examiner

A

AR transcription in LNCaP

B

PSA transcription in LNCaP (A)

(B)

HUMAN ANDROGEN RECEPTOR DNA-BINDING DOMAIN (DBD) COMPOUNDS AS THERAPEUTICS AND METHODS FOR THEIR USE

CROSS REFERENCE TO RELATED APPLICATIONS

This application claims the benefit of two U.S. Provisional Patent Applications Ser. No. 61/940,275 filed on 14 Feb. 2014 and 62/023,773 filed on 11 Jul. 2014 both entitled "HUMAN ANDROGEN RECEPTOR DIMER BINDING DOMAIN (DBD) COMPOUNDS AS THERAPEUTICS AND METHODS FOR THEIR USE".

TECHNICAL FIELD

This invention relates to therapeutic compounds and compositions, and methods for their use in the treatment of various indications, including various cancers. In particular the invention relates to therapies and methods of treatment for cancers such as prostate cancer.

BACKGROUND

Androgens are known to mediate their effects through the androgen receptor (AR). Androgens play a role in a wide range of developmental and physiological responses, for example, male sexual differentiation, maintenance of spermatogenesis, and male gonadotropin regulation (R. K. Ross, G. A. Coetzee, C. L. Pearce, J. K. Reichardt, P. Bretsky, L. N. Kolonel, B. E. Henderson, E. Lander, D. Altshuler & G. Daley, *Eur Ural* 35, 355-361 (1999); A. A. Thomson, *Reproduction* 121, 187-195 (2001); N. Tanji, K. Aoki & M. Yokoyama, Arch Androl 47, 1-7 (2001)). Also, androgens are associated with the development of prostate carcinogenesis. Induction of prostatic carcinogenesis in rodent models has been associated with androgens (R. L. Noble, *Cancer Res* 37, 1929-1933 (1977); R. L. Noble, *Oncology* 34, 138-141 (1977)) and men receiving androgens in the form of anabolic steroids are reported to have a higher incidence of prostate cancer (J. T. Roberts & D. M. Essenhigh, *Lancet* 2, 742 (1986); J. A. Jackson, J. Waxman & A. M. Spiekerman, *Arch Intern Med* 149, 2365-2366 (1989); P. D. Guinan, W. Sadoughi, H. Alsheik, R. J. Ablin, D. Alrenga & I. M. Bush, *Am J Surg* 131, 599-600 (1976)). Furthermore, prostate cancer does not develop if humans or dogs are castrated before puberty (J. D. Wilson & C. Roehrborn, *J Clin Endocrinol Metab* 84, 4324-4331 (1999); G. Wilding, *Cancer SUM* 14, 113-130 (1992)). Castration of adult males causes involution of the prostate and apoptosis of prostatic epithelium (E. M. Bruckheimer & N. Kyprianou, *Cell Tissue Res* 301, 153-162 (2000); J. T. Isaacs, *Prostate* 5, 545-557 (1984)). This dependency on androgens provides the underlying rationale for treating prostate cancer with chemical or surgical castration (i.e. androgen ablation).

Prostate cancer is the second leading cause of male cancer-related death in Western countries (Damber, J. E. and Aus, G. Lancet (2008) 371:1710-1721). Numerous studies have shown that the androgen receptor (AR) is central not only to the development of prostate cancer, but also the progression of the disease to the castration resistance state (Taplin, M. E. et al. J. Clin. Oncol. (2003) 21:2673-8; and Tilley, W. D. et al. Cancer Res. (1994) 54:4096-4102). Thus, effective inhibition of human AR remains one of the most effective therapeutic approaches to the treatment of advanced, metastatic prostate cancer.

The AR possesses a modular organization characteristic of all nuclear receptors. It is comprised of an N-terminal domain (NTD), a central DNA binding domain (DBD), a short hinge region, and C-terminal domain that contains a hormone ligand binding pocket (the ligand binding domain, which also comprises the hormone binding site (HBS)) and the Activation Function-2 (AF2) site (Gao, W. Q. et al. Chem. Rev. (2005) 105:3352-3370). The latter represents a hydrophobic groove on the AR surface which is flanked with regions of positive and negative charges—"charge clamps" that are significant for binding AR activation factors (Zhou, X. E. et al. J. Biol. Chem. (2010) 285:9161-9171). Recent studies have identified a novel site on the AR called Binding Function 3 (BF3) that is involved into AR transcriptional activity. When the AR translocates into the nucleus, the DBD dimerizes and binds to androgen response elements (AREs), and thus induces transcription, which is an essential process of AR transcription for both wild-type AR and AR splice variants. Importantly, the crystal structure of AR DBD dimer binding to AREs is available, which suggests the possibility and tractability to identify small-molecule inhibitors with novel mechanisms by targeting AR DBD through a rational, structure-based drug design. Moreover, as all mechanisms of resistance studied to date still involve the binding of AR to DNA, and the DBD exists in both wild-type AR and splice variants, targeting DBD represents a new approach to overcome resistance.

The activation of AR follows a well characterized pathway: in the cytoplasm, the receptor is associated with chaperone proteins that maintain agonist binding conformation of the AR (Georget, V. et al. Biochemistry (2002) 41:11824-11831). Upon binding of an androgen, the AR undergoes a series of conformational changes, disassociation from chaperones, dimerization and translocation into the nucleus (Fang, Y. F. et al. J. Biol. Chem. (1996) 271: 28697-28702; and Wong, C. I. et al. J. Biol. Chem. (1993) 268:19004-19012) where it further interacts with co-activator proteins at the AF2 site (Zhou, X. E. et al. J. Biol. Chem. (2010) 285:9161-9171). This event triggers the recruitment of RNA polymerase II and other factors to form a functional transcriptional complex with the AR.

Notably, the current anti-androgens such as bicalutamide, flutamide, nilutamide and MDV3100, all target this particular process. These anti-androgens act by binding to the AR ligand binding site. Thus, by preventing androgens from binding they also prevent conformational changes of the receptor that are necessary for co-activator interactions. While treatment with these AR inhibitors can initially suppress the prostate cancer growth, long term hormone therapy becomes progressively less effective (Taplin, M. E. et al. J. Clin. Oncol. (2003) 21:2673-8; and Tilley, W. D. et al. Cancer Res. (1994) 54:4096-4102). There is thus a significant need for additional compounds targeting AR for treatment of cancer.

Androgens also play a role in female cancers. One example is ovarian cancer where elevated levels of androgens are associated with an increased risk of developing ovarian cancer (K. J. Helzlsouer, et al., *JAMA* 274, 1926-1930 (1995); R. J. Edmondson, et al, *Br J Cancer* 86, 879-885 (2002)). The AR has been detected in a majority of ovarian cancers (H. A. Risch, *J Natl Cancer Inst* 90, 1774-1786 (1998); B. R. Rao & B. J. Slotman, *Endocr Rev* 12, 14-26 (1991); G. M. Clinton & W. Hua, *Crit Rev Oncol Hematol* 25, 1-9 (1997)), whereas estrogen receptor-alpha (ERa) and the progesterone receptor are detected in less than 50% of ovarian tumors.

SUMMARY

This invention is based in part on the fortuitous discovery that compounds described herein modulate androgen receptor (AR) activity. Specifically, compounds identified herein, show modulation of the androgen receptor DNA-binding domain (DBD).

In accordance with one embodiment, there is provided a compound having the structure of Formula I,

wherein,
A may be

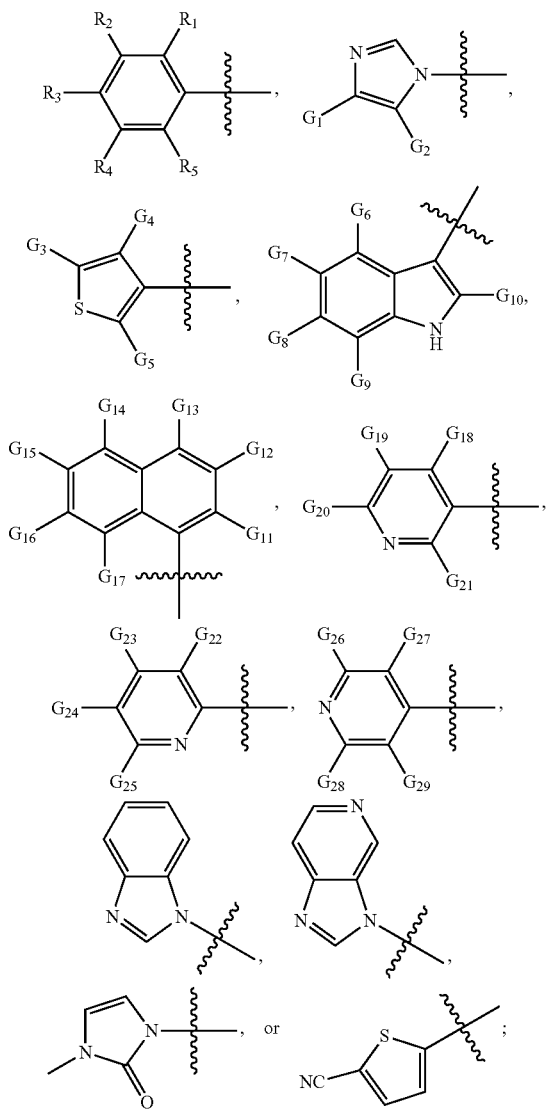

$R_1$ may be H, $OCH_3$, OH, $CH_3$, $NH_2$, Cl, $SO_2CH_3$, $OCH(CH_3)_2$, $O(CH_2)_2OCH_3$, Br, I, CN, $CH_2OH$, $CH_2CH_3$, $OCH_2CH_3$, $NHCH_3$, CN, or $CF_3$; $R_2$ may be H, $CF_3$, OH, $CH_3$, CN, $NH_2$, $CH_2OH$, $SO_2CH_3$, $OCH(CH_3)_2$, $O(CH_2)_2$ $OCH_3$, $CH_2CH_3$, or $OCH_2CH_3$; $R_2$ may be optionally selected from F, Cl, Br and I, provided that $R_1$ may be not one of Cl F, Br or I; $R_3$ may be H, F, CN, Cl, OH, $SCH_3$, $OCH_3$, $O(CH_2)_2OCH_3$, $CH_3$, $NH_2$, $SO_2CH_3$, $OCH(CH_3)_2$, $NHCH_3$, Br, I, $CH_2OH$, $CH_2CH_3$, $OCH_2CH_3$, or $CF_3$; $R_4$ may be H, $CH_3$, $NHCH_3$, OH, $CH_2OH$, F, CN, Cl, $SCH_3$, $OCH_3$, $O(CH_2)_2OCH_3$, $NH_2$, $SO_2CH_3$, $OCH(CH_3)_2$, $NHCH_3$, Br, I, $CH_2CH_3$, $OCH_2CH_3$, or $CF_3$; $R_5$ may be H, $CH_3$, $NHCH_3$, OH, $CH_2OH$, F, CN, Cl, $SCH_3$, $OCH_3$, $O(CH_2)_2OCH_3$, $NH_2$, $SO_2CH_3$, $OCH(CH_3)_2$, $NHCH_3$, Br, I, $CH_2CH_3$, $OCH_2CH_3$, or $CF_3$; may be Br, Cl, I, $CH_3$, H, F or OH; $G_2$ may be Br, Cl, H, I, $CH_3$, F or OH; $G_3$ may be Cl, H, $CH_3$, Br, I, F or OH; $G_4$ may be Cl, H, Br, I, F or OH; $G_4$ may be optionally $CH_3$ provided that both $G_3$ and $G_5$ are not both H; $G_5$ may be H, $CH_2OH$, Cl, Br, I, F or OH; $G_6$ may be H, $CH_2OH$, Cl, Br, I, F or OH; $G_7$ may be H, $CH_2OH$, Cl, Br, I, F or OH; $G_8$ may be H, $CH_2OH$, Cl, Br, I, F or OH; $G_9$ may be H, $CH_2OH$, Cl, Br, I, F or OH; $G_{10}$ may be H, $CH_2OH$, Cl, Br, I, F or OH; $G_{11}$-$G_{17}$ are independently selected from H, $CH_2OH$, Cl, Br, I, F or OH; $G_{18}$-$G_{21}$ are independently selected from H, $CH_2OH$, Cl, Br, I, F or OH; $G_{22}$-$G_{25}$ are independently selected from H, $CH_2OH$, Cl, Br, I, F or OH; $G_{26}$ may be H, $CH_2OH$, Cl, Br, I, F or OH; $G_{27}$ may be H, $CH_2OH$, Cl, Br, I, F or OH; $G_{28}$ may be H, $CH_2OH$, Cl, Br, I, F or OH; $G_{29}$ may be H, $CH_2OH$, Cl, Br, I, F or OH; D may be

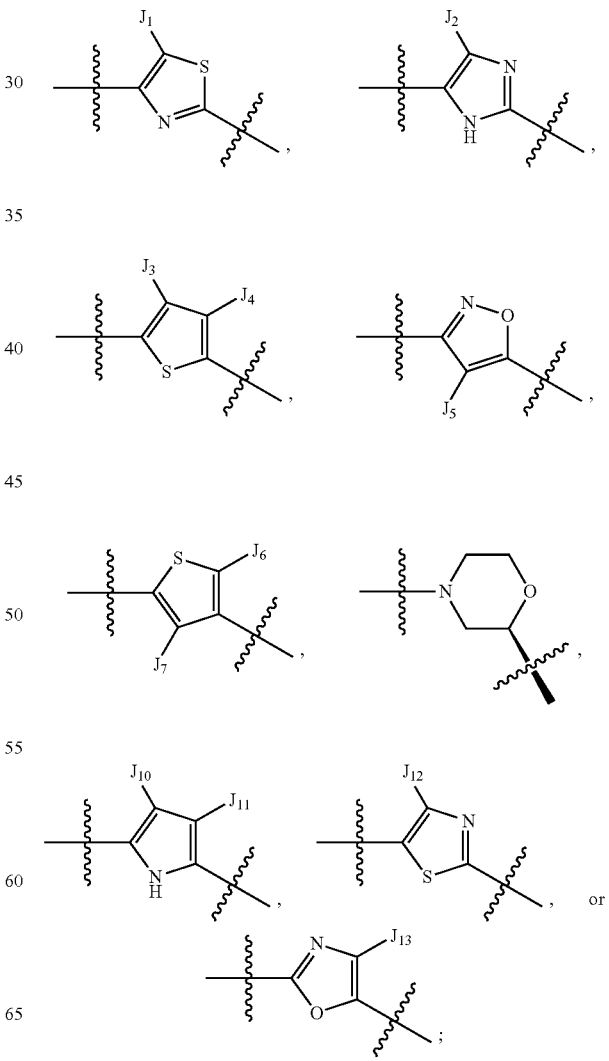

D may optionally be

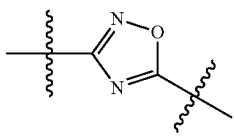

provided that A is

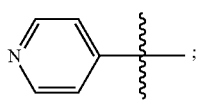

D may optionally be

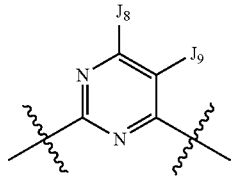

provided that $R_1$-$R_5$ are not all H; $J_1$ may be H, $CH_2CH_3$, $CH_3$, Cl, Br, I, F, COOH or OH; $J_1$ may be optionally $CH_3$ provided that $R_1$ may be not OH; $J_2$ may be H, $CH_3$, $CH_2CH_3$, Cl, Br, I, F or OH; $J_3$ may be H, CN, $CH_3$, $CH_2CH_3$, Cl, Br, I, F or OH; $J_4$ may be H, CN, $CH_3$, $CH_2CH_3$, Cl, Br, I, F or OH; $J_5$ may be H, CN, $CH_3$, $CH_2CH_3$, Cl, Br, I, F or OH; $J_6$ may be H, CN, $CH_3$, $CH_2CH_3$, Cl, Br, I, F or OH; $J_7$ may be H, CN, $CH_3$, $CH_2CH_3$, Cl, Br, I, F or OH; $J_8$ may be H, CN, $CH_3$, $CH_2CH_3$, Cl, Br, I, F or OH; $J_9$ may be H, CN, $CH_3$, $CH_2CH_3$, Cl, Br, I, F or OH; $J_{10}$ may be H, CN, $CH_3$, $CH_2CH_3$, Cl, Br, I, F or OH; $J_{11}$ may be H, CN, $CH_3$, $CH_2CH_3$, Cl, Br, I, F or OH; $J_{12}$ may be H, CN, $CH_3$, $CH_2CH_3$, Cl, Br, I, F or OH; $J_{13}$ may be H, CN, $CH_3$, $CH_2CH_3$, Cl, Br, I, F or OH; E may be

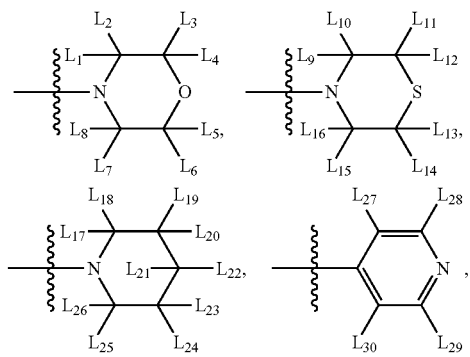

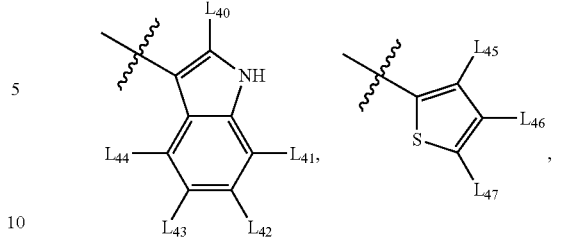

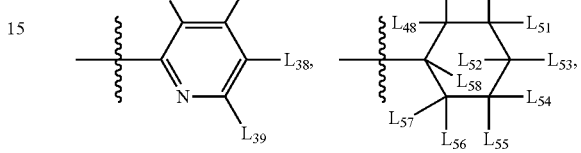

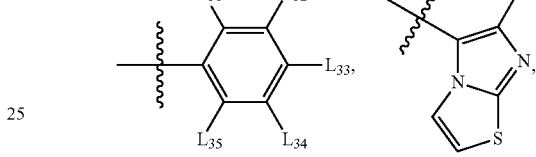

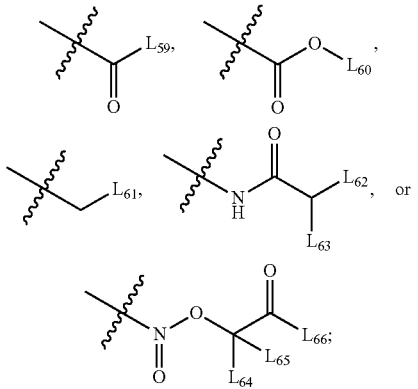

$L_1$-$L_8$ may be H, CN, $NH_2$, $NO_2$, $CH_3$, $CH_2CH_3$, Cl, Br, I, F, OH or $CF_3$; $L_9$-$L_{16}$ may be H, CN, $NH_2$, $NO_2$, $CH_3$, $CH_2CH_3$, Cl, Br, I, F, OH or $CF_3$; $L_{17}$-$L_{26}$ may be H, CN, $NH_2$, $NO_2$, $CH_3$, $CH_2CH_3$, Cl, Br, I, F, OH or $CF_3$; $L_{27}$-$L_{30}$ may be H, CN, $NH_2$, $NO_2$, $CH_3$, $CH_2CH_3$, Cl, Br, I, F, OH or $CF_3$; $L_{31}$-$L_{35}$ may be H, CN, $NH_2$, $NO_2$, $CH_3$, $CH_2CH_3$, Cl, Br, I, F, OH or $CF_3$; $L_{36}$-$L_{39}$ may be H, CN, $NH_2$, $NO_2$, $CH_3$, $CH_2CH_3$, Cl, Br, I, F, OH or $CF_3$; $L_{40}$-$L_{44}$ may be H, CN, $NH_2$, $NO_2$, $CH_3$, $CH_2CH_3$, Cl, Br, I, F, OH or $CF_3$; $L_{45}$-$L_{47}$ may be H, CN, $NH_2$, $NO_2$, $CH_3$, $CH_2CH_3$, Cl, Br, I, F, OH or $CF_3$; $L_48$-$L_58$ may be H, CN, $NH_2$, $NO_2$, $CH_3$, $CH_2CH_3$, Cl, Br, I, F, OH or $CF_3$; $L_{59}$ may be H, CN, $NH_2$, $NO_2$, $CH_3$, $CH_2CH_3$, Cl, Br, I, F, OH or $CF_3$; $L_{60}$ may be H, CN, $NH_2$, $NO_2$, $CH_3$, $CH_2CH_3$, Cl, Br, I, F, OH or $CF_3$; $L_{61}$ may be H, CN, $NH_2$, $NO_2$, $CH_3$, $CH_2CH_3$, Cl, Br, I, F, OH or $CF_3$; $L_{62}$ may be H, CN, $NH_2$, $NO_2$, $CH_3$, $CH_2CH_3$, Cl, Br, I, F, OH or $CF_3$; $L_{63}$ may be H, CN, $NH_2$, $NO_2$, $CH_3$, $CH_2CH_3$, Cl, Br, I, F, OH or $CF_3$; $L_{64}$ may be H, CN, $NH_2$, $NO_2$, $CH_3$, $CH_2CH_3$, Cl, Br, I, F, OH or $CF_3$; $L_{65}$ may be H, CN, $NH_2$, $NO_2$, $CH_3$, $CH_2CH_3$, Cl, Br, I, F, OH or $CF_3$; $L_{66}$ may be H, CN, $NH_2$, $NO_2$, $CH_3$, $CH_2CH_3$, Cl, Br, I, F, OH or $CF_3$; provided that the compound is not one or more of the following:

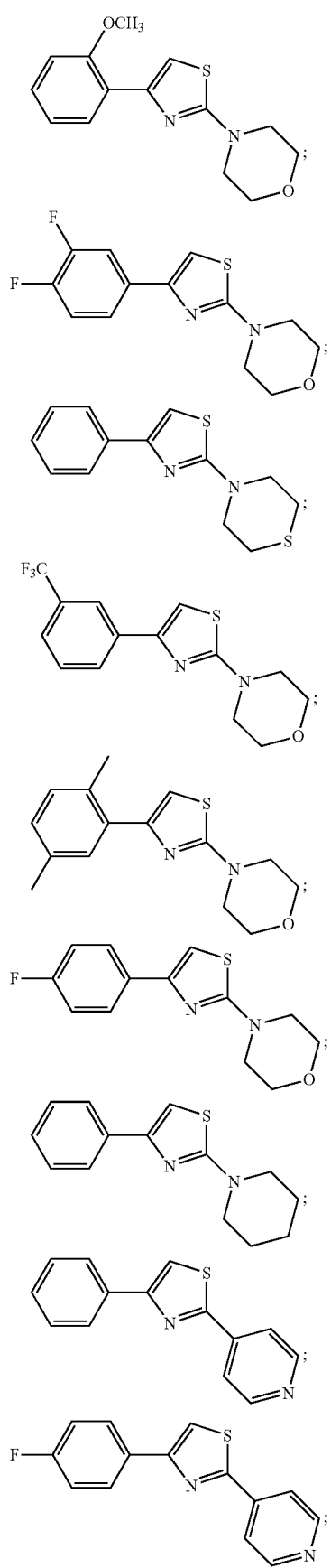
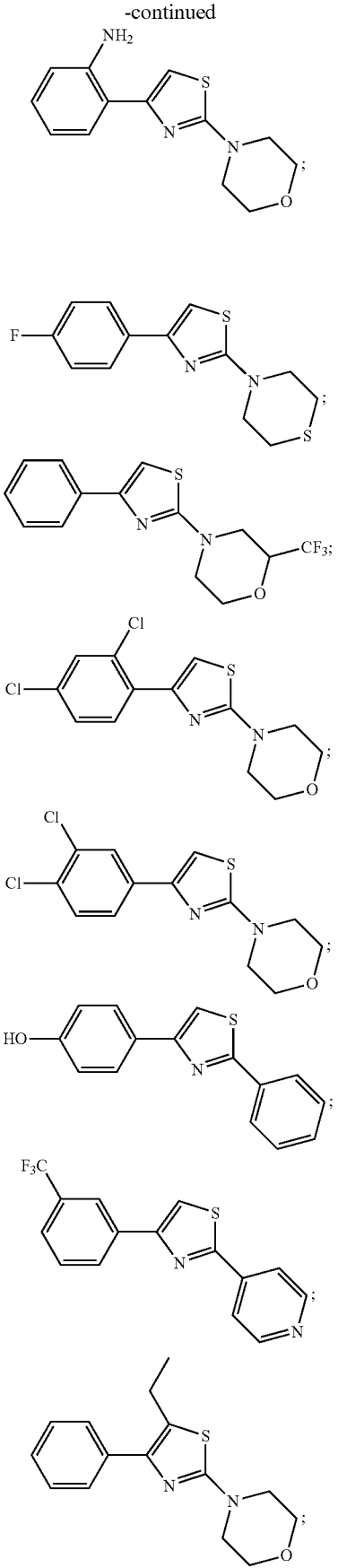

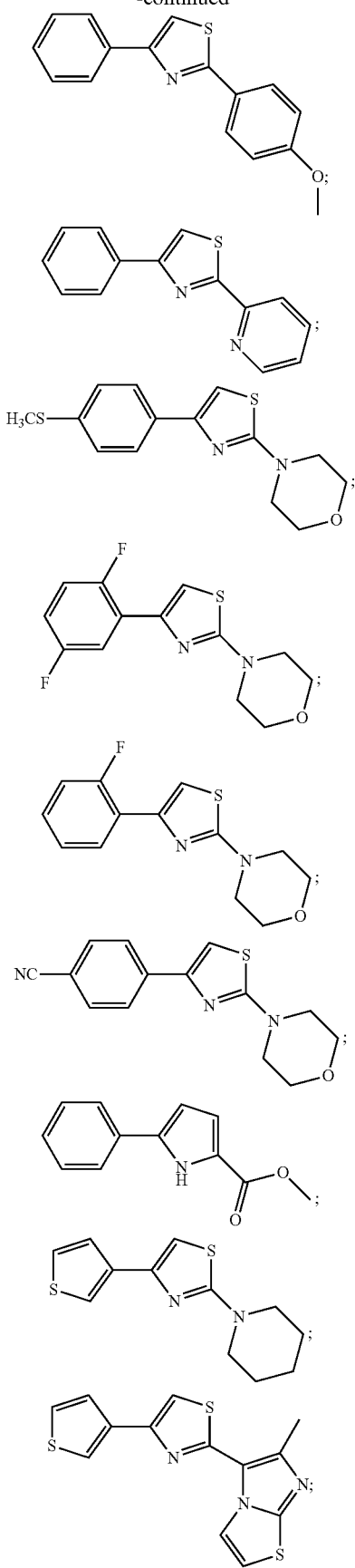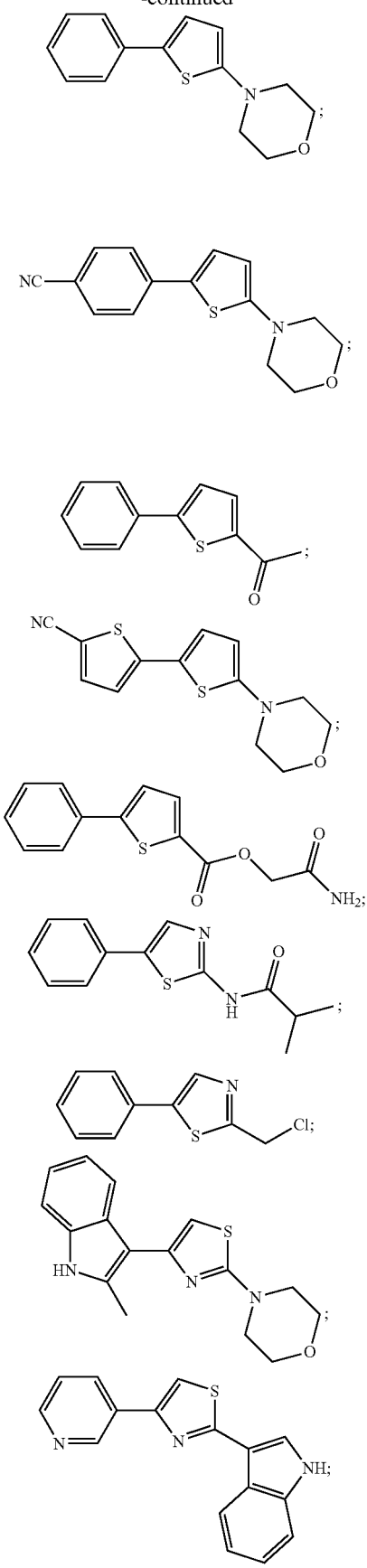

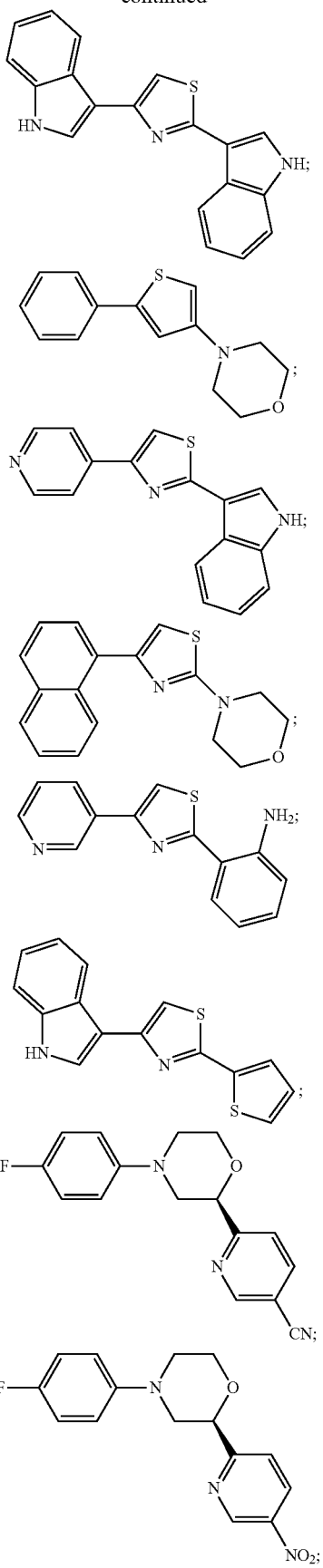
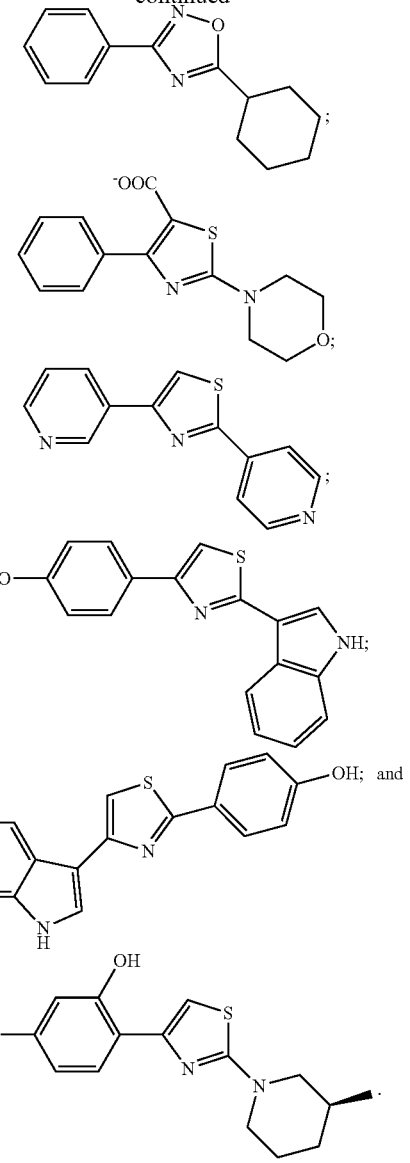
In accordance with a further embodiment, there is provided a method of modulating AR activity, the method comprising administering to a subject in need thereof, a compound having the structure of Formula I:
$$A—D\atop E,$$  I
wherein A may be
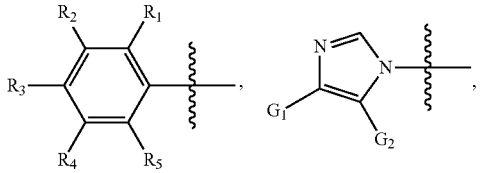

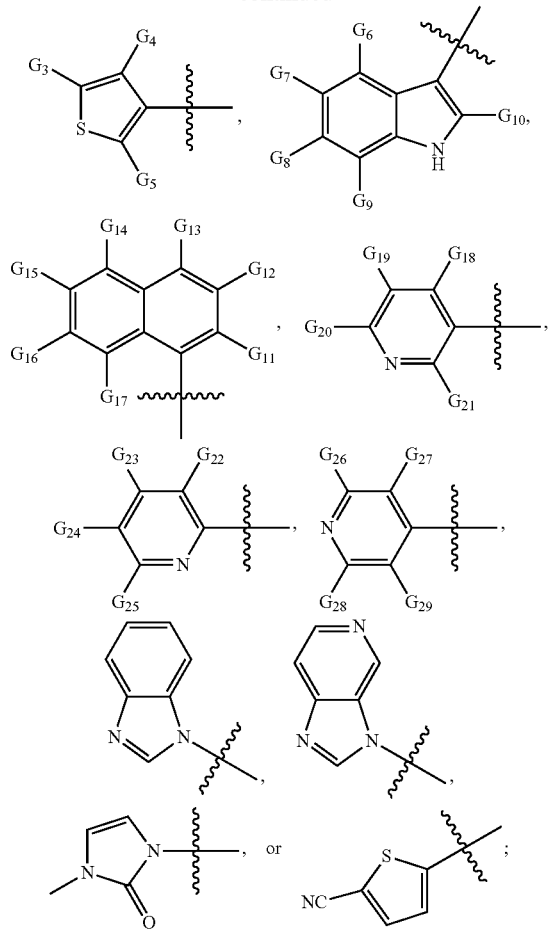

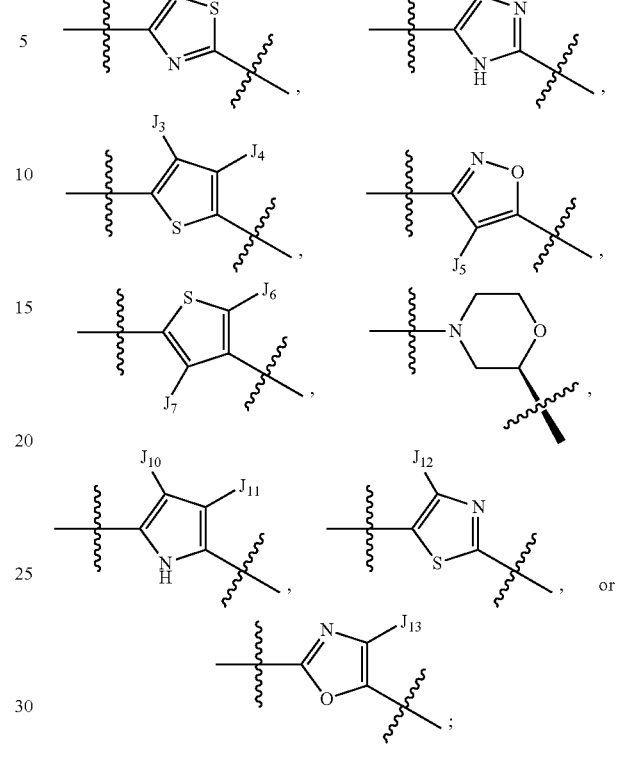

$R_1$ may be H, $OCH_3$, OH, $CH_3$, $NH_2$, Cl, $SO_2CH_3$, $OCH(CH_3)_2$, $O(CH_2)_2OCH_3$, Br, I, CN, $CH_2OH$, $CH_2CH_3$, $OCH_2CH_3$, $NHCH_3$, CN, or $CF_3$; $R_2$ may be H, $CF_3$, OH, $CH_3$, CN, $NH_2$, $CH_2OH$, $SO_2CH_3$, $OCH(CH_3)_2$, $O(CH_2)_2OCH_3$, $CH_2CH_3$, or $OCH_2CH_3$; $R_2$ may be optionally selected from F, Cl, Br and I, provided that $R_1$ may be not one of Cl F, Br or I; $R_3$ may be H, F, CN, Cl, OH, $SCH_3$, $OCH_3$, $O(CH_2)_2OCH_3$, $CH_3$, $NH_2$, $SO_2CH_3$, $OCH(CH_3)_2$, $NHCH_3$, Br, I, $CH_2OH$, $CH_2CH_3$, $OCH_2CH_3$, or $CF_3$; $R_4$ may be H, $CH_3$, $NHCH_3$, OH, $CH_2OH$, F, CN, Cl, $SCH_3$, $OCH_3$, $O(CH_2)_2OCH_3$, $NH_2$, $SO_2CH_3$, $OCH(CH_3)_2$, $NHCH_3$, Br, I, $CH_2CH_3$, $OCH_2CH_3$, or $CF_3$; $R_5$ may be H, $CH_3$, $NHCH_3$, OH, $CH_2OH$, F, CN, Cl, $SCH_3$, $OCH_3$, $O(CH_2)_2OCH_3$, $NH_2$, $SO_2CH_3$, $OCH(CH_3)_2$, $NHCH_3$, Br, I, $CH_2CH_3$, $OCH_2CH_3$, or $CF_3$; may be Br, Cl, I, $CH_3$, H, F or OH; $G_2$ may be Br, Cl, H, I, $CH_3$, F or OH; $G_3$ may be Cl, H, $CH_3$, Br, I, F or OH; $G_4$ may be Cl, H, Br, I, F or OH; $G_4$ may be optionally $CH_3$ provided that both $G_3$ and $G_5$ are not both H; $G_5$ may be H, $CH_2OH$, Cl, Br, I, F or OH; $G_6$ may be H, $CH_2OH$, Cl, Br, I, F or OH; $G_7$ may be H, $CH_2OH$, Cl, Br, I, F or OH; $G_8$ may be H, $CH_2OH$, Cl, Br, I, F or OH; $G_9$ may be H, $CH_2OH$, Cl, Br, I, F or OH; $G_{10}$ may be H, $CH_2OH$, Cl, Br, I, F or OH; $G_{11}$-$G_7$ are independently selected from H, $CH_2OH$, Cl, Br, I, F or OH; $G_{18}$-$G_{21}$ are independently selected from H, $CH_2OH$, Cl, Br, I, F or OH; $G_{22}$-$G_{25}$ may be independently selected from H, $CH_2OH$, Cl, Br, I, F or OH; $G_{26}$ may be H, $CH_2OH$, Cl, Br, I, F or OH; $G_{27}$ may be H, $CH_2OH$, Cl, Br, I, F or OH; $G_{28}$ may be H, $CH_2OH$, Cl, Br, I, F or OH; $G_{29}$ may be H, $CH_2OH$, Cl, Br, I, F or OH; D may be D may be optionally

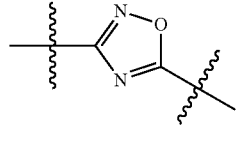

provided that A may be

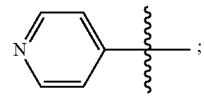

D may be optionally

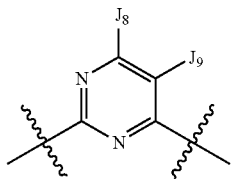

provided that $R_1$-$R_5$ are not all H; $J_1$ may be H, $CH_2CH_3$, $CH_3$, Cl, Br, I, F, COOH or OH; $J_1$ may be optionally $CH_3$ provided that $R_1$ may be not OH; $J_2$ may be H, $CH_3$, $CH_2CH_3$, Cl, Br, I, F or OH; $J_3$ may be H, CN, $CH_3$, $CH_2CH_3$, Cl, Br, I, F or OH; $J_4$ may be H, CN, $CH_3$, $CH_2CH_3$, Cl, Br, I, F or OH; $J_5$ may be H, CN, $CH_3$, $CH_2CH_3$, Cl, Br, I, F or OH; $J_6$ may be H, CN, $CH_3$, $CH_2CH_3$, Cl, Br, I, F or OH; $J_7$ may be H, CN, $CH_3$, $CH_2CH_3$, Cl, Br, I, F or OH; $J_8$ may be H, CN, $CH_3$, $CH_2CH_3$, Cl, Br, I, F or OH; $J_9$ may be H, CN, $CH_3$, $CH_2CH_3$, Cl, Br, I, F or OH; $J_{10}$ may be H, CN, $CH_3$, $CH_2CH_3$, Cl, Br, I, F or OH; $J_{11}$ may be H, CN, $CH_3$, $CH_2CH_3$, Cl, Br, I, F or OH; $J_{12}$ may be H, CN, $CH_3$, $CH_2CH_3$, Cl, Br, I, F or OH; $J_8$ may be H, CN, $CH_3$, $CH_2CH_3$, Cl, Br, I, F or OH; E may be

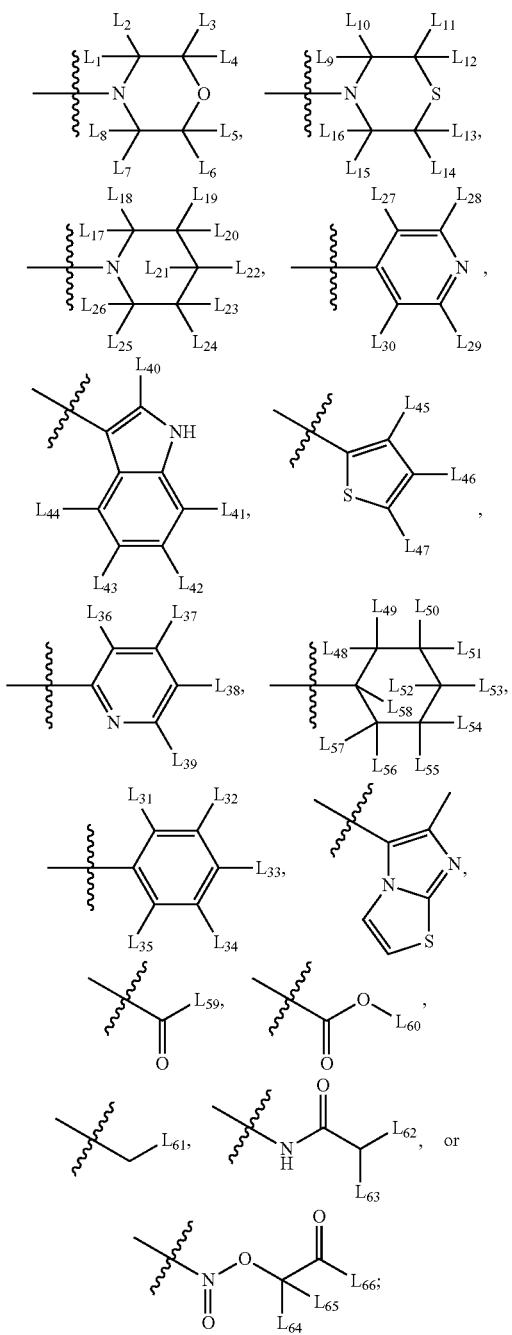

$L_1$-$L_8$ may be H, CN, $NH_2$, $NO_2$, $CH_3$, $CH_2CH_3$, Cl, Br, I, F, OH or $CF_3$; $L_9$-$L_{16}$ may be H, CN, $NH_2$, $NO_2$, $CH_3$, $CH_2CH_3$, Cl, Br, I, F, OH or $CF_3$; $L_{17}$-$L_{26}$ may be H, CN, $NH_2$, $NO_2$, $CH_3$, $CH_2CH_3$, Cl, Br, I, F, OH or $CF_3$; $L_{27}$-$L_{30}$ may be H, CN, $NH_2$, $NO_2$, $CH_3$, $CH_2CH_3$, Cl, Br, I, F, OH or $CF_3$; $L_{31}$-$L_{35}$ may be H, CN, $NH_2$, $NO_2$, $CH_3$, $CH_2CH_3$, Cl, Br, I, F, OH or $CF_3$; $L_{36}$-$L_{39}$ may be H, CN, $NH_2$, $NO_2$, $CH_3$, $CH_2CH_3$, Cl, Br, I, F, OH or $CF_3$; $L_{40}$-$L_{44}$ may be H, CN, $NH_2$, $NO_2$, $CH_3$, $CH_2CH_3$, Cl, Br, I, F, OH or $CF_3$; $L_{45}$-$L_{47}$ may be H, CN, $NH_2$, $NO_2$, $CH_3$, $CH_2CH_3$, Cl, Br, I, F, OH or $CF_3$; $L_{48}$-$L_{58}$ may be H, CN, $NH_2$, $NO_2$, $CH_3$, $CH_2CH_3$, Cl, Br, I, F, OH or $CF_3$; $L_{59}$ may be H, CN, $NH_2$, $NO_2$, $CH_3$, $CH_2CH_3$, Cl, Br, I, F, OH or $CF_3$; $L_{60}$ may be H, CN, $NH_2$, $NO_2$, $CH_3$, $CH_2CH_3$, Cl, Br, I, F, OH or $CF_3$; $L_{61}$ may be H, CN, $NH_2$, $NO_2$, $CH_3$, $CH_2CH_3$, Cl, Br, I, F, OH or $CF_3$; $L_{62}$ may be H, CN, $NH_2$, $NO_2$, $CH_3$, $CH_2CH_3$, Cl, Br, I, F, OH or $CF_3$; $L_{63}$ may be H, CN, $NH_2$, $NO_2$, $CH_3$, $CH_2CH_3$, Cl, Br, I, F, OH or $CF_3$; $L_{64}$ may be H, CN, $NH_2$, $NO_2$, $CH_3$, $CH_2CH_3$, Cl, Br, I, F, OH or $CF_3$; $L_{65}$ may be H, CN, $NH_2$, $NO_2$, $CH_3$, $CH_2CH_3$, Cl, Br, I, F, OH or $CF_3$; $L_{66}$ may be H, CN, $NH_2$, $NO_2$, $CH_3$, $CH_2CH_3$, Cl, Br, I, F, OH or $CF_3$.

In accordance with a further embodiment, there is provided a use of a compound described herein, for the manufacture of a medicament for modulating AR activity.

In accordance with a further embodiment, there is provided a use of a compound described herein claims 11-21, for modulating AR activity.

In accordance with a further embodiment, there is provided a compound described herein for modulating AR activity.

In accordance with a further embodiment, there is provided a pharmaceutical composition, comprising a compound described herein, and a pharmaceutically acceptable carrier or excipient.

In accordance with a further embodiment, there is provided a commercial package comprising a compound described herein and instructions for use in modulating AR activity.

In accordance with a further embodiment, there is provided a compound having the structure of Formula II,

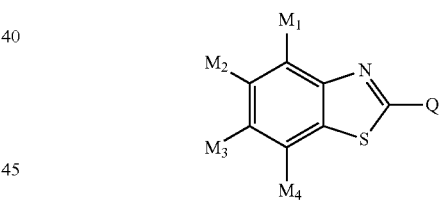

II wherein, Q may be

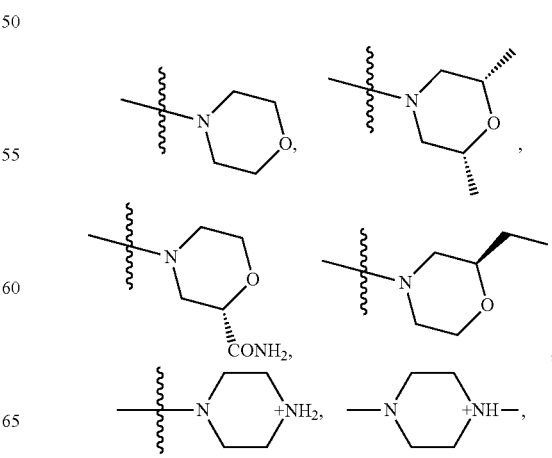

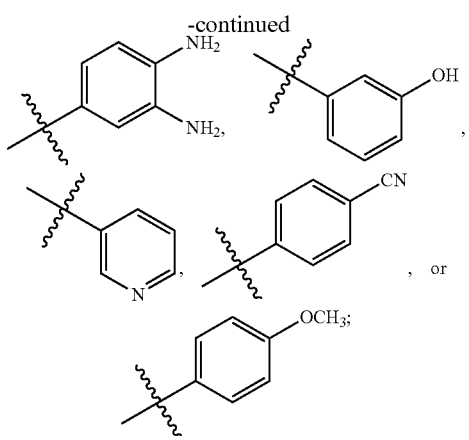

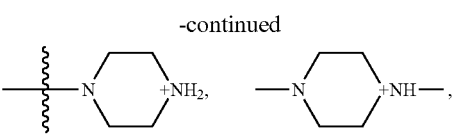

$M_1$ may be H, $CH_3$, F, $SO_2CH_3$, $OCH_3$, OH, $NO_2$, or $NH_2$;
$M_2$ may be H, $CH_3$, F, $SO_2CH_3$, $OCH_3$, OH, $NO_2$, or $NH_2$;
$M_3$ may be H, $CH_3$, F, $SO_2CH_3$, $OCH_3$, OH, $NO_2$, or $NH_2$;
and $M_4$ may be H, $CH_3$, F, $SO_2CH_3$, $OCH_3$, OH, $NO_2$, or $NH_2$;

provided that the compound is not one or more of the compounds found in the Series 2 section of TABLE 1, with the exception of compound 14409. The compound may be

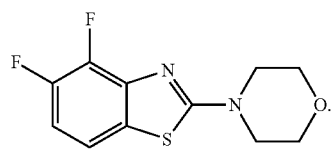

In accordance with a further embodiment, there is provided a method of modulating AR activity, the method including administering to a subject in need thereof, a compound having the structure of Formula II:

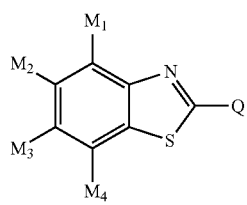

II wherein, Q may be

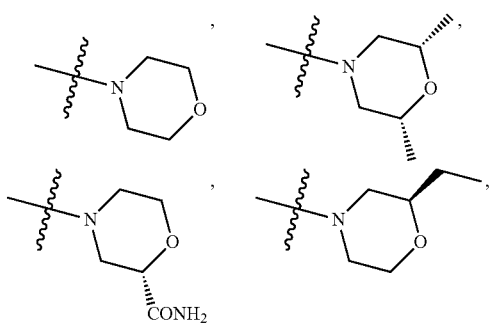

$M_1$ may be H, $CH_3$, F, $SO_2CH_3$, $OCH_3$, OH, $NO_2$, or $NH_2$;
$M_2$ may be H, $CH_3$, F, $SO_2CH_3$, $OCH_3$, OH, $NO_2$, or $NH_2$;
$M_3$ may be H, $CH_3$, F, $SO_2CH_3$, $OCH_3$, OH, $NO_2$, or $NH_2$;
and $M_4$ may be H, $CH_3$, F, $SO_2CH_3$, $OCH_3$, OH, $NO_2$, or $NH_2$.

In accordance with a further embodiment, there is provided a method of modulating AR activity, the method comprising administering to a subject in need thereof, a compound as set out in TABLE 1—Series 3-6.

In accordance with a further embodiment, there is provided a use of a compound described herein, for the manufacture of a medicament for modulating AR activity.

In accordance with a further embodiment, there is provided a se of a compound described herein for modulating AR activity.

In accordance with a further embodiment, there is provided a pharmaceutical composition, the pharmaceutical composition comprising a compound described herein, and a pharmaceutically acceptable carrier or excipient.

In accordance with a further embodiment, there is provided a commercial package, the commercial package comprising a compound described herein and instructions for use in modulating AR activity.

In accordance with a further embodiment, there is provided a use of a compound as set out in TABLE 1—Series 3-6, for the manufacture of a medicament for modulating AR activity.

In accordance with a further embodiment, there is provided a use of a compound a compound as set out in TABLE 1—Series 3-6, for modulating AR activity.

In accordance with a further embodiment, there is provided a pharmaceutical composition, comprising a compound as set out in TABLE 1—Series 3-6, and a pharmaceutically acceptable carrier or excipient.

In accordance with a further embodiment, there is provided a commercial package comprising, a compound as set out in TABLE 1—Series 3-6 and instructions for use in modulating AR activity.

A may be

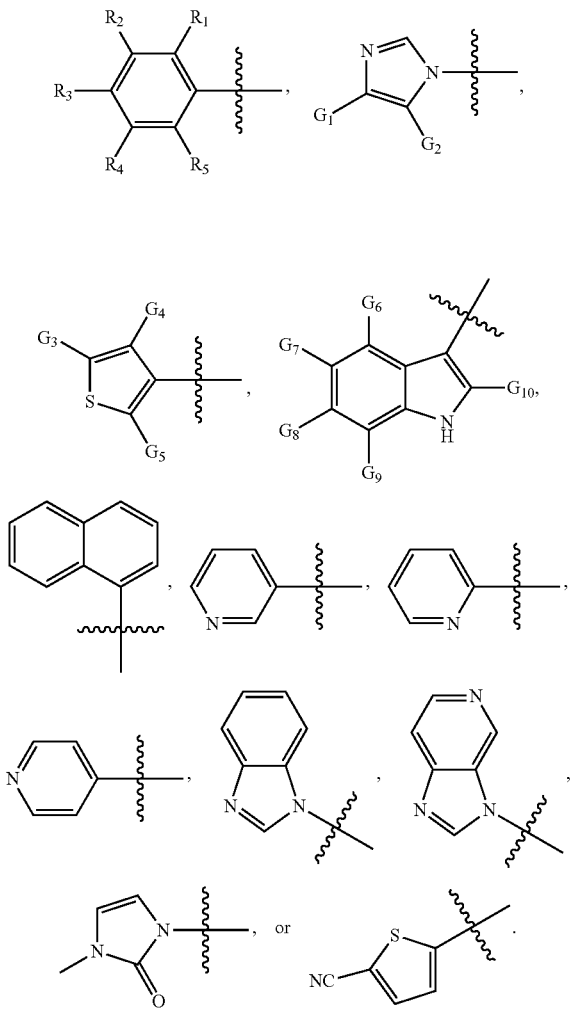

, or

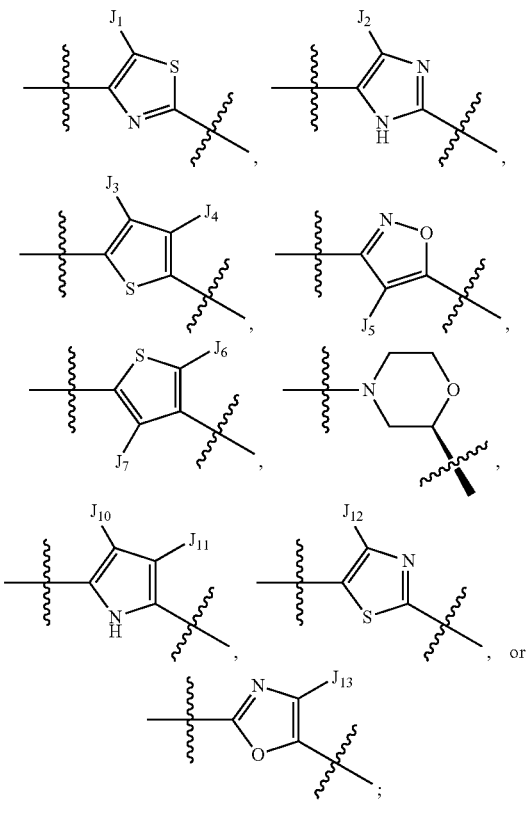

$R_1$ may be H, $OCH_3$, OH, $CH_3$, $NH_2$, Cl, $SO_2CH_3$, $OCH(CH_3)_2$, $O(CH_2)_2OCH_3$, Br, I, CN, $CH_2OH$, $CH_2CH_3$, $OCH_2CH_3$, $NHCH_3$, CN, or $CF_3$; $R_2$ may be H, $CF_3$, OH, $CH_3$, CN, $NH_2$, $CH_2OH$, $SO_2CH_3$, $OCH(CH_3)_2$, $O(CH_2)_2OCH_3$, $CH_2CH_3$, or $OCH_2CH_3$; $R_2$ may optionally be selected from F, Cl, Br and I, provided that $R_1$ is not one of Cl F, Br or I; $R_3$ may be H, F, CN, Cl, OH, $SCH_3$, $OCH_3$, $O(CH_2)_2OCH_3$, $CH_3$, $NH_2$, $SO_2CH_3$, $OCH(CH_3)_2$, $NHCH_3$, Br, I, $CH_2OH$, $CH_2CH_3$, $OCH_2CH_3$, or $CF_3$; $R_4$ may be H, $CH_3$, $NHCH_3$, OH, $CH_2OH$, F, CN, Cl, $SCH_3$, $OCH_3$, $O(CH_2)_2OCH_3$, $NH_2$, $SO_2CH_3$, $OCH(CH_3)_2$, $NHCH_3$, Br, I, $CH_2CH_3$, $OCH_2CH_3$, or $CF_3$; $R_5$ may be H, $CH_3$, $NHCH_3$, OH, $CH_2OH$, F, CN, Cl, $SCH_3$, $OCH_3$, $O(CH_2)_2OCH_3$, $NH_2$, $SO_2CH_3$, $OCH(CH_3)_2$, $NHCH_3$, Br, I, $CH_2CH_3$, $OCH_2CH_3$, or $CF_3$; $G_1$ may be Br, Cl, I, $CH_3$, H, F or OH; $G_2$ may be Br, Cl, H, I, $CH_3$, F or OH; $G_3$ may be Cl, H, $CH_3$, Br, I, F or OH; $G_4$ may be Cl, H, Br, I, F or OH; $G_4$ may be optionally $CH_3$ provided that both $G_3$ and $G_5$ are not both H; $G_5$ may be H, $CH_2OH$, Cl, Br, I, F or OH; $G_6$ may be H, $CH_2OH$, Cl, Br, I, F or OH; $G_7$ may be H, $CH_2OH$, Cl, Br, I, F or OH; $G_8$ may be H, $CH_2OH$, Cl, Br, I, F or OH; $G_9$ may be H, $CH_2OH$, Cl, Br, I, F or OH; $G_{10}$ may be H, $CH_2OH$, Cl, Br, I, F or OH; D may be provided that A is

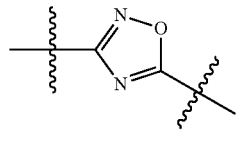 [SMILES: *c1noc(*)n1]

D may optionally be

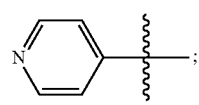

provided that $R_1$-$R_5$ are not all H; $J_1$ may be H, $CH_2CH_3$, $CH_3$, Cl, Br, I, F, COOH or OH; $J_1$ may be optionally $CH_3$ provided that $R_1$ may be not OH; $J_2$ may be H, $CH_3$, $CH_2CH_3$, Cl, Br, I, F, or OH; $J_3$ may be H, CN, $CH_3$, $CH_2CH_3$, Cl, Br, I, F or OH; $J_4$ may be H, CN, $CH_3$, $CH_2CH_3$, Cl, Br, I, F or OH; $J_5$ may be H, CN, $CH_3$, D may optionally be

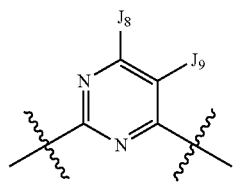

$CH_2CH_3$, Cl, Br, I, F or OH; $J_6$ may be H, CN, $CH_3$, $CH_2CH_3$, Cl, Br, I, F or OH; $J_7$ may be H, CN, $CH_3$, $CH_2CH_3$, Cl, Br, I, F or OH; $J_8$ may be H, CN, $CH_3$, $CH_2CH_3$, Cl, Br, I, F or OH; $J_9$ may be H, CN, $CH_3$, $CH_2CH_3$, Cl, Br, I, F or OH; $J_{10}$ may be H, CN, $CH_3$, $CH_2CH_3$, Cl, Br, I, F or OH; $J_{11}$ may be H, CN, $CH_3$, $CH_2CH_3$, Cl, Br, I, F or OH; $J_{12}$ may be H, CN, $CH_3$, $CH_2CH_3$, Cl, Br, I, F or OH; $J_{13}$ may be H, CN, $CH_3$, $CH_2CH_3$, Cl, Br, I, F or OH; E may be

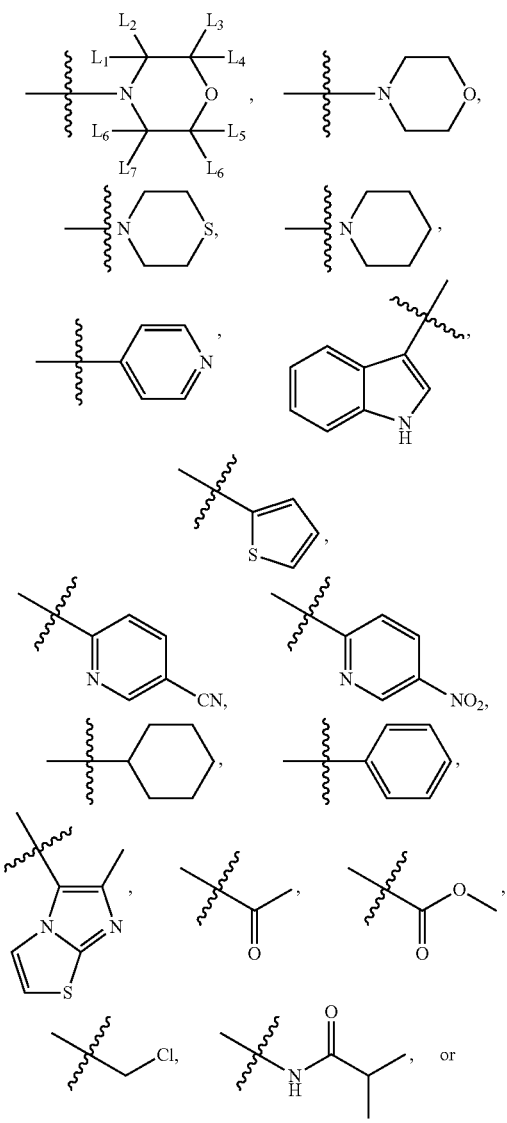

$L_1$ may be H, CN, $NH_2$, $NO_2$, $CH_3$, $CH_2CH_3$, Cl, Br, I, F, OH or $CF_3$; $L_2$ may be H, CN, $NH_2$, $NO_2$, $CH_3$, $CH_2CH_3$, Cl, Br, I, F, OH or $CF_3$; $L_3$ may be H, CN, $NH_2$, $NO_2$, $CH_3$, $CH_2CH_3$, Cl, Br, I, F, OH or $CF_3$; $L_4$ may be H, CN, $NH_2$, $NO_2$, $CH_3$, $CH_2CH_3$, Cl, Br, I, F, OH or $CF_3$; $L_5$ may be H, CN, $NH_2$, $NO_2$, $CH_3$, $CH_2CH_3$, Cl, Br, I, F, OH or $CF_3$; $L_6$ may be H, CN, $NH_2$, $NO_2$, $CH_3$, $CH_2CH_3$, Cl, Br, I, F, OH or $CF_3$; $L_7$ may be H, CN, $NH_2$, $NO_2$, $CH_3$, $CH_2CH_3$, Cl, Br, I, F, OH or $CF_3$; and $L_8$ may be H, CN, $NH_2$, $NO_2$, $CH_3$, $CH_2CH_3$, Cl, Br, I, F, OH or $CF_3$.

A may be

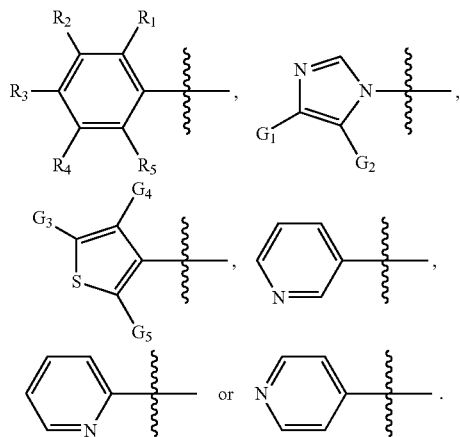

$R_1$ may be H, $OCH_3$, OH, $CH_3$, $NH_2$, Cl, $SO_2CH_3$, $OCH(CH_3)_2$, $O(CH_2)_2OCH_3$, Br, I, CN, $CH_2OH$, $CH_2CH_3$, $OCH_2CH_3$, $NHCH_3$, CN, or $CF_3$. $R_2$ may be H, $CF_3$, OH, $CH_3$, CN, $NH_2$, $CH_2OH$, $SO_2CH_3$, $OCH(CH_3)_2$, $O(CH_2)_2OCH_3$, $CH_2CH_3$, or $OCH_2CH_3$. $R_2$ may be optionally selected from F, Cl, Br and I, provided that $R_1$ may be not one of Cl F, Br or I. $R_3$ may be H, F, CN, Cl, OH, $SCH_3$, $OCH_3$, $O(CH_2)_2OCH_3$, $CH_3$, $NH_2$, $SO_2CH_3$, $OCH(CH_3)_2$, $NHCH_3$, Br, I, $CH_2OH$, $CH_2CH_3$, $OCH_2CH_3$, or $CF_3$. $R_4$ may be H, $CH_3$, $NHCH_3$, OH, $CH_2OH$, F, CN, Cl, $SCH_3$, $OCH_3$, $O(CH_2)_2OCH_3$, $NH_2$, $SO_2CH_3$, $OCH(CH_3)_2$, $NHCH_3$, Br, I, $CH_2CH_3$, $OCH_2CH_3$, or $CF_3$. $R_5$ may be H, $CH_3$, $NHCH_3$, OH, $CH_2OH$, F, CN, Cl, $SCH_3$, $OCH_3$, $O(CH_2)_2OCH_3$, $NH_2$, $SO_2CH_3$, $OCH(CH_3)_2$, $NHCH_3$, Br, I, $CH_2CH_3$, $OCH_2CH_3$, or $CF_3$. $G_1$ may be Br, Cl, I, $CH_3$, H, F or OH. $G_2$ may be Br, Cl, H, I, $CH_3$, F or OH. $G_3$ may be Cl, H, $CH_3$, Br, I, F or OH. $G_4$ may be Cl, H, Br, I, F or OH. $G_4$ may be optionally $CH_3$ provided that both $G_3$ and $G_5$ are not both H. $G_5$ may be H, $CH_2OH$, Cl, Br, I, F or OH. D may be

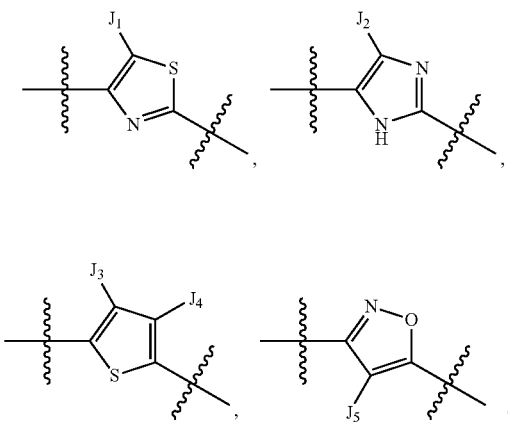

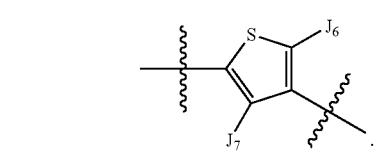

D may optionally be

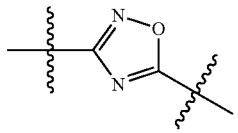 [SMILES: *c1noc(*)n1]

provided that A is

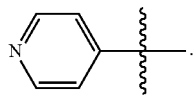

D may optionally be

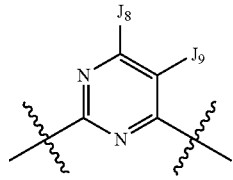

provided that $R_1$-$R_5$ are not all H. $J_1$ may be H, $CH_2CH_3$, $CH_3$, Cl, Br, I, F or OH. $J_1$ may be optionally $CH_3$ provided that $R_1$ may be not OH. $J_2$ may be H, $CH_3$, $CH_2CH_3$, Cl, Br, I, F or OH. $J_3$ may be H, CN, $CH_3$, $CH_2CH_3$, Cl, Br, I, F or OH. $J_4$ may be H, CN, $CH_3$, $CH_2CH_3$, Cl, Br, I, F or OH. $J_5$ may be H, CN, $CH_3$, $CH_2CH_3$, Cl, Br, I, F or OH. $J_6$ may be H, CN, $CH_3$, $CH_2CH_3$, Cl, Br, I, F or OH. $J_7$ may be H, CN, $CH_3$, $CH_2CH_3$, Cl, Br, I, F or OH. $J_8$ may be H, CN, $CH_3$, $CH_2CH_3$, Cl, Br, I, F or OH. $J_9$ may be H, CN, $CH_3$, $CH_2CH_3$, Cl, Br, I, F or OH. E may be

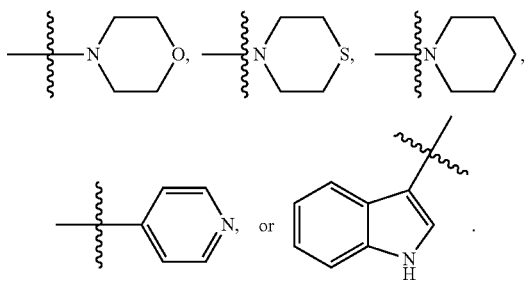

A may be

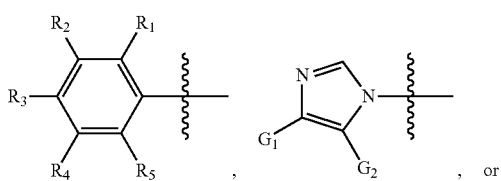

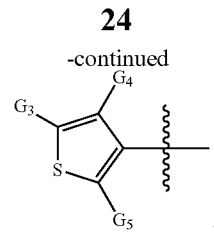

$R_1$ may be H, $OCH_3$, OH, $CH_3$, $NH_2$, Cl, $SO_2CH_3$, $OCH(CH_3)_2$, $O(CH_2)_2OCH_3$, Br, I, CN, $CH_2OH$, $CH_2CH_3$, $OCH_2CH_3$, $NHCH_3$, CN, or $CF_3$. $R_2$ may be H, $CF_3$, OH, $CH_3$, $NH_2$, CN, $CH_2OH$, $SO_2CH_3$, $OCH(CH_3)_2$, $O(CH_2)_2OCH_3$, $CH_2CH_3$, or $OCH_2CH_3$. $R_2$ may be optionally selected from F, Cl, Br and I, provided that $R_1$ may be not one of Cl F, Br or I. $R_3$ may be H, F, CN, Cl, OH, $SCH_3$, $OCH_3$, $O(CH_2)_2OCH_3$, $CH_3$, $NH_2$, $SO_2CH_3$, $OCH(CH_3)_2$, $NHCH_3$, Br, I, $CH_2OH$, $CH_2CH_3$, $OCH_2CH_3$, or $CF_3$. $R_4$ may be H, $CH_3$, $NHCH_3$, OH, $CH_2OH$, F, CN, Cl, $SCH_3$, $OCH_3$, $O(CH_2)_2OCH_3$, $NH_2$, $SO_2CH_3$, $OCH(CH_3)_2$, $NHCH_3$, Br, I, $CH_2CH_3$, $OCH_2CH_3$, or $CF_3$. $R_5$ may be H, $CH_3$, $NHCH_3$, OH, $CH_2OH$, F, CN, Cl, $SCH_3$, $OCH_3$, $O(CH_2)_2OCH_3$, $NH_2$, $SO_2CH_3$, $OCH(CH_3)_2$, $NHCH_3$, Br, I, $CH_2CH_3$, $OCH_2CH_3$, or $CF_3$. $G_1$ may be Br, Cl, I, $CH_3$, H, F or OH. $G_2$ may be Br, Cl, H, I, $CH_3$, F or OH. $G_3$ may be Cl, H, $CH_3$, Br, I, F or OH. $G_4$ may be Cl, H, Br, I, F or OH. $G_4$ may be optionally $CH_3$ provided that both $G_3$ and $G_5$ are not both H. $G_5$ may be H, $CH_2OH$, Cl, Br, I, F or OH. D may be

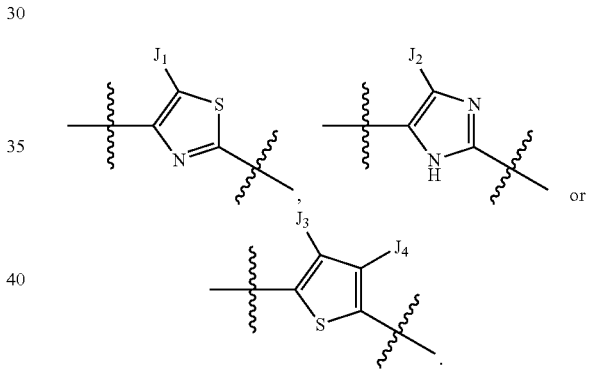

$J_1$ may be H, $CH_2CH_3$, $CH_3$, Cl, Br, I, F or OH. $J_1$ may be optionally $CH_3$ provided that $R_1$ may be not OH. $J_2$ may be H, $CH_3$, $CH_2CH_3$, Cl, Br, I, F or OH. $J_3$ may be H, CN, $CH_3$, $CH_2CH_3$, Cl, Br, I, F or OH. $J_4$ may be H, CN, $CH_3$, $CH_2CH_3$, Cl, Br, I, F or OH. E may be

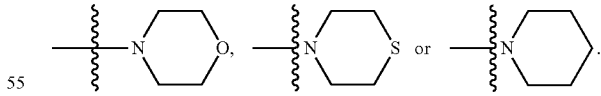

A may be

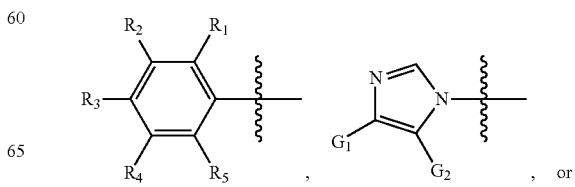

25
-continued

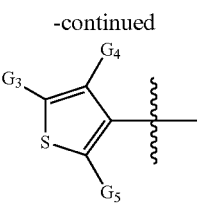

R$_1$ may be H, OCH$_3$, OH, CH$_3$, NH$_2$, Cl, SO$_2$CH$_3$, OCH(CH$_3$)$_2$, O(CH$_2$)$_2$OCH$_3$, Br, I, CN, CH$_2$OH, CH$_2$CH$_3$, OCH$_2$CH$_3$, or CF$_3$. R$_2$ may be H, CF$_3$, OH, CN, CH$_3$, or NH$_2$. R$_2$ may be optionally selected from F, Cl, Br and I, provided that R, may be not one of Cl F, Br or I. R$_3$ may be H, F, CN, Cl, OH, SCH$_3$, OCH$_3$, CH$_3$, NH$_2$, Br, I, CH$_2$OH, CH$_2$CH$_3$ or CF$_3$. R$_4$ may be H, CH$_3$, NHCH$_3$, OH, CH$_2$OH, F, CN, Cl, SCH$_3$, OCH$_3$, NH$_2$, Br, I or CF$_3$. R$_5$ may be H, CH$_3$, OH, F, CN, Cl, NH$_2$, Br, I or CF$_3$. G, may be Br, Cl, I, CH$_3$, H, F or OH. G$_2$ may be Br, Cl, H, I, CH$_3$, F or OH. G$_3$ may be Cl, H, CH$_3$, Br, I, F or OH. G$_4$ may be Cl, H, Br, I, F or OH. G$_4$ may optionally be CH$_3$ provided that both G$_3$ and G$_5$ are not both H. G$_5$ may be H, CH$_2$OH, Cl, Br, I, F or OH. D may be 26
-continued

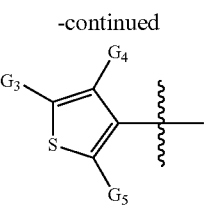

R$_1$ may be H, OCH$_3$, OH, CH$_3$, NH$_2$, Cl, SO$_2$CH$_3$, OCH(CH$_3$)$_2$, O(CH$_2$)$_2$OCH$_3$, Br, I, CN, CH$_2$OH, CH$_2$CH$_3$, OCH$_2$CH$_3$, or CF$_3$. R$_2$ may be H, CF$_3$, OH, CN, CH$_3$, or NH$_2$. R$_2$ may be optionally selected from F, Cl, Br and I, provided that R$_1$ may be not one of Cl F, Br or I. R$_3$ may be H, F, CN, Cl, OH, SCH$_3$, OCH$_3$, CH$_3$, NH$_2$, Br, I or CF$_3$. R$_4$ may be H, CH$_3$, NHCH$_3$, OH, CH$_2$OH, F, Cl, OCH$_3$, NH$_2$, Br, I or CF$_3$. R$_5$ may be H, CH$_3$, OH, F, CN, Cl, NH$_2$, Br, I or CF$_3$. G, may be Br, Cl, I, CH$_3$, H, F or OH. G$_2$ may be Br, Cl, H, I, CH$_3$, F or OH. G$_3$ may be Cl, H, CH$_3$, Br, I, F or OH. G$_4$ may be Cl, H, Br, I, F or OH. G$_4$ may be optionally CH$_3$ provided that both G$_3$ and G$_5$ are not both H. G$_5$ may be H, CH$_2$OH, Cl, Br, I, F or OH. D may be

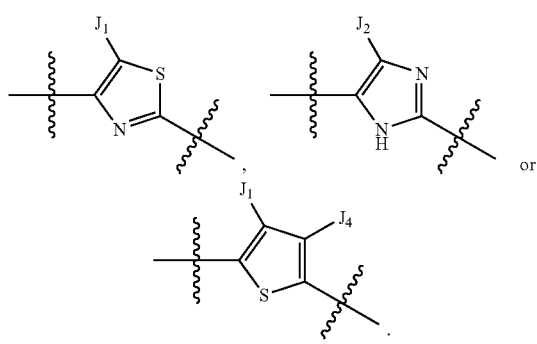

J$_1$ may be H, CH$_2$CH$_3$, CH$_3$, Cl, Br, I, F or OH. J$_1$ may be optionally CH$_3$ provided that R$_1$ may be not OH. J$_2$ may be H, CH$_3$, Cl, Br, I, F or OH. J$_3$ may be H, CN, CH$_3$, Cl, Br, I, F or OH. J$_4$ may be H, CN, CH$_3$, Cl, Br, I, F or OH. E may be J$_1$ may be H, CH$_2$CH$_3$, CH$_3$, Cl, Br, I, F or OH. J$_1$ may optionally be CH$_3$ provided that R$_1$ may be not OH. J$_2$ may be H, CH$_3$, Cl, Br, I, F or OH. J$_3$ may be H, CN, CH$_3$, Cl, Br, I, F or OH. J$_4$ may be H, CN, CH$_3$, Cl, Br, I, F or OH. E may be

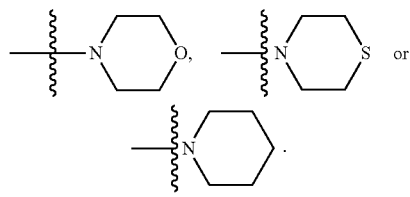

A may be

A may be

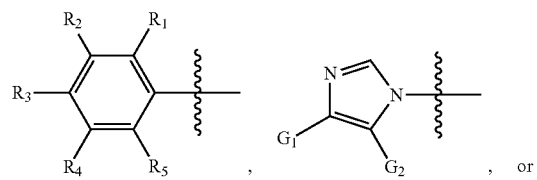

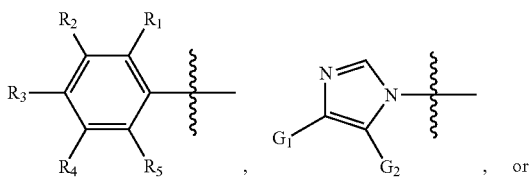

-continued

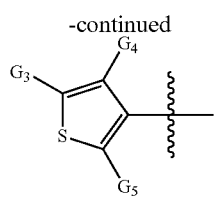

$R_1$ may be H, $OCH_3$, OH, $CH_3$, $NH_2$, Cl, $SO_2CH_3$, $OCH(CH_3)_2$, or $O(CH_2)_2OCH_3$. $R_2$ may be H or $CF_3$. $R_2$ may optionally be selected from F and Cl, provided that R, is not one of Cl F, Br or I. $R_3$ may be H, F, CN, Cl, OH or $SCH_3$. $R_4$ may be H, $CH_3$, $NHCH_3$, OH, $CH_2OH$ or F. $R_5$ may be H. $G_1$ may be Br, Cl, I or $CH_3$. $G_2$ may be Br, Cl, H, I or $CH_3$. $G_3$ may be Cl, H, $CH_3$ or Br. $G_4$ may be Cl, H or Br. $G_4$ may be optionally $CH_3$ provided that both $G_3$ and $G_5$ are not both H. $G_5$ may be H or $CH_2OH$. D may be

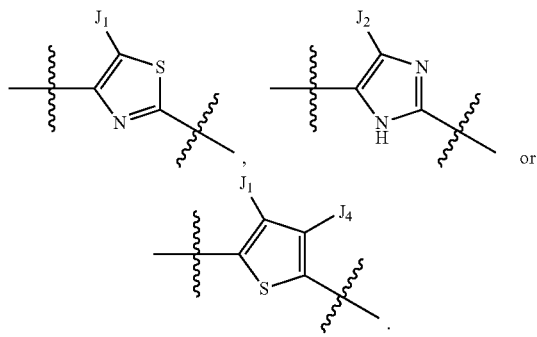

$J_1$ may be H or $CH_2CH_3$. $J_1$ may be optionally $CH_3$ provided that $R_1$ may be not OH. $J_2$ may be H. $J_3$ may be H or CN. $J_4$ may be H. E may be

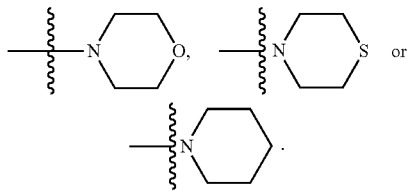

A may be

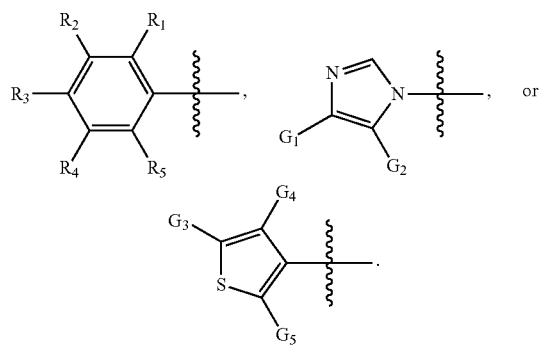

$R_1$ may be H, $OCH_3$, OH or $CH_3$. $R_2$ may be H or $CF_3$. $R_2$ may optionally be selected from F and Cl, provided that $R_1$ may be not one of Cl F, Br or I. $R_3$ may be H or F. $R_4$ may be H or $CH_3$. $R_5$ may be H. $G_1$ may be Br or Cl. $G_2$ may be Br, Cl or H. $G_3$ may be Cl, H, $CH_3$ or Br. $G_4$ may be Cl, H or Br. $G_4$ may be optionally $CH_3$ provided that both $G_3$ and $G_5$ are not both H. $G_5$ may be H or $CH_2OH$. D may be

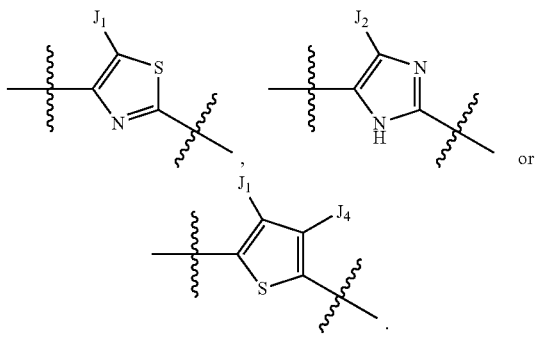

$J_1$ may be H. $J_2$ may be H. $J_3$ may be H. $J_4$ may be H. E may be

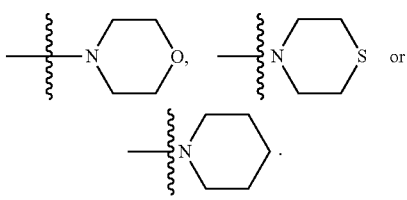

The compound may be selected from one or more of the following compounds:

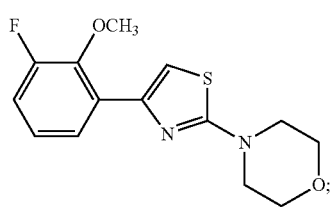

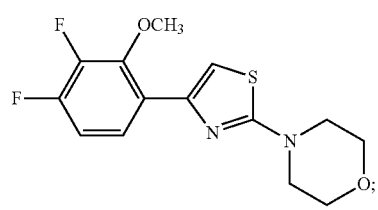

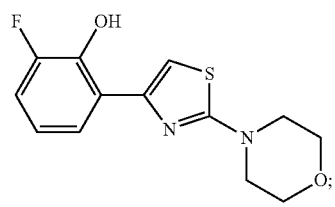

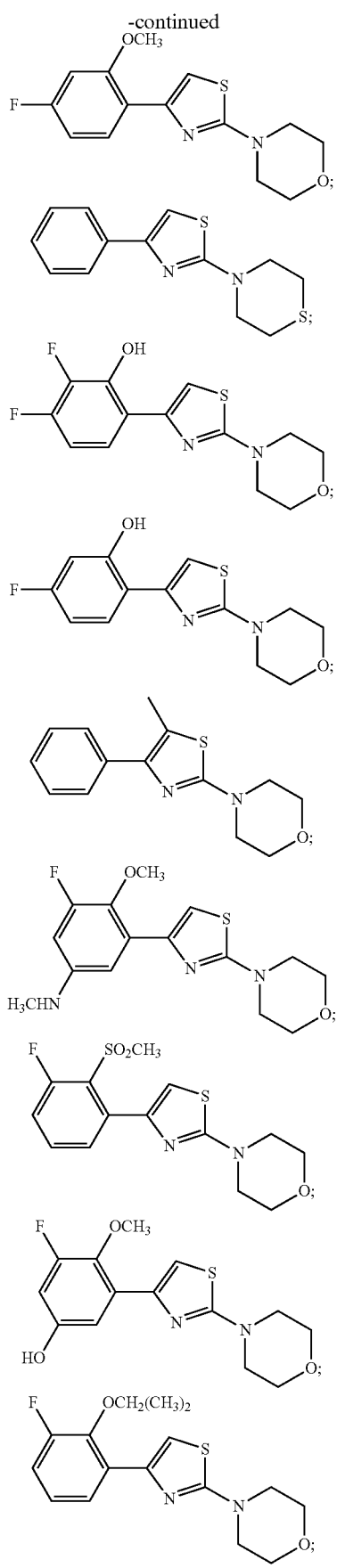
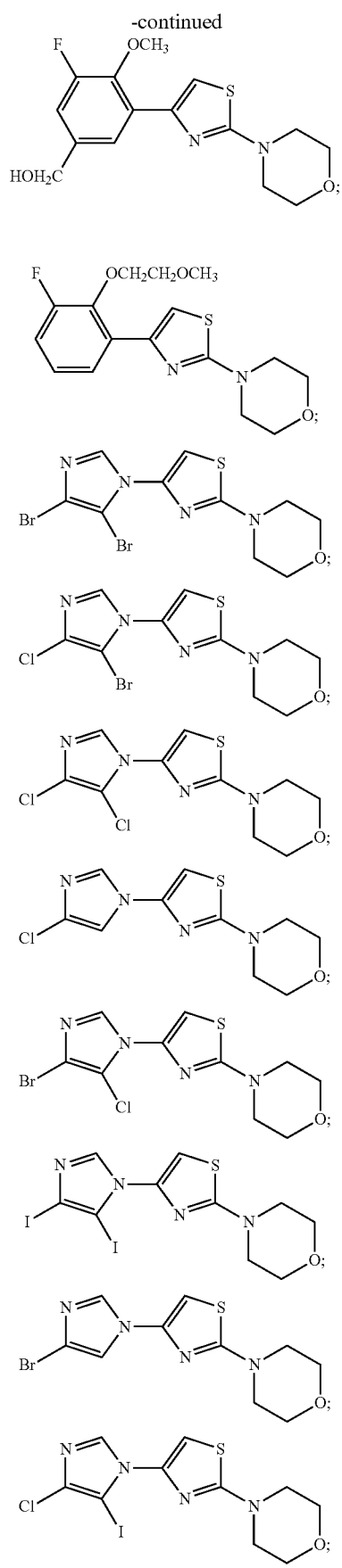

-continued
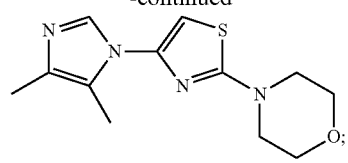
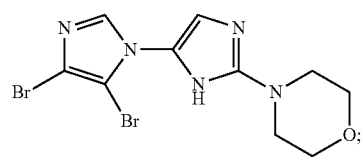
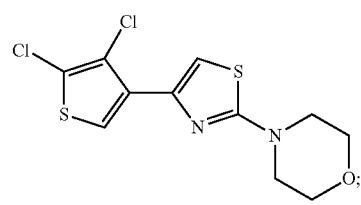
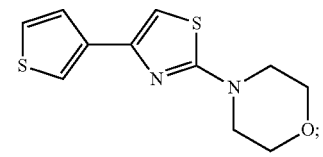
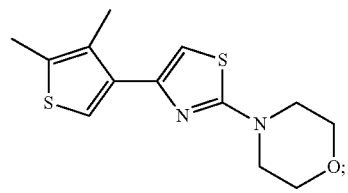
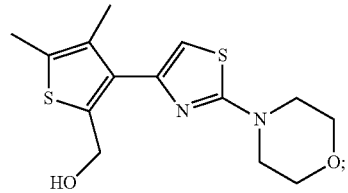
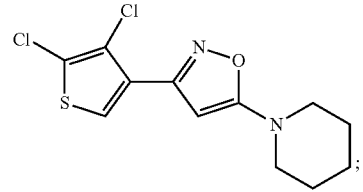
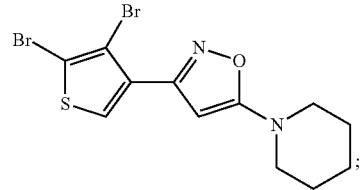
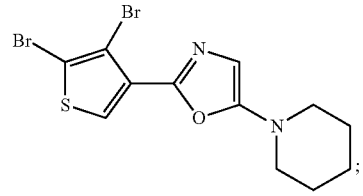
-continued
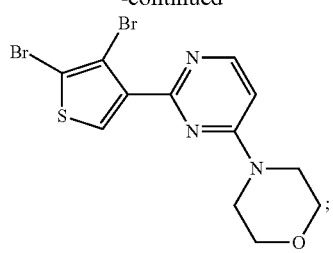
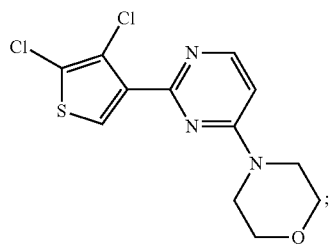
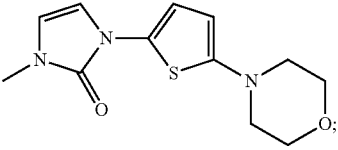
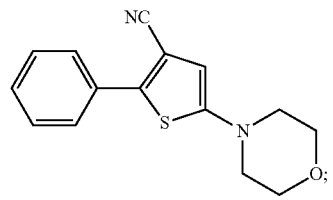
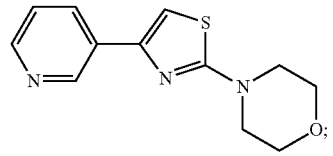
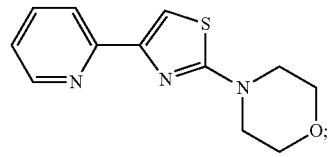
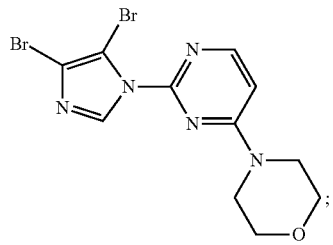
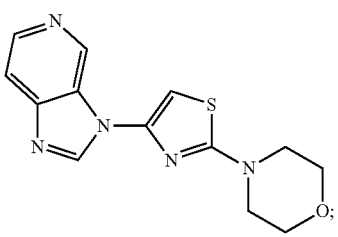

-continued
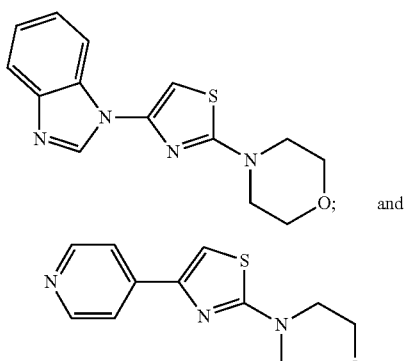
and
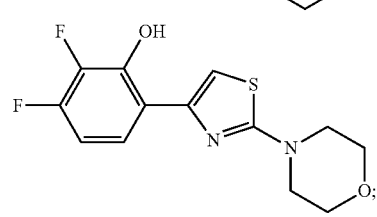
The compound may be selected from one or more of the following compounds:
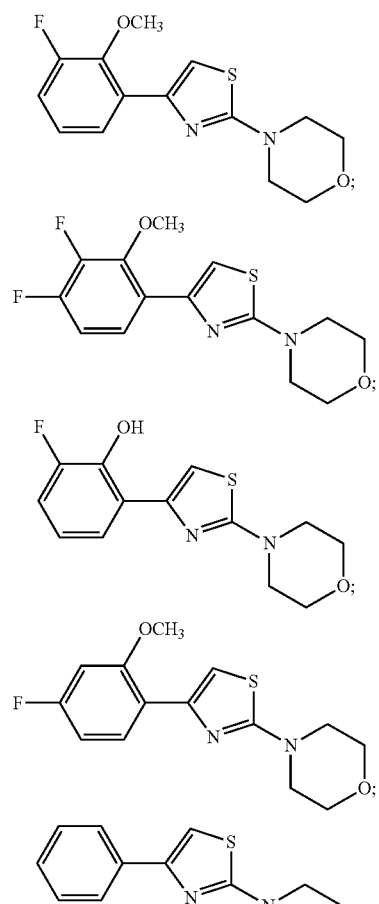
-continued
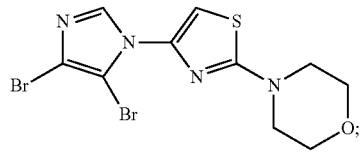
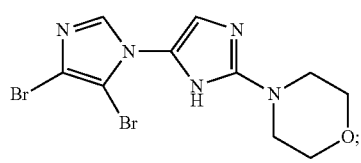
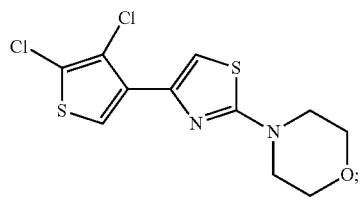
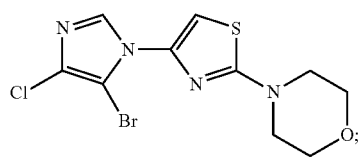
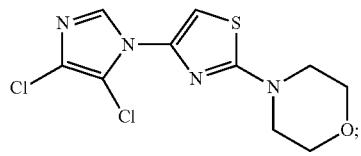
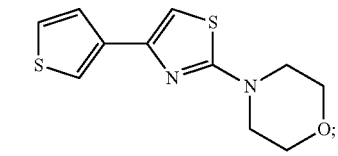
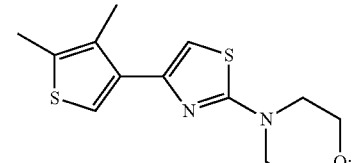
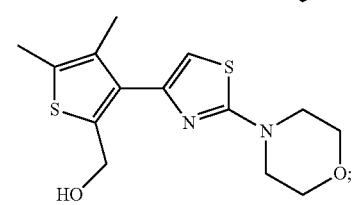
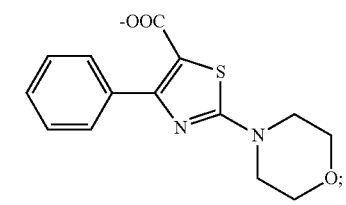

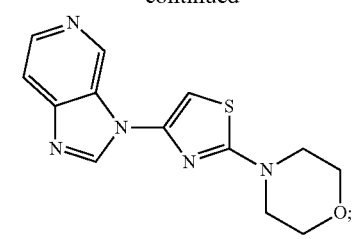
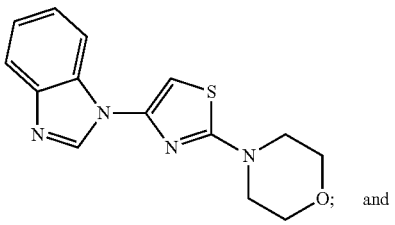
and
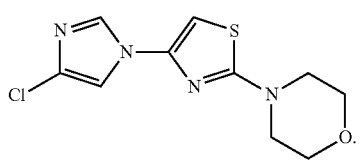
The compound may be selected from one or more of the following compounds:
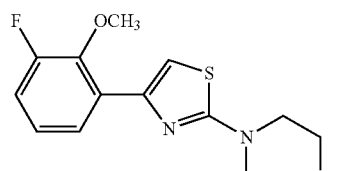
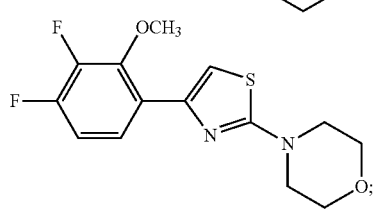
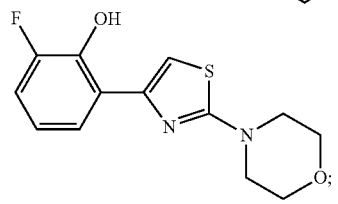
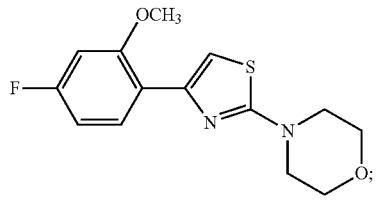
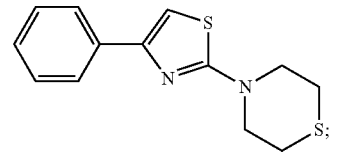
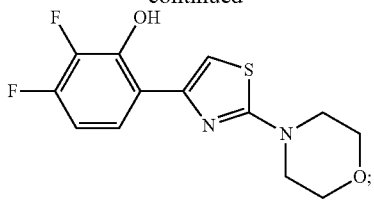
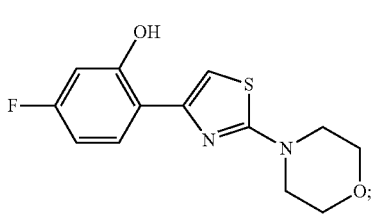
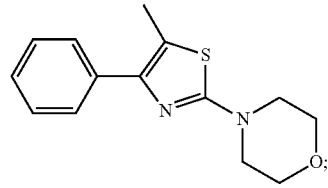
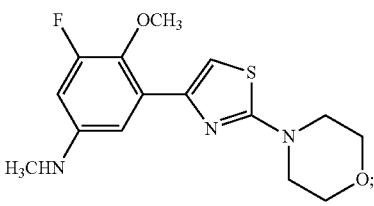
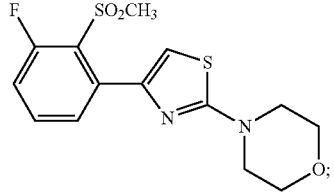
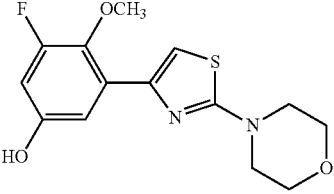
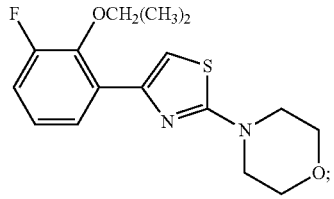
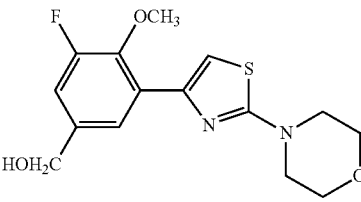

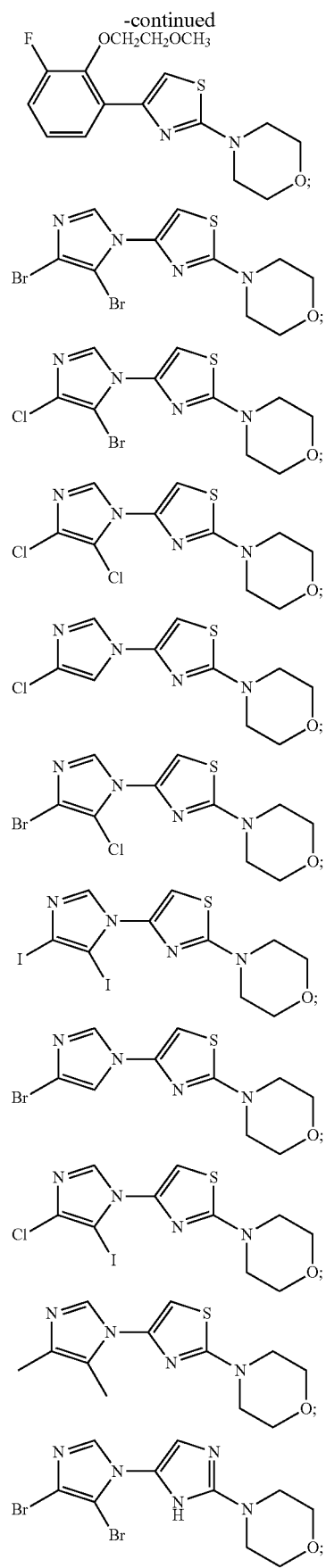
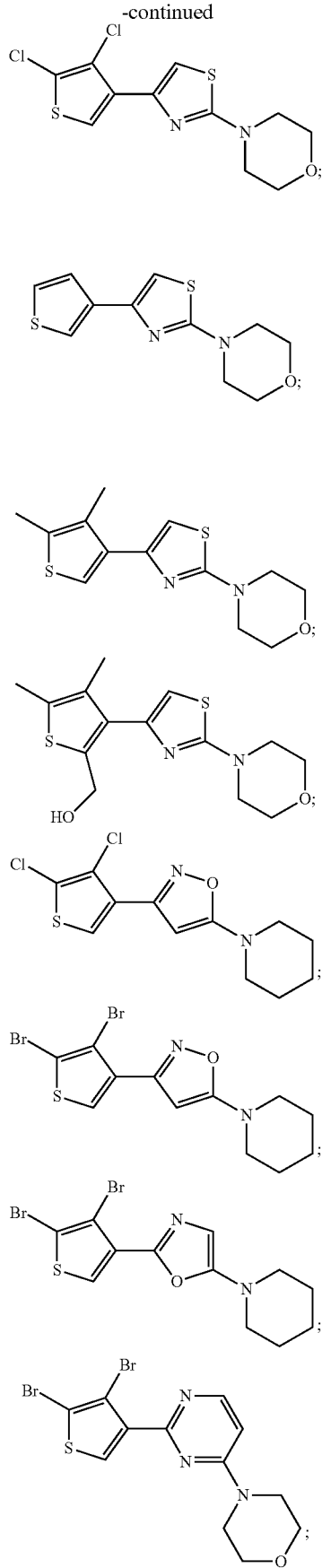

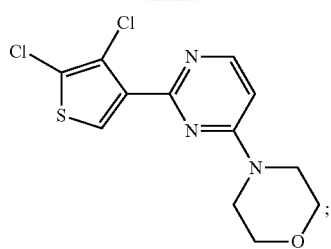
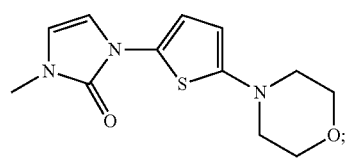
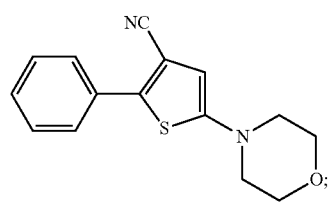
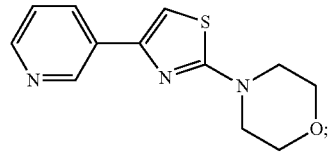
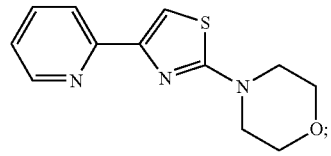
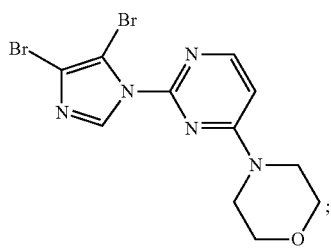
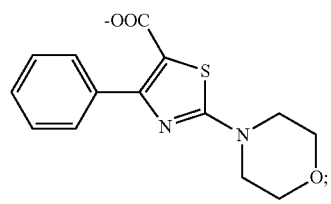
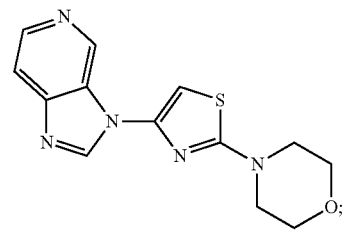
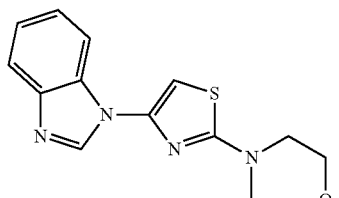
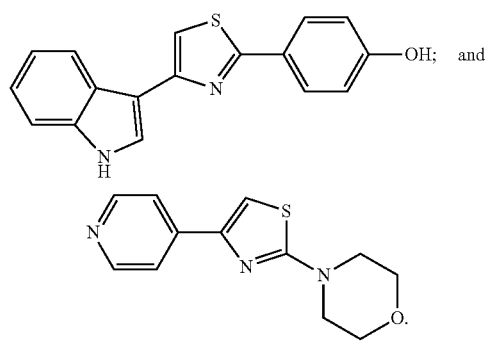
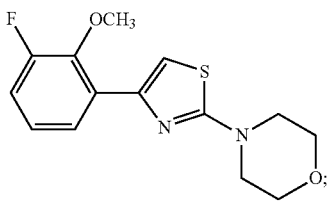
The compound may be selected from one or more of the following compounds:
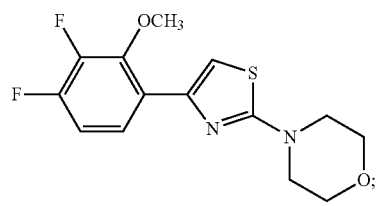
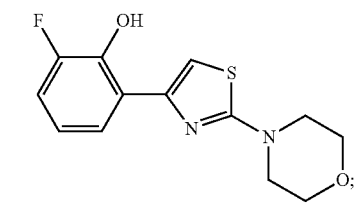
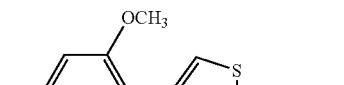
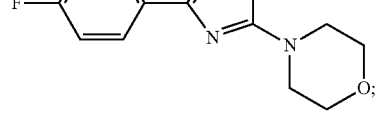
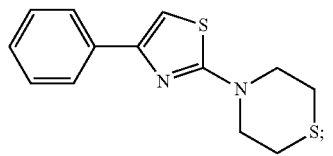

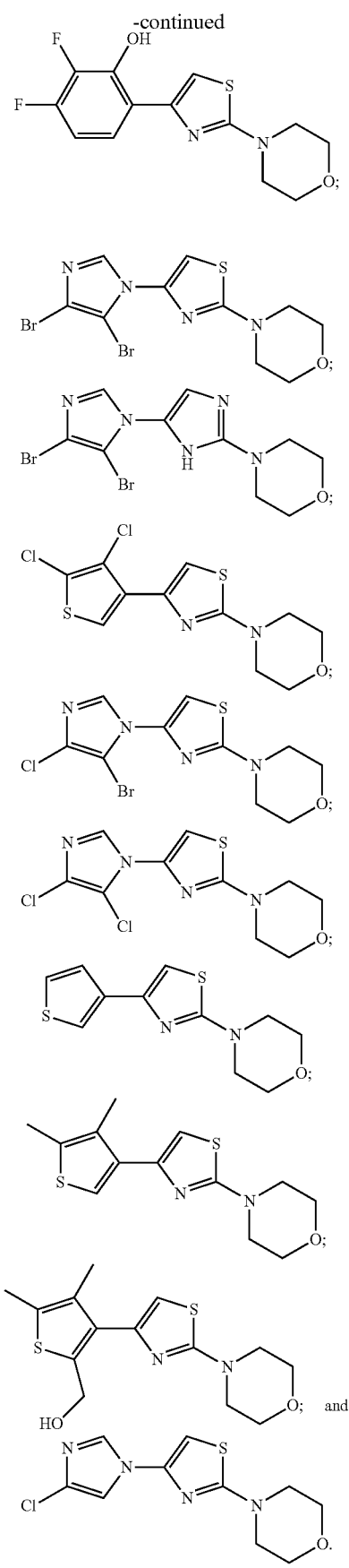
The compound may be selected from one or more of the following:
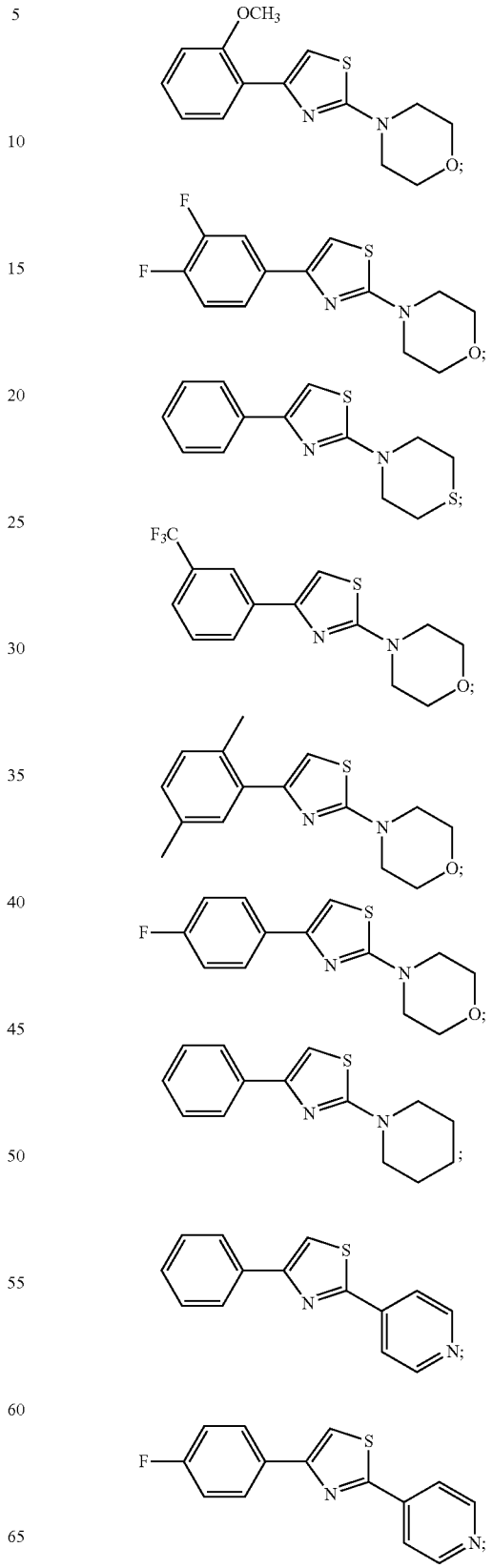

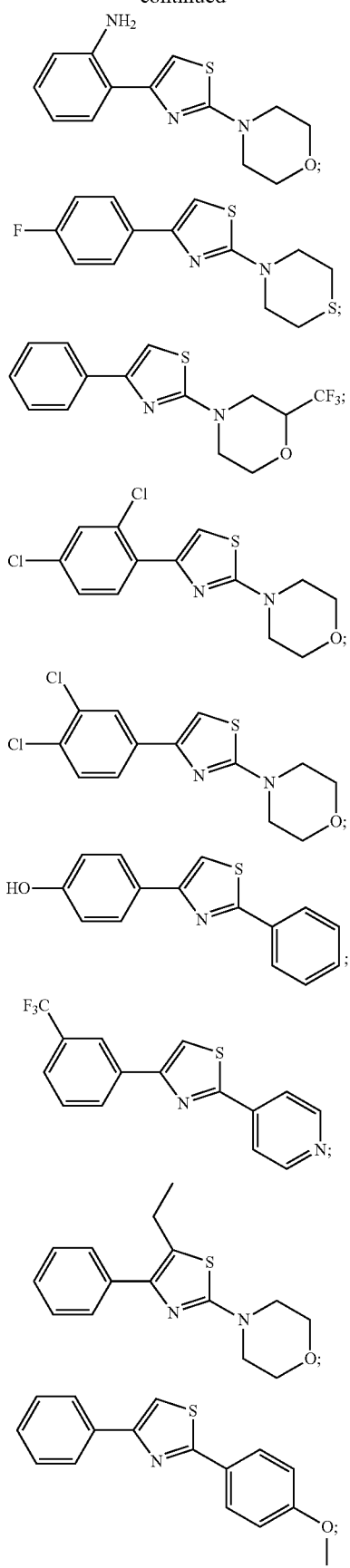
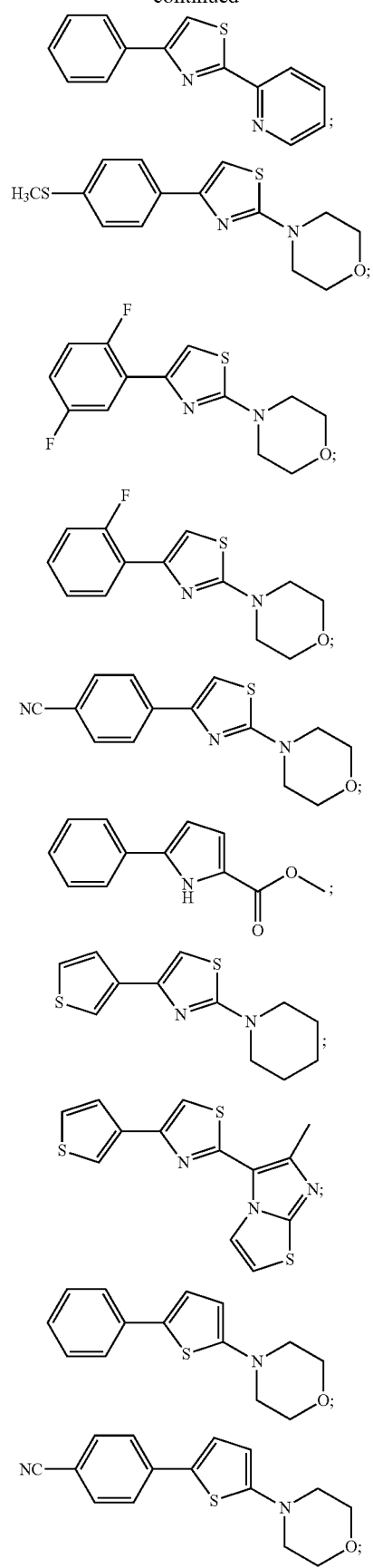

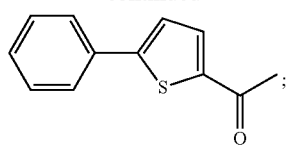
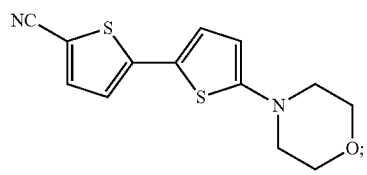
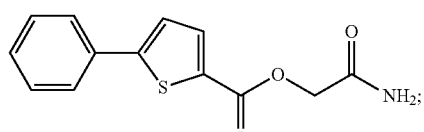
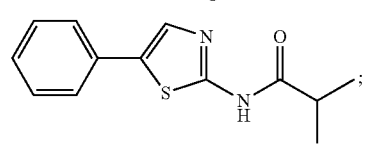
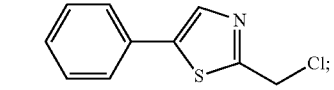
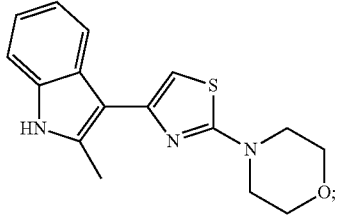
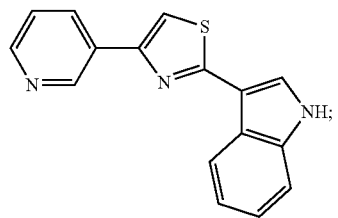
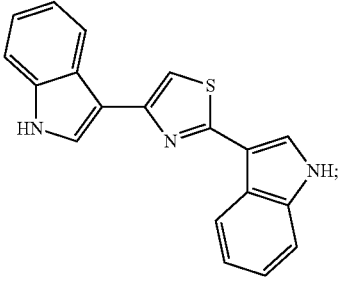
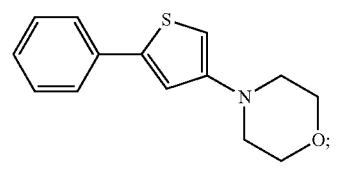
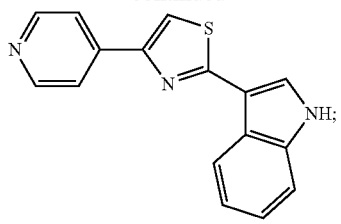
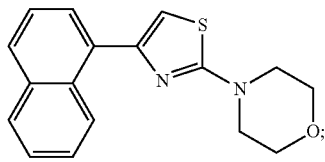
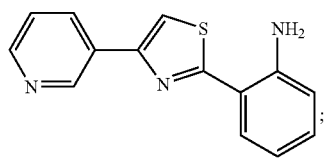
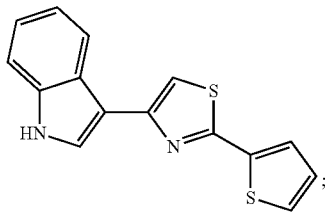
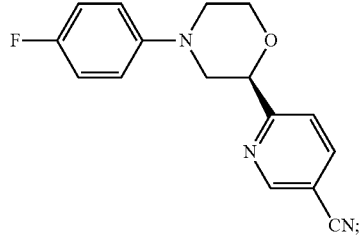
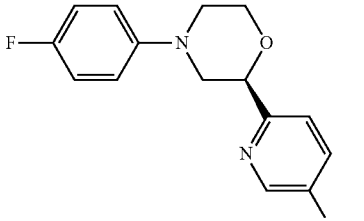
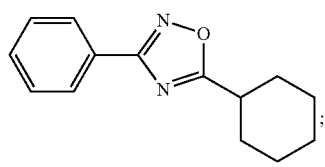
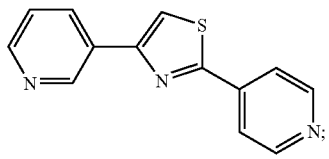

-continued
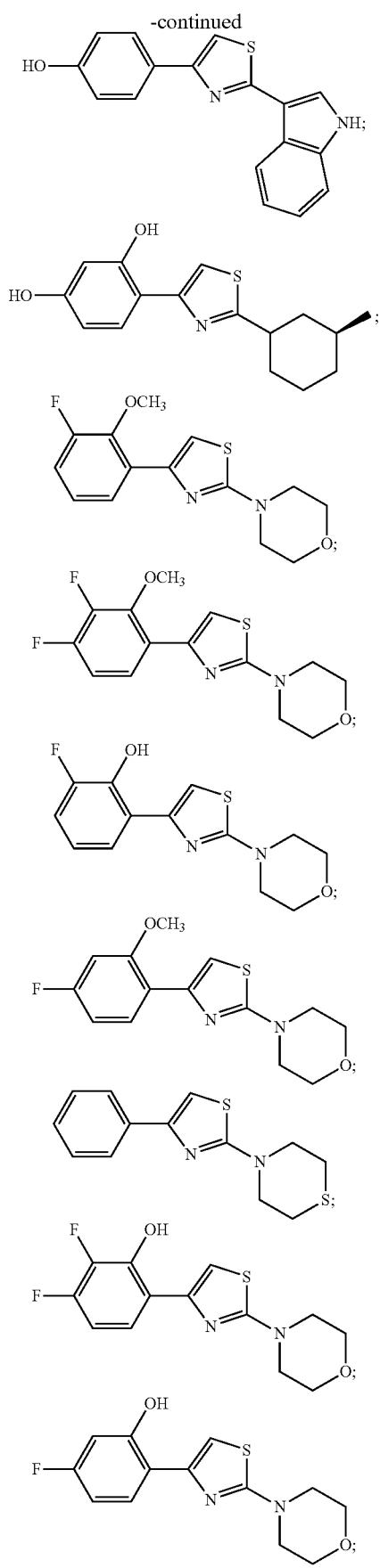
-continued
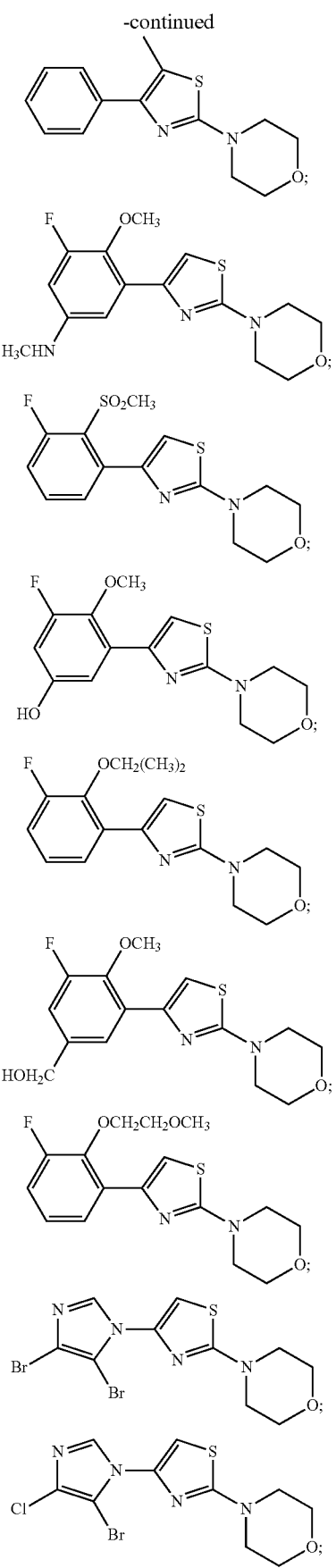

-continued
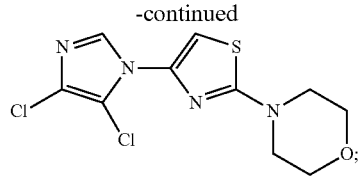
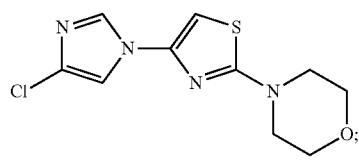
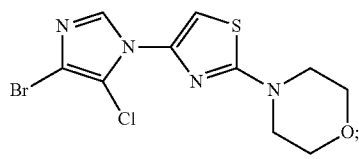
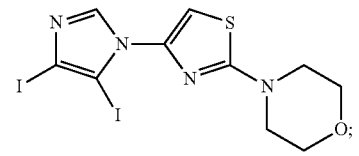
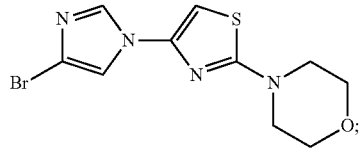
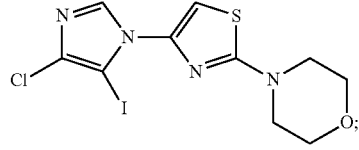
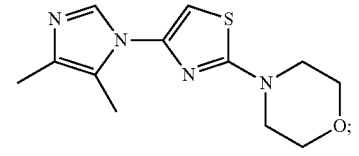
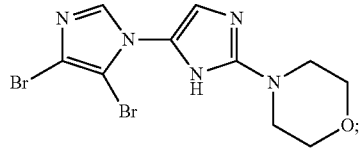
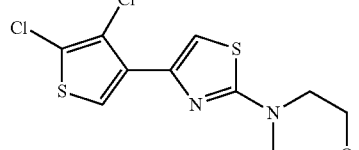
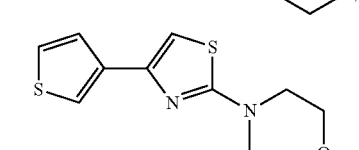
-continued
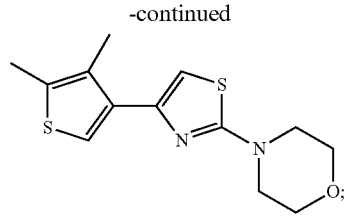
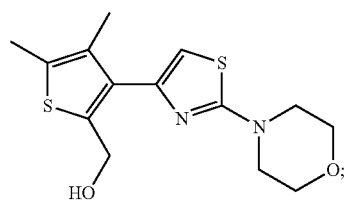
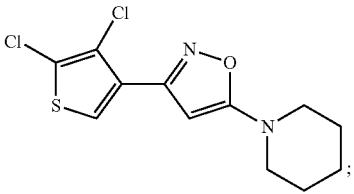
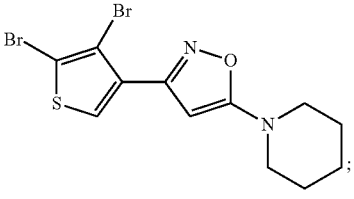
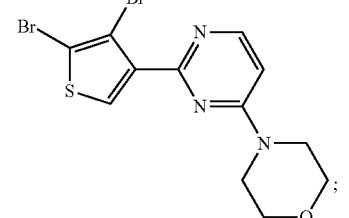
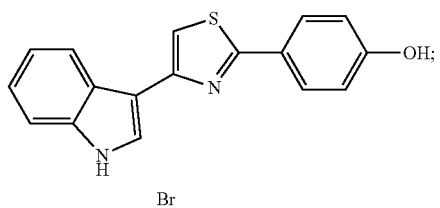
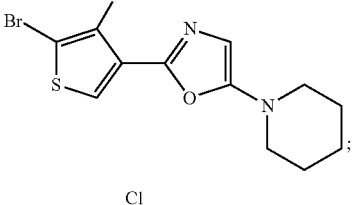
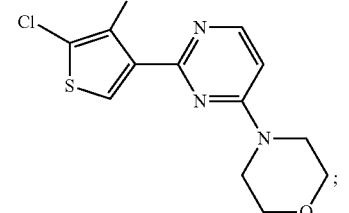

-continued

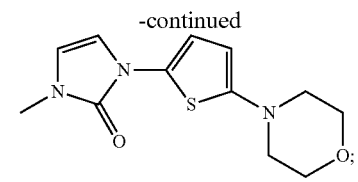

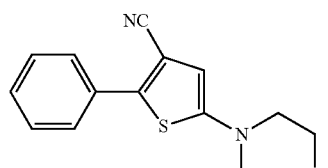

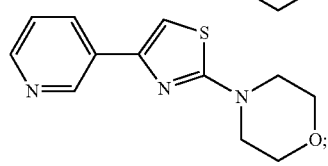

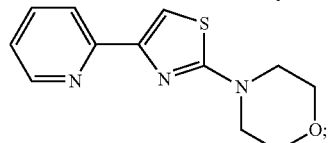

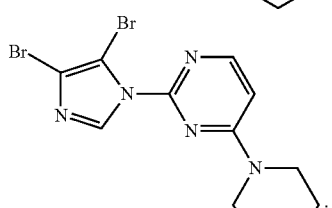

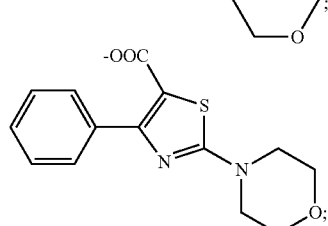

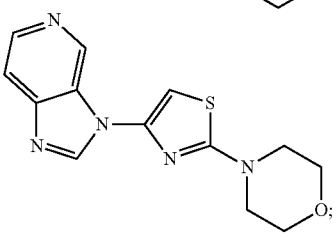

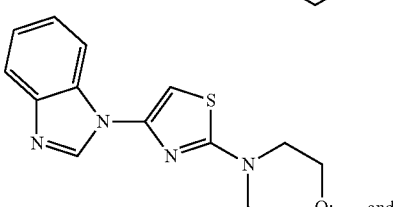 and

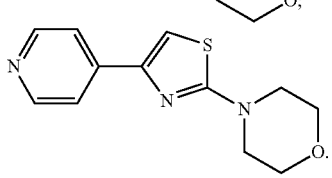

The modulating AR activity may be for treatment of at least one indication selected from the group consisting of: cancer, hair loss, acne, hirsutism, ovarian cysts, polycystic ovary disease, precocious puberty, and age related macular degeneration. The cancer may be AR-mediated cancer. The cancer may be selected from the group including of: prostate cancer, breast cancer, ovarian cancer, endometrial cancer and bladder cancer. The cancer may be Taxene resistant triple negative breast cancer.

In accordance with one embodiment, there is provided a use of a compound or pharmaceutically acceptable salt thereof having a structure of selected from TABLE 1 or described in the claims.

In accordance with another embodiment, there is provided a use of a compound or pharmaceutically acceptable salt thereof having a structure selected from TABLE 1 or described in the claims.

In accordance with another embodiment, there is provided a pharmaceutical composition comprising a compound or pharmaceutically acceptable salt thereof as set out herein and a pharmaceutically acceptable excipient.

In accordance with another embodiment, there is provided a method for modulating AR activity, the method comprising administering to a mammalian cell a compound or pharmaceutically acceptable salt thereof as set out herein.

In accordance with another embodiment, there is provided a pharmaceutical composition for modulating androgen receptor (AR) activity, comprising a compound as described herein and a pharmaceutically acceptable carrier.

In accordance with another embodiment, there is provided a commercial package comprising (a) compound described herein or a pharmaceutical composition described herein; and (b) instructions for the use thereof for modulating androgen receptor (AR) activity.

The modulating AR activity may be for treatment of at least one indication selected from the group consisting of: cancer, hair loss, acne, hirsutism, ovarian cysts, polycystic ovary disease, precocious puberty, and age related macular degeneration. The cancer may be AR-mediated cancer. The cancer may be selected from the group consisting of: prostate cancer, breast cancer, ovarian cancer, endometrial cancer and bladder cancer. The cancer may be Taxene resistant triple negative breast cancer. The modulating AR activity may be for treatment of prostate cancer.

The mammalian cell may be a human cell. The cell may be a prostate cell. The cell may be a prostate cancer cell.

In accordance with another embodiment, there is provided a compound having the structure selected from TABLE 1 or described in the claims.

The compound may be for modulating androgen receptor (AR) activity. The modulating androgen receptor (AR) activity may be for treatment of at least one indication selected from the group consisting of: prostate cancer, breast cancer, ovarian cancer, endometrial cancer, hair loss, acne, hirsutism, ovarian cysts, polycystic ovary disease, precocious puberty, and age-related macular degeneration. The modulating AR activity may be for treatment of at least one indication selected from the group consisting of: cancer, hair loss, acne, hirsutism, ovarian cysts, polycystic ovary disease, precocious puberty, and age related macular degeneration. The cancer may be AR-mediated cancer. The cancer may be selected from the group consisting of: prostate cancer, breast cancer, ovarian cancer, endometrial cancer and bladder cancer. The cancer may be Taxene resistant triple negative breast cancer. The modulating AR activity may be for the treatment of prostate cancer.

DETAILED DESCRIPTION

Figure 1:
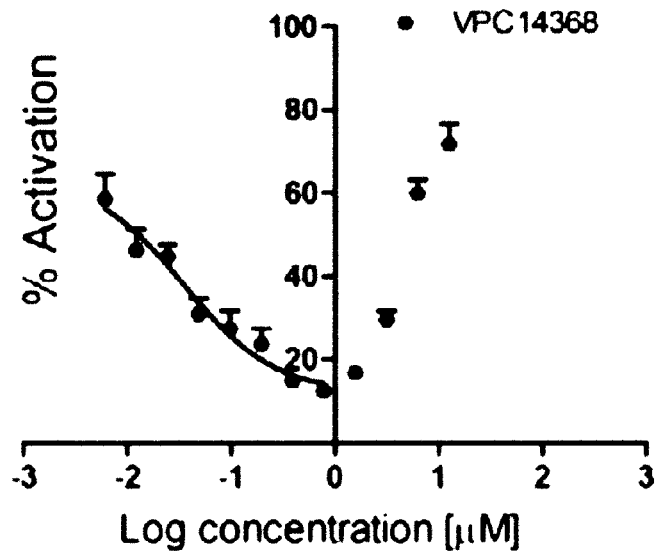
FIG. 1 shows dose-response curves (0-12.5 µM) illustrating the inhibition of the AR transcriptional activity in LNCaP cells by 14368 using eGFP (A) and PSA (B) assays in the presence of R1881. (C) Activation of AR transcription in LNCaP cells by 14368 in the absence of R1881. The value 1 corresponds to the eGFP signal from LNCAP cells stimulated with 0.1 nM R1881. Luciferase reporter assay showing AR transcriptional activity in PC3 cells transiently transfected with either WT-AR (D) or T877A-AR mutant (E). The cells were treated with either 14368 or Enzalutamide (Enz) in the presence or absence of R1881 stimulation. Data points represent the mean of three independent experiments±SEM. 100% refers to luminescence recorded in 0.1% DMSO only. (F) Inhibition of endogenous wild type AR in R1-AD1 Cells by 14368 and Bicalutamide (Bic) in the presence of 0.1 nM R1881.
Figure 1:
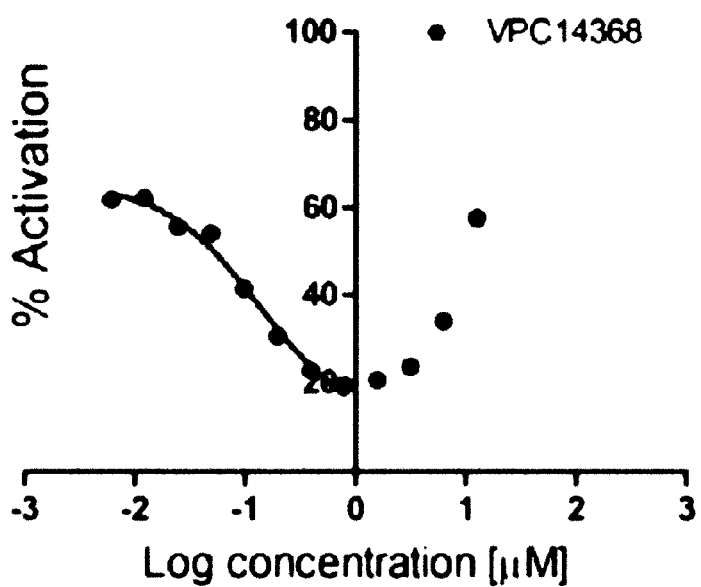
Figure 1:
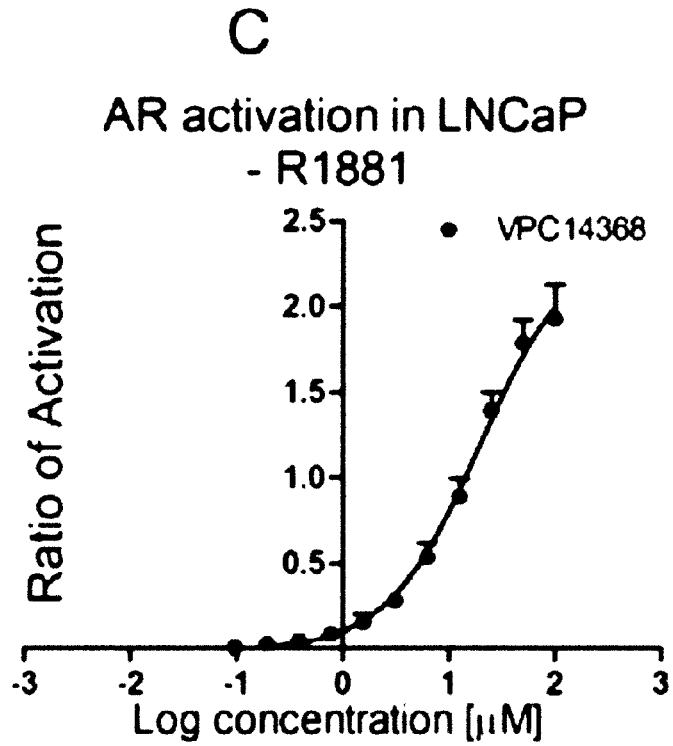
Figure 1:
Figure 1:
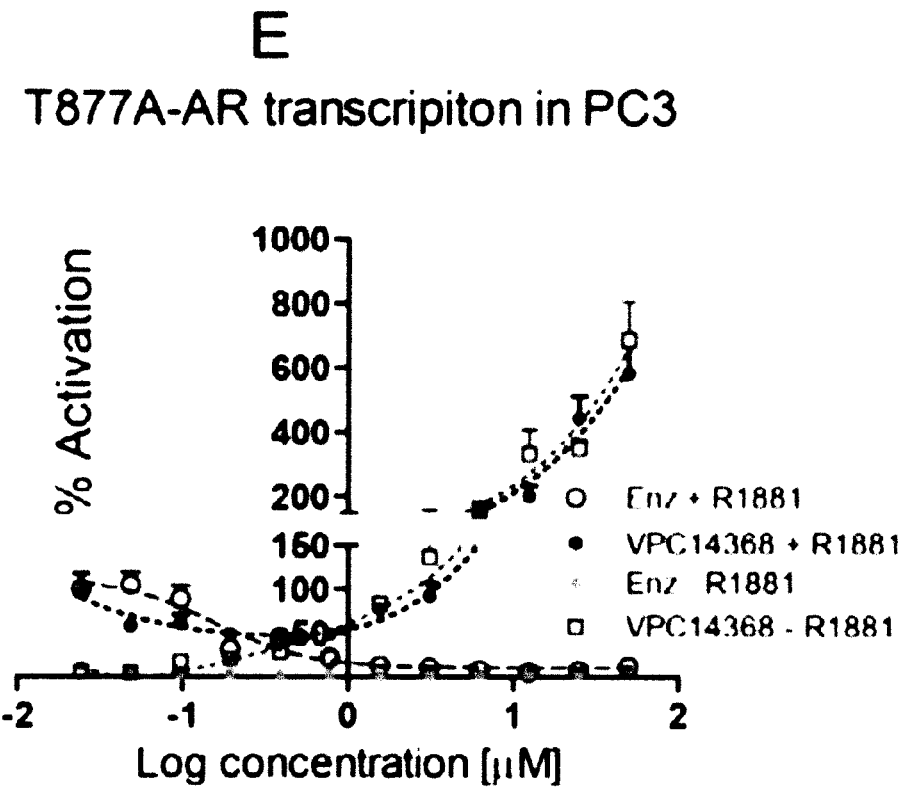
Figure 1:

The DNA-binding domain is an attractive target for inhibition of AR dimerization and/or DNA binding. In silico computational drug discovery methods were used to conduct a virtual screen of >3 million purchasable lead-like compounds from the ZINC database (Irwin, J. et al. Abstracts of Papers Am. Chem. Soc. (2005) 230:U1009) to identify potential DBD binders. The in silico methods included large-scale docking, in-site rescoring and consensus voting procedures.

It will be understood by a person of skill that COOH and $NR_2$ may include the corresponding ions, for example carboxylate ions and ammonium ions, respectively. Alternatively, where the ions are shown, a person of skill in the art will appreciate that the counter ion may also be present. Furthermore, it will be appreciated by a person of skill that other moieties may include the corresponding ions, and where the ions are shown, a person of skill in the art will appreciate that the counter ion may also be present.

TABLE 1 shows the compounds tested by structure (series 1-6) and the associated identifiers. TABLE 1 also provides additional generic structures identifying compounds within the scope of the present invention. The shaded compounds are novel synthetic compounds and unshaded compounds were known ZINC compounds. Furthermore, where the % inhibition, eGFP $IC_{50}$ or the PSA $IC_{50}$ has no value given, this may be because no measurement was taken or the value was not calculated, in the case of the % inhibition. Accordingly, no value given in TABLE 1 does not mean that there was no activity. Furthermore, a zero value For those 9 new compounds (14502-14510), a single concentration screen was not performed, as done with the other compounds. Instead, IC50 was measured directly using multiple concentrations, and for these inactive compounds, the dose-response curves were flat, showing almost 0% inhibition at all concentrations.

For the other compounds, a single dose screen for most of them was done, while the IC50 was only measured for those with a high percentage of inhibition, except a few interesting ones with relatively low % inhibition. As the % inhibition was measured at a concentration of 3 µM or 1 µM, the threshold by % inhibition for actives and inactives was low as you said. It was found that an inhibition of about 30% at 3 µM may give IC50 around 50 µM. Accordingly, generally a compound having an inhibition value lower than 30% may be considered inactive. Nevertheless, activity of a compound should not always be determined by % inhibition. In fact any compounds that were tested and considered as inactive may have been considered active if the sensitivity of the system were somewhat reduced. As compounds became better and better the level of sensitivity was increased. Accordingly, it became more difficult to measure low activity compounds in the assay system. However, since the newer compounds are based on previously successful compounds they may have some activity at some level. Accordingly, "inactive" may be an incorrect term, and "none detected" may be more appropriate.

TABLE 1
DBD Binding Compounds
Series 1
where A is 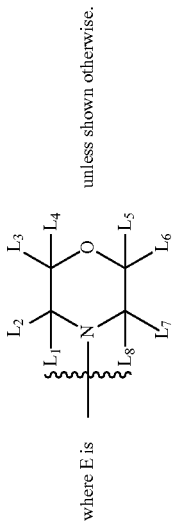 unless shown otherwise;
where D is (thiazole structure) unless shown otherwise; and
where E is (morpholine structure) unless shown otherwise.
| ID | R₁ | A | | | | | D | E | | | | | % Inhibition (3 μM) | eGFP IC₅₀ (μM) | PSA IC₅₀ (μM) |
|---|---|---|---|---|---|---|---|---|---|---|---|---|---|---|---|
| | | R₂ | R₃ | R₄ | R₅ | | J₁ | L₁₋₂ | L₃₋₄ | L₅₋₆ | L₇₋₈ | | | | |
| 14368 | OCH₃ | F | H | H | H | | H | H | H | H | H | | | 0.03 | 0.13 |
| 14500 | | | | | | | 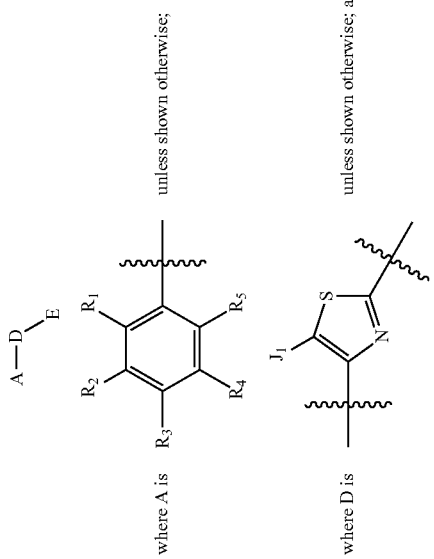 | | | | | | | 0.05 | |

TABLE 1-continued
DBD Binding Compounds
| ID | Structure | | | | | | | | | |
|---|---|---|---|---|---|---|---|---|---|---|
| 14462 | 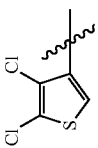 | | | | H | | H | H | | 0.11 |
| 14449 | 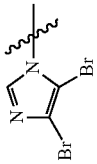 | | | | | H | H | H | 0.10 (±0.05) | 0.17 |
| 14370 | | OCH₃ | H | H | F | H | H | H | 0.19 | 0.25 |
| 14257 | | OCH₃ | H | H | H | H | H | H | 0.22 | 0.83 |
| 14264 | | H | H | H | F | H | H | H | 0.24 | 0.11 |
| 14404 |  | | | | | H | H | H | 0.26 | 0.22 |
| 14365 | | OH | H | H | H | H | H | H | 0.27 | 0.16 |
| 14367 | | OCH₃ | H | H | F | H | H | H | 0.3 | 0.23 |
| 14228 | | H | H | H | H | H | H | H | 0.33 | 0.28 |
| 14451 |  | | | | | H | H | H | 0.33 | 0.44 |
| 14466 |  | | | | | | H | H | 0.40 | |
| 14408 | 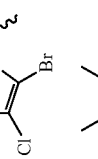 | | | | | H | H | H | 0.42 | 0.43 |
| 14103 | H | H | H | H | 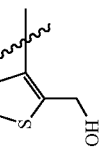 | H | H | H | 0.522 | 0.511 |
Row 14103 also shows: 100.00 (an additional data value) and row 14365/14367/14228 show 97.36/103.35/109.99; rows 14370/14257/14264 show 106.81/117.54/115.37.

TABLE 1-continued
DBD Binding Compounds
| | | | | | | | | | | |
|---|---|---|---|---|---|---|---|---|---|---|
| 14385 | H | H | H | H | H |  | H | | 0.6 | |
| 14292<br>14293 | H<br>CH₃ | CF₃<br>H | H<br>CH₃ | H<br>H | H<br>H | H<br>H | H<br>H | | 0.61<br>0.62 | 0.58<br>0.52 |
| 14402 | |  | H | H | H | H | H | | 0.66 | 0.57 |
| 14255<br>14371 | H<br>OH | H<br>F | H<br>F | H<br>H | H<br>H | H<br>H | 44.9<br>98.92 | 0.66<br>0.8 | 0.41<br>0.7 |
| 14131 | |  | | H |  | H | 116.83 | 0.82 | 0.54 |
| 14448 | |  | | H | H | H | | 0.96 | 0.72 |
| 14471 | |  | | H |  | H | | 1.015 | 1.411 |
| 14233 | H | H | H | H |  | H | | 1.02 | 0.69 |
| 14497 | |  | |  | H | H | | 1.06 | |

TABLE 1-continued

DBD Binding Compounds

| ID | R1 | R2 | R3 | R4 | R5 | R6 | R7 | Val1 | Val2 | Val3 |
|---|---|---|---|---|---|---|---|---|---|---|
| 14509 | H | [benzimidazolyl] | H | H | H | H | H | | 1.17 | |
| 14352 | H | H | H | H | H | H | H | | 1.19 | 0.63 |
| 14315 | H | F | H | H | H | H | H | | 1.194 | 0.632 |
| 14364 | OH | F | H | H | [thiophene-2,5-diyl] | H | H | 83.28 | 1.22 | 0.81 |
| 14138 | H | F | H | H | H | H | H | 91.26 | 1.237 | 0.837 |
| 14450 | | [4-Br,5-Cl-imidazolyl] | H | H | H | H | H | 110.53 | 1.30 | 1.28 |
| 14273 | NH₂ | H | H | H | H | H | H | 73.42 | 1.41 | 2.03 |
| 14117 | H | CN | H | H | [thiophene-2,5-diyl] | H | H | 111.35 | 1.429 | 0.885 |
| 14150 | | [4-pyridyl] | H | H | H | H | H | 133 | 1.44 | 1.29 |
| 14349 | H | H | H | CH₃ | H | [3-indolyl] | H | | 1.47 | |

TABLE 1-continued
DBD Binding Compounds
| ID | | | | | | | | | | |
|---|---|---|---|---|---|---|---|---|---|---|
| 14464 | | | | 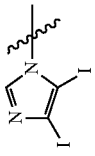 | H | H | H | | 1.50 | 1.81 |
| 14501 | | | | 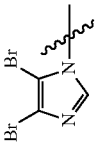 | H | 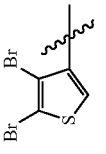 | H | | 1.5 | 0.88 |
| 14499 | | | |  | H |  | H | | 1.5 | 0.88 |
| 14230 | | | | 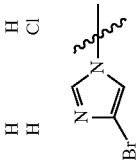 | H | H | H | 99.47 | 1.61 | |
| 14386 | | H | H | F | H | H | H | | 1.6 | |
| 14250 14263 | H Cl | H H | H H | H Cl | H H | H H | H H | | 1.64 1.66 | 0.16 1.32 |
| 14447 | | | |  | H | CF₃ H | H | | 2.10 | 1.74 |
| 14481 | | | |  | H |  | H | 80.47 | 2.18 | 1.41 |
| 14422 | | H | H |  | H | | H | 130.65 | 2.26 | |

TABLE 1-continued

DBD Binding Compounds

| ID | R1 | R2 | R3 | R4 | R5 | R6 | Val1 | Val2 |
|---|---|---|---|---|---|---|---|---|
| 14463 | 3-pyridyl | H | | H | 2-aminophenyl | | 2.3 | 2.12 |
| 14468 | 4-chloro-5-iodo-imidazolyl | | | | H | | 2.44 | 4.02 |
| 14436 | 2-pyridyl | | | | H | | 2.51 | |
| 14435 | 4-pyridyl | F | H | H | H | | 2.61 | |
| 14125 | imidazo[4,5-c]pyridyl | | morpholinyl | | 5-cyano-2-pyridyl | 76.41 | 2.63 | 2.81 |
| 14508 | | F | H | H | H | | 2.8 | |
| 14123 | | | morpholinyl | | 5-nitro-2-pyridyl | 78.39 | 2.84 | 3.19 |
| 14149 | 4-pyridyl | | isoxazolyl | | cyclohexyl | 86.2 | 2.97 | |
| 14465 | OCH3 | NHCH3 | H | H | H | 82.19 | 3.06 | 2.96 |
| 14266 | H | H | H | Cl | H | | 3.31 | |
| 14429 | SO2CH3 | H | H | F | H | | 3.55 | |

TABLE 1-continued

DBD Binding Compounds

| ID | | | | | | | | | | | |
|---|---|---|---|---|---|---|---|---|---|---|---|
| 14399 | OCH₃ | [4,5-dimethyl-imidazol-1-yl] | H | H | H | H | H | | 3.65 | 2.42 |
| 14467 | OCH₃ | H | F | H | H | H | H | | 3.7 | |
| 14420 | H | H | OH | H | H | H | H | | 3.73 | |
| 14421 | H | CF₃ | H | H | H | H | H | 125 | 4.61 | |
| 14430 | OCH(CH₃)₂ | H | F | H | H | H | H | 106.63 | 5.27 | |
| 14442 | H | [pyridin-3-yl] | H | H | [pyridin-4-yl-C(CH₃)₂-] | H | H | 105.89 | 5.39 | 3.05 |
| 14285 | H | H | H | H | [indol-3-yl-C(CH₃)₂-] | C₂H₅ | H | 86.27 | 5.85 | 8.43 |
| 14419 | H | H | H | H | H | H | H | 119.36 | 6.11 | |
| 14432 | H | [3-methyl-2-oxo-imidazol-1-yl] | | [thiophene-2,5-diyl] | H | H | | 6.30 | |
| 14135 | H | [2-methyl-indol-3-yl] | | H | [4-methoxyphenyl-C(CH₃)₂-] | H | H | 64 | 6.89 | 7.8 |
| 14506 | H | H | H | H | H | COO⁻ | H | | 7.0 | 4.5 |

TABLE 1-continued
DBD Binding Compounds
| | | | | | | | | |
|---|---|---|---|---|---|---|---|---|
| 14130 | H | H | H | H |  | H |  | 7.4 8.54 |
| 14498 | | | | | | | | 8.65 10.45 |
| 14297 14262 14455 | H F OCH₃ | SCH₃ H H | H F CH₂OH | H H H | H H H | H H H | H H H | 109.99 96.6 90 |
| 14423 | H |  | H | H | H | H |  | 89.02 |
| 14286 | F | F | H | H |  | H | H | 85.86 |
| 14426 | H | H | H | H | | H |  | 81.25 |
| 14439 | |  | | | H | | H | 81.00 |
| 14457 | H | CN | H | H |  | H | H | 80 |
| 14425 | H | H | H | H | | H | H | 79.48 |
| 14424 | H | H | H | H |  | H | H | 78.13 |
| 14431 | O(CH₂)₂OCH₃ | F | H | H | | H | H | 76.56 |

TABLE 1-continued

DBD Binding Compounds

| | | | | | | |
|---|---|---|---|---|---|---|
| 14494 | [2,3-dichlorothiophene] | | | [pyrimidine] | [pyridine] | H | 72.66 |
| 14493 | [pyridine] | | H | H | H | H | 68.95 |
| 14444 | —OH | | H | H | [indole] | H | 67.77 |
| 14491 | [2,3-dibromothiophene] | | | [oxazole] | H | H | 65.07 |
| 14366 | H | OH | H | [cyanothiophene] | H | H | 60.9 |
| 14301 | OH | OH | | | H | H | 60 |
| 14133 | [thiophene] | | | | [piperidine] | H | 53.01 5 |
| 14114 | [cyanothiophene] | | | H | [imidazothiazole] | H | 52.98 |
| 14277 | SO$_2$CH$_3$ | H | H | [thiophene] | H | H | 12.71 11.41 |

TABLE 1-continued

DBD Binding Compounds

| # | R1 | R2 | R3 | R4 | R5 | R6 | R7 | Val1 | Val2 |
|---|---|---|---|---|---|---|---|---|---|
| 14427 | H | H | H | H | [thiazolyl] | [—C(O)NH—CH(CH3)C2H5] | | | 13.34 |
| 14428 | H | H | H | H | [thiazolyl] | [—C(O)NH—(thiane)] | | | 15.45 |
| 14254 | H | H | H | NO2 | H | H | | 3.37 | 15.8 |
| 14410 | H | H | H | [N-methylpyrrolyl] | H | H | | | 28.41 |
| 14253 | H | H | H | Cl | H | H | H | 38.17 | 39.86 |
| 14251 | H | H | H | Br | H | H | H | 7.96 | |
| 14252 | H | H | H | OCH3 | OCH3 | H | H | 26.03 | |
| 14249 | H | H | H | OCH3 | H | H | H | 45.16 | |
| 14256 | H | H | H | NH2 | H | H | H | 28.14 | |
| 14261 | H | H | H | CN | H | H | H | 25.48 | |
| 14288 | H | H | Cl | OCH3 | Cl | H | H | 35.89 | |
| 14259 | H | H | H | C2H5 | H | H | H | 26.26 | |
| 14276 | H | H | CH3 | NHSO2CH3 | H | H | H | 25.98 | |
| 14294 | H | CH3 | H | CH3 | H | H | H | 40.03 | |
| 14283 | H | OH | H | CH3 | H | H | H | 38.89 | |
| 14295 | H | OCH3 | H | OH | H | H | H | 24.7 | |
| 14268 | H | Cl | H | OCH3 | H | H | H | 37.55 | |
| 14437 | H | H | OH | H | H | H | H | 45.04 | |
| 14247 | H | H | H | OH | H | H | H | 19.95 | 10.31 |
| 14267 | H | H | H | NO2 | H | H | H | 3.73 | |
| 14248 | H | H | H | Cl | H | CH3 | CH3 | 4.73 | |
| 14284 | H | H | H | CH3 | H | CH3 | CH3 | 30.22 | |
| 14274 | H | H | H | H | H | H | H | 5.04 | |
| 14469 | F | H | H | H | H | [oxazolyl-CN] | CH3 CH3 | 42.4 | |

TABLE 1-continued

DBD Binding Compounds

| ID | | | | | | | | | |
|---|---|---|---|---|---|---|---|---|---|
| 14475 | Cl | H | H | H | ![maleimide-Cl] | H | H | H | 8.89 |
| 14476 | H | H | H | H | ![maleimide-Cl] | H | H | H | 9.79 |
| 14231 | | | ![naphthyl] | H | H | H | H | H | 38.78 |
| 14291 | | | ![tetrahydronaphthyl] | H | H | H | H | H | 18.64 |
| 14403 | | | ![cyclopentyl] | H | H | H | H | H | 22.00 |
| 14136 | | | ![benzofuran] | H | H | H | H | H | 40.98 |
| 14137 | | | ![benzothiazole] | H | H | H | H | H | 37.44 |
| 14282 | | | ![dihydrobenzofuran] | H | H | H | H | H | 29.04 |
| 14406 | | | ![cyclohexyl] | H | H | H | H | H | 33 |

TABLE 1-continued
DBD Binding Compounds
| | | | | | | |
|---|---|---|---|---|---|---|
| 14446 | 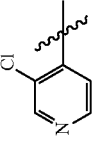 | H | H | H | H | 24 |
| 14407 | 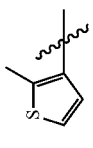 | H | H | H | H | 38.00 |
| 14411 | 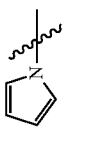 | H | H | H | H | 44.00 |
| 14479 | 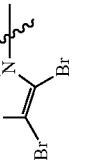 | H | H | CH₃ | CH₃ | 20.5 |
| 14496 | 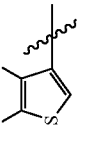 | 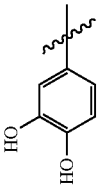 | H | CH₃ | H | |
| 14445 | 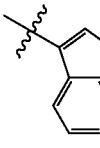 | H | H | H | H | 20 |
| | | | | | | 8.42 |
| 14470 | 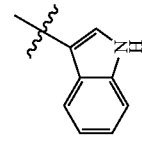 | H | H | | H | 13 |
| 14477 | | H | H | | H | 46.58 |

TABLE 1-continued

DBD Binding Compounds

| # | R | R' | R'' | Ar | Value |
|---|---|---|---|---|---|
| 14478 | H | indol-3-yl | CH₃ | pyridin-4-yl | 40.63 |
| 14480 | OCH₃ | indol-3-yl | H | 2-methoxyphenyl | 29.98 |
| 14484 | H | indol-3-yl | H | 3-fluorophenyl | 20.05 |
| 14485 | H | indol-3-yl | H | phenyl | 21.9 |
| 14341 / 14363 | H | F, H, H, H | CH₃, CH₃ | H, H, H, H, H | 43.7 / 29.03 |
| 14338 | H | H, H, H, H | H | 4-methylpiperazin-1-yl | 19.33 |
| 14340 | H | F, H, H, H | H | piperazin-1-yl | 16.12 |
| 14351 | H | H, H, H, H | H | pyrrolidin-1-yl | 38.4 |

TABLE 1-continued

DBD Binding Compounds

| # | | | | | | |
|---|---|---|---|---|---|---|
| 14361 | H | H | H | H | H | indol-3-yl | 41.63 / 10.14 |
| 14357 | H | H | H | F | isoxazolyl | pyridin-4-yl | 43.67 |
| 14359 | H | H | F | H | isoxazolyl | pyridin-4-yl | 9.69 |
| 14353 | H | F | H | H | morpholinyl | pyridin-2-yl | 18.26 |
| 14443 | H | H | OCH₃ | H | H | indol-3-yl | 25.15 |
| 14343 | H | OCH₃ | H | H | H | pyridin-2-yl | 16.12 |
| 14486 | H | CF3 | H | H | H | pyrazinyl | 20.4 |
| 14104 | H | H | F | H | thiohydantoinyl | phenyl | 43.01 |

TABLE 1-continued

DBD Binding Compounds

| # | | | | | | |
|---|---|---|---|---|---|---|
| 14317 | H | H | CH₃ | H | (imidazolidine-dione) | 44.73 |
| 14105 | H | H | H | H | (thiohydantoin) | 43.84 |
| 14106 | H | H | H | H | (hydantoin-CH₂-NH) | 9.33 |
| 14139 | H | H | OCH₃ | H | (thiohydantoin) | 41 |
| 14140 | H | H | H | H | (thiohydantoin) | 40.16 |
| 14107 | H | Cl | H | H | (aminopyrrolidinone) | 15.07 |
| 14108 | H | H | CH₃ | H | (oxadiazole) | 25.37 |
| 14322 | H | H | H | H | (isoxazole) | 22.26 |

TABLE 1-continued

DBD Binding Compounds

| | | | | | | |
|---|---|---|---|---|---|---|
| 14143 | H | H | H | H | H | [3,5-isoxazole] | [4-pyridyl] 55.92 |
| 14144 | H | H | H | H | H | [3,5-isoxazole] | [2-pyridyl] 39.87 |
| 14145 | H | H | H | H | H | [3,5-oxadiazole] | [2-pyridyl] 49.01 |
| 14146 | H | H | H | H | H | [3,5-oxadiazole] | [2-pyridyl] 38.64 |
| 14109 | H | H | H | H | H | [triazole] | [3-pyridyl] 20.15 |
| 14111 | H | H | H | H | H | [oxazoline] | [2-thienyl] 18.08 |
| 14113 | H | H | $NO_2$ | H | H | [thiophene-ketone] | H 22.09 |
| 14118 | H | H | $CH_3$ | H | H | [thiophene-ketone] | H 29.14 |

TABLE 1-continued

DBD Binding Compounds

| | | | | | | | |
|---|---|---|---|---|---|---|---|
| 14119 | H | H | H | H | 5-acyl-thiophene | H | 39.02 |
| 14120 | H | H | Cl | H | 5-acyl-thiophene | H | 39.58 |
| 14339 | H | H | H | H | H | N-piperazine-CONH₂ | 15.82 |
| 14121 | H | H | H₃COOC-(5-methylthiophene) | H | thiophene | H | 36.53 |
| 14122 | H | H | CH₃ | H | thiazoline | H | 22.8 |
| 14127 | H | H | H | H | methyl-morpholine | 3-chloro-pyridine-carboxamide | 30.6 |
| 14132 | H | thiophene | H | | | pyridine | 73.52 |

TABLE 1-continued

DBD Binding Compounds

| # | | | | | | |
|---|---|---|---|---|---|---|
| 14328 | H | thiophen-2-yl | H | H | 3-pyridyl | 55.63 |
| 14488 | Cl | 2-methyl-imidazol-4-yl | H | H | 4-pyridyl | 9.61 |
| 14258 | OCH₃ | OCH₃ | OCH₃ | H | H | 0 |
| 14438 | | Cl | H | H | H | 0 |
| 14298 | | NO₂ | H | H | H | 0 |
| 14456 | | F | (CH₂)₂OH | H | H | 0 |
| 14396 | H | H | H | pyridazine-3,6-diyl | H | 0 |
| 14472 | H | Cl | H | 3-chloro-maleimidyl | N-methylpiperazinyl | 0 |
| 14473 | CH₃ | H | H | 3-chloro-maleimidyl | H | 0 |
| 14474 | H | Cl | H | 3-chloro-maleimidyl | H | 1.9 |
| 14482 | F | H | H | 3-chloro-maleimidyl | H | 0 |

TABLE 1-continued

DBD Binding Compounds

| ID | | | | | | | | |
|---|---|---|---|---|---|---|---|---|
| 14492 | Cl | Cl | H | H | ![maleimide-Cl] | H | H | 0 |
| 14441 | | | H | H | ![dichloropyridine] | H | H | 0 |
| 14405 | | | H | H | ![methylthiophene] | H | H | 0 |
| 14483 | | | H | H | ![pyridine] | H | H | 0 |
| 14116 | | | H | NO$_2$ | H | ![thiophene] | ![imidazole-NH] | 0 |
| 14350 | | | OH | H | H | CH$_3$ | H | 2.07 |
| 14354 | | | H | H | H | H | H | 0 |
| 14358 | | | H | H | H | ![isoxazole] | ![piperazine-NH] | 0.28 |
| 14318 | | | H | F | H | ![pyrazole-OH] | ![pyridine] | 0 |

TABLE 1-continued

DBD Binding Compounds

| ID | | | | | | | |
|---|---|---|---|---|---|---|---|
| 14319 | H | H | CH₃ | H | [dimethylpyrazole-OH] | [dimethylpyrazole-OH] | o |
| 14115 | | | [nitrothiophene] | H | H | | o |
| 14116 | H | H | NO₂ | H | [thiophene] | | o |
| 14342 | | | [thiophene] | H | H | [piperazine] | o |
| 14502 | H | H | ⁻OOC— | H | H | H H H | o o |
| 14503 | H | H | ⁻OOC— | H | H | H H H | o o |
| 14504 | H | H | H | H | [methylthiazole] | H H H | o o |
| 14505 | H | H | H | H | [pyrimidine] | H H H | o o |
| | | | | | —CH₂COO⁻ | | |

TABLE 1-continued
DBD Binding Compounds
| ID | | | | | | | |
|----|---|---|---|---|---|---|---|
| 14507 | H | H | H₃CO— | H | H | H | 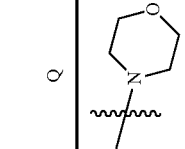 | 0 | 0 | 0 |
| 14510 | | | ⁻OOCCH₂— | | H | H | 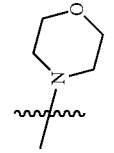 | 0 | 0 | 0 |
Series 2
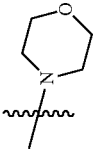
| ID | M₁ | M₂ | M₃ | M₄ | Q | % Inhibition (3 μM) | eGFP IC₅₀ (μM) | PSA IC₅₀ (μM) |
|----|----|----|----|----|---|---|---|---|
| 14332 | CH₃ | CH₃ | H | H | 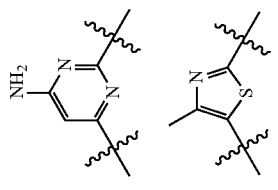 | 91.7 | | |
| 14372 | H | H | NH₂ | H |  | 31.6 | | |
| 14376 | CH₃ | H | H | CH₃ |  | 97.21 | 0.068 | 0.058 |

TABLE 1-continued

DBD Binding Compounds

| ID | | | | | | |
|---|---|---|---|---|---|---|
| 14377 | H | H | Cl | H | morpholine | 94.76 |
| 14378 | H | H | OH | H | morpholine | 57.53 | 7.41 (±0.4) |
| 14380 | Cl | Cl | Cl | H | morpholine | 0 |
| 14381 | H | OCH$_3$ | H | H | morpholine | 76.71 |
| 14382 | H | CH$_3$ | CH$_3$ | H | morpholine | 101.33 |
| 14383 | F | H | F | H | morpholine | 95.3 |
| 14384 | SO$_2$CH$_3$ | H | H | H | morpholine | 73.16 |
| 14374 | OCH$_3$ | H | H | H | morpholine | 59.95 |
| 14373 | H | H | H | H | 2,6-dimethylmorpholine | 70.74 | 5.93 |

Note: row 14378 shows values 57.53 and 7.41 (±0.4) and 8.08.

TABLE 1-continued

DBD Binding Compounds

| ID | | | | Structure | | | |
|---|---|---|---|---|---|---|---|
| 14391 | H | H | H | morpholine-CONH₂ | 7.95 | | |
| 14392 | H | H | H | 2-ethylmorpholine | 55.5 | 7.07 | 10.38 |
| 14393 | H | H | H | morpholine | 31.23 | 46.6 | |
| 14394 | H | NO₂ | H | morpholine | 14.45 | | |
| 14409 | F | F | H | morpholine | 86 | 0.36 | 0.34 |
| 14375 | CH₃ | CH₃ | H | 4-aminopiperidinium | 39.54 | | |
| 14379 | CH₃ | CH₃ | H | N-methyl-4-aminopiperidinium | 66.87 | | |
| 14327 | H | H | H | 3,4-diaminophenyl | 17.01 | | |
| 14387 | H | NH₂ | H | 3-hydroxyphenyl | 108.6 | 14.75 | |

TABLE 1-continued

DBD Binding Compounds

| | | | |
|---|---|---|---|
| 14345 | H | H | 16.88 (3-pyridyl) |
| 14489 | H | H | 82.53 (4-CN-phenyl) 1.79 |
| 14490 | H | H | 70.94 (4-OCH₃-phenyl) 1.06 |

Series 3

Quinolone series

| ID | Structure | % Inhibition (3 μM) | eGFP IC$_{50}$ (μM) | PSA IC$_{50}$ (μM) |
|---|---|---|---|---|
| 14300 | 3-OH-phenyl-quinoline | | 0.23 | 1.04 |
| 14309 | 3-OH-phenyl-isoindoline-quinoline | | 0.75 | 0.5 |
| 14320 | 3-pyridyl-quinoline | 62.05 | 4.20 (±0.6) | 2.26 |
| 14321 | 3-NH₂-phenyl-quinoline | 66.45 | | |

TABLE 1-continued
DBD Binding Compounds
| | | |
|---|---|---|
| 14388 |  | 44.88 10.36 |
| 14336 |  | 27.14 |
| 14440 |  | 8.65 9.48 (±3) |
| 14389 |  | 14.46 |
| 14390 |  | 80.23 2.60 1.23 |
| 14395 |  | 103.08 0.54 0.54 |
| 14400 |  | 79 0.46 0.38 |

TABLE 1-continued

DBD Binding Compounds

| | | | | |
|---|---|---|---|---|
| 14398 | [quinoline with morpholine and NO2] | | 0.82 | 0.85 |
| 14401 | [quinoline with morpholine] | 76 | 0.85 | 0.69 |
| 14433 | [quinoline with morpholine and CN] | | 1.95 | |
| 14434 | [quinoline with morpholine and methyl] | | 1.09 | |
| 14452 | [quinoline with morpholine and Br] | 89.39 | 0.11 | 0.17 |
| 14495 | [quinoline with piperidine] | | 0.60 | |

TABLE 1-continued
DBD Binding Compounds
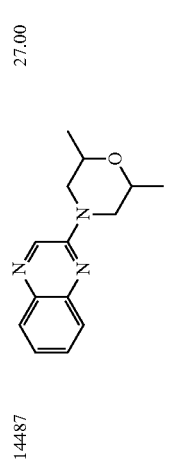
| | |
|---|---|
| 14487 | 27.00 |
| 14453 | 17.29 |
| 14454 | 0 |
| 14112 | 9.0 |
Series 4
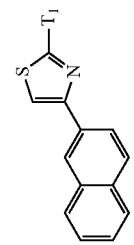
| ID | $T_1$ | % Inhibition (3 μM) | eGFP IC$_{50}$ (μM) | PSA IC$_{50}$ (μM) |
|---|---|---|---|---|
| 14193 | H | | 1.30 | 0.64 |
| 14203 | NHCH$_3$ | 91.53 | 3.17 | 3.91 |

TABLE 1-continued
DBD Binding Compounds
| ID | Structure | | |
|---|---|---|---|
| 14204 | NH₂ | 67.19 | (±0.3) 9.16 10.6 |
| 14198* (modified series 4) | 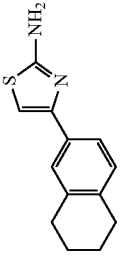 | 54.39 | 5.51 |
Series 5
| ID | Structure | % Inhibition (3 μM) | eGFP IC₅₀ (μM) | PSA IC₅₀ (μM) |
|---|---|---|---|---|
| 14005 | 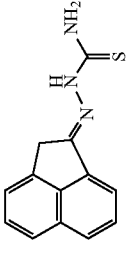 | 92.53 | 2 | |
| 14164 | 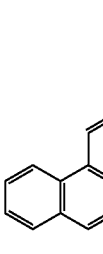 | 86.84 | 3.04 | |
| 14153 | 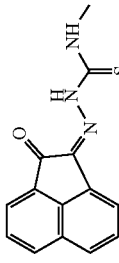 | 99.58 | 6 | |
| 14171 | 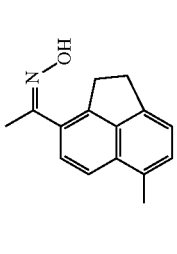 | 99.58 | 3.38 | |

TABLE 1-continued
DBD Binding Compounds
| | | | |
|---|---|---|---|
| 14175 | 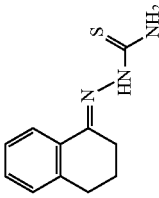 | 45.5 | 13.6 |
| 14205 | 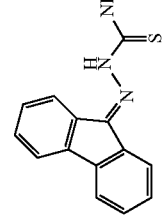 | 45.83 | 7.38 |
| 14172 | 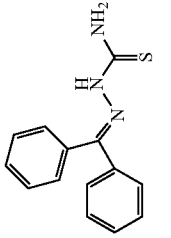 | 46.36 | 29.4 |
| 14151 | 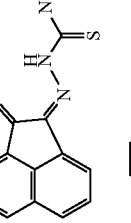 | | 30 |
| 14206 | 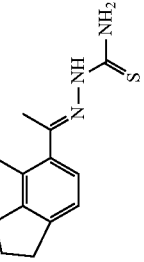 | 108.95 | 3.4 |

TABLE 1-continued

DBD Binding Compounds

| ID | Structure | % Inhibition (3 µM) | eGFP IC$_{50}$ (µM) | PSA IC$_{50}$ (µM) |
|---|---|---|---|---|
| 14053 | 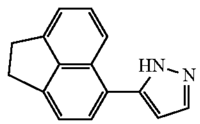 [SMILES: c1cc2c3c(ccc(-c4ccn[nH]4)c3c1)CC2] | | 4 | |

Series 6

| ID | Structure | % Inhibition (3 µM) | eGFP IC$_{50}$ (µM) | PSA IC$_{50}$ (µM) |
|---|---|---|---|---|
| 14065 | 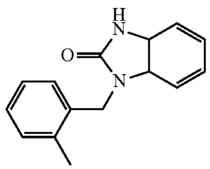 [SMILES: Cc1ccccc1CN1C(=O)NC2C=CC=CC21] | | 10 | |
| 14082 | 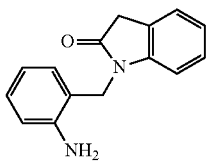 [SMILES: Nc1ccccc1CN1C(=O)Cc2ccccc21] | 93.1 | 9.5 | |
| 14078 | 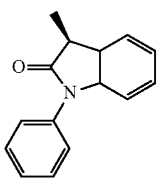 [SMILES: C[C@@H]1C(=O)N(c2ccccc2)C2C=CC=CC21] | 65.37 | 20 | |
| 14088 | 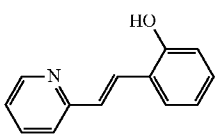 [SMILES: Oc1ccccc1/C=C/c1ccccn1] | | 3.54 | |

TABLE 1-continued
DBD Binding Compounds
| | | |
|---|---|---|
| 14055 | 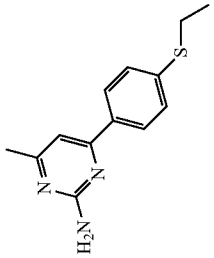 | 10 |
| 14017 | 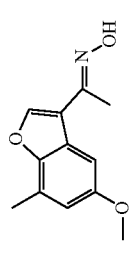 | 41.6 |
| 14010 | 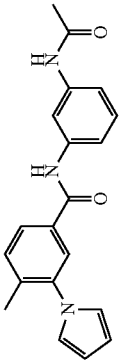 | 32.5  19.26 |
| 14002 | 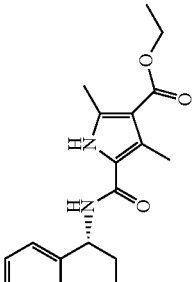 | 11.8  3.54 |
| 14163 | 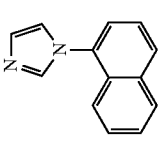 | 24 |
| 14018 | 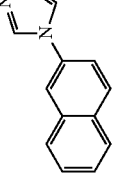 | 13.87 |

Those skilled in the art will appreciate that the point of covalent attachment of the moiety to the compounds as described herein may be, for example, and without limitation, cleaved under specified conditions. Specified conditions may include, for example, and without limitation, in vivo enzymatic or non-enzymatic means. Cleavage of the moiety may occur, for example, and without limitation, spontaneously, or it may be catalyzed, induced by another agent, or a change in a physical parameter or environmental parameter, for example, an enzyme, light, acid, temperature or pH. The moiety may be, for example, and without limitation, a protecting group that acts to mask a functional group, a group that acts as a substrate for one or more active or passive transport mechanisms, or a group that acts to impart or enhance a property of the compound, for example, solubility, bioavailability or localization.

In some embodiments, compounds of TABLE 1 above and as described in the claims may be used for systemic treatment of at least one indication selected from the group consisting of: prostate cancer, breast cancer, ovarian cancer, endometrial cancer, hair loss, acne, hirsutism, ovarian cysts, polycystic ovary disease, precocious puberty and age-related macular degeneration. In some embodiments compounds of TABLE 1 and as described in the claims may be used in the preparation of a medicament or a composition for systemic treatment of an indication described herein. In some embodiments, methods of systemically treating any of the indications described herein are also provided.

Compounds as described herein may be in the free form or in the form of a salt thereof. In some embodiment, compounds as described herein may be in the form of a pharmaceutically acceptable salt, which are known in the art (Berge S. M. et al., *J. Pharm. Sci.* (1977) 66(1):1-19). Pharmaceutically acceptable salt as used herein includes, for example, salts that have the desired pharmacological activity of the parent compound (salts which retain the biological effectiveness and/or properties of the parent compound and which are not biologically and/or otherwise undesirable). Compounds as described herein having one or more functional groups capable of forming a salt may be, for example, formed as a pharmaceutically acceptable salt. Compounds containing one or more basic functional groups may be capable of forming a pharmaceutically acceptable salt with, for example, a pharmaceutically acceptable organic or inorganic acid. Pharmaceutically acceptable salts may be derived from, for example, and without limitation, acetic acid, adipic acid, alginic acid, aspartic acid, ascorbic acid, benzoic acid, benzenesulfonic acid, butyric acid, cinnamic acid, citric acid, camphoric acid, camphorsulfonic acid, cyclopentanepropionic acid, diethylacetic acid, digluconic acid, dodecylsulfonic acid, ethanesulfonic acid, formic acid, fumaric acid, glucoheptanoic acid, gluconic acid, glycerophosphoric acid, glycolic acid, hemisulfonic acid, heptanoic acid, hexanoic acid, hydrochloric acid, hydrobromic acid, hydriodic acid, 2-hydroxyethanesulfonic acid, isonicotinic acid, lactic acid, malic acid, maleic acid, malonic acid, mandelic acid, methanesulfonic acid, 2-napthalenesulfonic acid, naphthalenedisulphonic acid, p-toluenesulfonic acid, nicotinic acid, nitric acid, oxalic acid, pamoic acid, pectinic acid, 3-phenylpropionic acid, phosphoric acid, picric acid, pimelic acid, pivalic acid, propionic acid, pyruvic acid, salicylic acid, succinic acid, sulfuric acid, sulfamic acid, tartaric acid, thiocyanic acid or undecanoic acid. Compounds containing one or more acidic functional groups may be capable of forming pharmaceutically acceptable salts with a pharmaceutically acceptable base, for example, and without limitation, inorganic bases based on alkaline metals or alkaline earth metals or organic bases such as primary amine compounds, secondary amine compounds, tertiary amine compounds, quaternary amine compounds, substituted amines, naturally occurring substituted amines, cyclic amines or basic ion-exchange resins. Pharmaceutically acceptable salts may be derived from, for example, and without limitation, a hydroxide, carbonate, or bicarbonate of a pharmaceutically acceptable metal cation such as ammonium, sodium, potassium, lithium, calcium, magnesium, iron, zinc, copper, manganese or aluminum, ammonia, benzathine, meglumine, methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, glutamine, methylglucamine, theobromine, purines, piperazine, piperidine, procaine, N-ethylpiperidine, theobromine, tetramethylammonium compounds, tetraethylammonium compounds, pyridine, N,N-dimethylaniline, N-methylpiperidine, morpholine, N-methylmorpholine, N-ethylmorpholine, dicyclohexylamine, dibenzylamine, N,N-dibenzylphenethylamine, 1-ephenamine, N,N'-dibenzylethylenediamine or polyamine resins. In some embodiments, compounds as described herein may contain both acidic and basic groups and may be in the form of inner salts or zwitterions, for example, and without limitation, betaines. Salts as described herein may be prepared by conventional processes known to a person skilled in the art, for example, and without limitation, by reacting the free form with an organic acid or inorganic acid or base, or by anion exchange or cation exchange from other salts. Those skilled in the art will appreciate that preparation of salts may occur in situ during isolation and purification of the compounds or preparation of salts may occur by separately reacting an isolated and purified compound.

In some embodiments, compounds and all different forms thereof (e.g. free forms, salts, polymorphs, isomeric forms) as described herein may be in the solvent addition form, for example, solvates. Solvates contain either stoichiometric or non-stoichiometric amounts of a solvent in physical association the compound or salt thereof. The solvent may be, for example, and without limitation, a pharmaceutically acceptable solvent. For example, hydrates are formed when the solvent is water or alcoholates are formed when the solvent is an alcohol.

In some embodiments, compounds and all different forms thereof (e.g. free forms, salts, solvates, isomeric forms) as described herein may include crystalline and amorphous forms, for example, polymorphs, pseudopolymorphs, conformational polymorphs, amorphous forms, or a combination thereof. Polymorphs include different crystal packing arrangements of the same elemental composition of a compound. Polymorphs usually have different X-ray diffraction patterns, infrared spectra, melting points, density, hardness, crystal shape, optical and electrical properties, stability and/or solubility. Those skilled in the art will appreciate that various factors including recrystallization solvent, rate of crystallization and storage temperature may cause a single crystal form to dominate In some embodiments, compounds and all different forms thereof (e.g. free forms, salts, solvates, polymorphs) as described herein include isomers such as geometrical isomers, optical isomers based on asymmetric carbon, stereoisomers, tautomers, individual enantiomers, individual diastereomers, racemates, diastereomeric mixtures and combinations thereof, and are not limited by the description of the formula illustrated for the sake of convenience.

In some embodiments, compounds may include analogs, isomers, stereoisomers, or related derivatives. Compounds of the present invention may include compounds related to the compounds of TABLE 1 by substitution or replacement of certain substituents with closely related substituents, for instance replacement of a halogen substituent with a related halogen (ie. bromine instead of chlorine, etc) or replacement of an alkyl chain with a related alkyl chain of a different length, and the like. In other embodiments, compounds may include compounds within a generic or Markush structure, as determined from structure-activity relationships identified from the data presented in TABLE 1. By way of example, the ring structures A, B, and C have different compositions depending on the types of compounds tested. Different ring structures that have been demonstrated to have good efficacy may be combined with other efficacious ring structures, so long as the A-B-C configuration shown in TABLE 1 is maintained. In this way, many different combinations of ring structures may be expected to also be efficacious. The determination of such structure-activity relationships for the development of generic Markush structures is within the skill of one in the art.

In some embodiments, pharmaceutical compositions as described herein may comprise a salt of such a compound, preferably a pharmaceutically or physiologically acceptable salt. Pharmaceutical preparations will typically comprise one or more carriers, excipients or diluents acceptable for the mode of administration of the preparation, be it by injection, inhalation, topical administration, lavage, or other modes suitable for the selected treatment. Suitable carriers, excipients or diluents (used interchangeably herein) are those known in the art for use in such modes of administration.

Suitable pharmaceutical compositions may be formulated by means known in the art and their mode of administration and dose determined by the skilled practitioner. For parenteral administration, a compound may be dissolved in sterile water or saline or a pharmaceutically acceptable vehicle used for administration of non-water soluble compounds such as those used for vitamin K. For enteral administration, the compound may be administered in a tablet, capsule or dissolved in liquid form. The tablet or capsule may be enteric coated, or in a formulation for sustained release. Many suitable formulations are known, including, polymeric or protein microparticles encapsulating a compound to be released, ointments, pastes, gels, hydrogels, or solutions which can be used topically or locally to administer a compound. A sustained release patch or implant may be employed to provide release over a prolonged period of time. Many techniques known to one of skill in the art are described in *Remington: the Science & Practice of Pharmacy* by Alfonso Gennaro, 20th ed., Lippencott Williams & Wilkins, (2000). Formulations for parenteral administration may, for example, contain excipients, polyalkylene glycols such as polyethylene glycol, oils of vegetable origin, or hydrogenated naphthalenes. Biocompatible, biodegradable lactide polymer, lactide/glycolide copolymer, or polyoxyethylene-polyoxypropylene copolymers may be used to control the release of the compounds. Other potentially useful parenteral delivery systems for modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

Compounds or pharmaceutical compositions as described herein or for use as described herein may be administered by means of a medical device or appliance such as an implant, graft, prosthesis, stent, etc. Also, implants may be devised which are intended to contain and release such compounds or compositions. An example would be an implant made of a polymeric material adapted to release the compound over a period of time.

An "effective amount" of a pharmaceutical composition as described herein includes a therapeutically effective amount or a prophylactically effective amount. A "therapeutically effective amount" refers to an amount effective, at dosages and for periods of time necessary, to achieve the desired therapeutic result, such as reduced tumor size, increased life span or increased life expectancy. A therapeutically effective amount of a compound may vary according to factors such as the disease state, age, sex, and weight of the subject, and the ability of the compound to elicit a desired response in the subject. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as smaller tumors, increased life span, increased life expectancy or prevention of the progression of prostate cancer to an androgen-independent form. Typically, a prophylactic dose is used in subjects prior to or at an earlier stage of disease, so that a prophylactically effective amount may be less than a therapeutically effective amount.

It is to be noted that dosage values may vary with the severity of the condition to be alleviated. For any particular subject, specific dosage regimens may be adjusted over time according to the individual need and the professional judgment of the person administering or supervising the administration of the compositions. Dosage ranges set forth herein are exemplary only and do not limit the dosage ranges that may be selected by medical practitioners. The amount of active compound(s) in the composition may vary according to factors such as the disease state, age, sex, and weight of the subject. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage.

In some embodiments, compounds and all different forms thereof as described herein may be used, for example, and without limitation, in combination with other treatment methods for at least one indication selected from the group consisting of: prostate cancer, breast cancer, ovarian cancer, endometrial cancer, hair loss, acne, hirsutism, ovarian cysts, polycystic ovary disease, precocious puberty and age-related macular degeneration. For example, compounds and all their different forms as described herein may be used as neoadjuvant (prior), adjunctive (during), and/or adjuvant (after) therapy with surgery, radiation (brachytherapy or external beam), or other therapies (eg. HIFU).

In general, compounds as described herein should be used without causing substantial toxicity. Toxicity of the compounds as described herein can be determined using standard techniques, for example, by testing in cell cultures or experimental animals and determining the therapeutic index, i.e., the ratio between the LD50 (the dose lethal to 50% of the population) and the LD100 (the dose lethal to 100% of the population). In some circumstances however, such as in severe disease conditions, it may be appropriate to administer substantial excesses of the compositions. Some compounds as described herein may be toxic at some concentrations. Titration studies may be used to determine toxic and non-toxic concentrations. Toxicity may be evaluated by examining a particular compound's or composition's specificity across cell lines using PC3 cells as a negative control that do not express AR. Animal studies may be used to provide an indication if the compound has any effects on other tissues. Systemic therapy that targets the AR will not likely cause major problems to other tissues since anti-androgens and androgen insensitivity syndrome are not fatal.

Compounds as described herein may be administered to a subject. As used herein, a "subject" may be a human, non-human primate, rat, mouse, cow, horse, pig, sheep, goat, dog, cat, etc. The subject may be suspected of having or at risk for having a cancer, such as prostate cancer, breast cancer, ovarian cancer or endometrial cancer, or suspected of having or at risk for having acne, hirsutism, alopecia, benign prostatic hyperplasia, ovarian cysts, polycystic ovary disease, precocious puberty, or age-related macular degeneration. Diagnostic methods for various cancers, such as prostate cancer, breast cancer, ovarian cancer or endometrial cancer, and diagnostic methods for acne, hirsutism, alopecia, benign prostatic hyperplasia, ovarian cysts, polycystic ovary disease, precocious puberty, or age-related macular degeneration and the clinical delineation of cancer, such as prostate cancer, breast cancer, ovarian cancer or endometrial cancer, diagnoses and the clinical delineation of acne, hirsutism, alopecia, benign prostatic hyperplasia, ovarian cysts, polycystic ovary disease, precocious puberty, or age-related macular degeneration are known to those of ordinary skill in the art.

Definitions used include ligand-dependent activation of the androgen receptor (AR) by androgens such as dihydrotestosterone (DHT) or the synthetic androgen (R1881) used for research purposes. Ligand-independent activation of the AR refers to transactivation of the AR in the absence of androgen (ligand) by, for example, stimulation of the cAMP-dependent protein kinase (PKA) pathway with forskolin (FSK).

Some compounds and compositions as described herein may interfere with a mechanism specific to dimerization- and/or DNA-binding-dependent activation (e.g. potentially binding to AR DBD to block AR transcription by disrupting AR dimerization and preventing DBD-DNA binding.

Various alternative embodiments and examples of the invention are described herein. These embodiments and examples are illustrative and should not be construed as limiting the scope of the invention.

Material and Method
In Silico Pipeline
  1. Protein and Ligand Preparation
  The crystal structure of AR DBD dimer-DNA (1R4I.pdb) was prepared using the Protein Preparation Wizard within Maestro 9.3 (Schrödinger, LLC). The hydrogen atoms were added, bond orders were assigned, and missing side chains for some residues were added using Prime. The side chains were minimized using OPLS-2005 force field.
  A lead-like ZINC database with 3 million small molecules was imported into Molecular Operating Environment (MOE) 2010. All the molecules were protonated/deprotanated by a washing process, added partial charges and minimized with the MMFF94x force field to a gradient of 0.0001 kcal/mol Å. After the minimization, the database was exported as an sdf file.

2. Druggable Binding Site Detection in AR DBD
  To identify potential druggable binding sites in the AR DBD dimer-DNA structure, the AR DBD dimer-DNA complex, DBD dimer and DBD monomer were detected using both geometry-based and energy-based methods, like Site Finder within MOE 2010, Pocket-Finder and Q-siteFinder. Possible binding sites were examined and compared based on the parameters like size, shape, amino acid composition and the volume of the pocket.

3. Virtual screening of potential AR DBD binders
  Two docking programs Glide in Maestro 9.3 and eHiTs 2011 were used for the virtual screening. The residues in the predicted binding site were used to define the active site for the virtual screening. For Glide docking, the grid was defined using a 20 Å box centered on the selected residues. No constraints were applied and all the settings were kept as default. The ZINC database was docked using Glide SP mode, and a cutoff value was given to discard compounds of potentially low binding affinities with the receptor. The remaining compounds were subjected to the eHiTs docking in the default settings. A cutoff value of eHiTs score was used to keep compounds consistently scored well by both docking programs. An RMSD (root median square deviation) value was calculated on docked poses from both programs, and compounds with RMSD values higher than 2 Å were removed. The rest compounds were clustered based on structural similarity in MOE 2010, and compounds were selected from top ranked clusterings in regard to favorable interactions with the receptor.

In Vitro Identification of the Compounds
  1. Cell Culture: LNCaP and PC3 human prostate cancer cells were obtained from American Type Culture Collection (ATCC, Manassas, Va.) and grown in RPMI 1640 medium supplemented with 5% fetal bovine serum (FBS) (Invitrogen). The LNCaP eGFP cell line was stably transfected with an androgen-responsive probasin-derived promoter fused to an eGFP reporter (LN-ARR2PB-eGFP) using a lentiviral approach, and were grown in phenol-red-free RPMI 1640 supplemented with 5% CSS. Inihouse developed MDV3100-resistant LNCaP cells were cultured in RPMI 1640 supplemented with 5% FBS and 10 μM MDV3100. All cells were maintained at 37° C. in 5% CO2.

2. eGFP cellular AR transcription assay: The AR transcriptional activity was assayed as previously described (Tavassoli, Snoek et al. 2007).

3. Prostate-specific antigen (PSA) assay: The evaluation of PSA levels secreted into the media was performed in parallel to the eGFP assay using the same plates. After cells were incubated for 3 days, 150 μl of the media was taken from each well, and added to 150 μl of PBS. PSA levels were then evaluated using Cobase 411 analyzer instrument (Roche Diagnostics) according to the manufacturer's instructions.

4. Biolayer interferometry (BLI) assay: The direct reversible interaction between small molecules and the AR was measured as previously described (Lack, Axerio-Cilies et al. 2011).

5. Androgen displacement assay: The androgen displacement was assessed with the Polar Screen Androgen Receptor Competitor Green Assay Kit as per the instructions of the manufacturer (Lack, Axerio-Cilies et al. 2011).

6. SRC2-3 peptide displacement assay: The AR AF2 specific peptide displacement was assayed as previously described.

7. Cell viability assay: The PC3, LNCaP, and MDV3100-resistant cells were plated at 3,000 cells per well in RPMI 1640 containing 5% charcoal stripped serum (CSS) in a 96-well plate, treated with 0.1 nM R1881 and compounds (0-25 µM) for 96 hrs. After 4 days of treatment, cell density was measured using the 3-(4, 5-dimethylthiazol-2-yl)-5-(3-carboxymethoxyphenyl)-2-(4-sulfophenyl)-2H-tetrazolium assay according to the manufacturer's protocol (CellTiter 961 Aqueous One Solution Reagent, Promega).

8. Mutation Studies: The residues in the predicted binding site were mutated using the Quickchange™ Site-Directed Mutagenesis Kit as per the instructions.

9. Transient Transfection: The PC3/MCF7 cells were seeded into a 96-well plate (2,000 cells/well). After 24 hrs, the wild-type AR (50 ng/well)/AR mutants and AR3TK-luciferase plasmids (1:3) were co-transfected into PC3 cells or ERE-luciferase (50 ng/well) was transfected into MCF7 cells using transfection reagent TT20. 24 hrs after the transfection, the cells were treated with the compounds at various concentrations. And 24 hrs later, the cells were lysed and the reading was taken using a luminometer.

Constructs

Full-length human AR (hARWT) or splice variant (AR-V7) was encoded on a pcDNA3.1 expression plasmid.

Point mutations in the DBD were generated with the QuikChange™ mutagenesis kit (Stratagene™) using hARWT orAR-V7 templates. Mutagenic primers were generated using a primer design tool (Agilent™). The glucocorticoid receptor (GR) was expressed from the pGR mammalian expression vector as described previously (Miesfeld, R. et al. (1986) Genetic complementation of a glucocorticoid receptor deficiency by expression of cloned receptor cDNA. Cell 46, 389-399). Progesterone receptor (PR) was expressed from the pSG5-PRB vector and was obtained from Dr. X. Dong. The AR-DBD_hinge domain (amino acids 558-689) was amplified from the hARwT construct and cloned into the pTrc expression vector (N-terminal His$_6$ tag, Invitrogen™) using the polymerase incomplete primer extension method (PIPE). Briefly, the AR-DBD+hinge domain was cloned by mixing the PCR products resulting from the following templates and primers: AR(558-689) insert from hAR$_{WT}$ template 5'-*CAT CAT CAT CAT CAT CAT GGT* ACC TGC CTG ATC TGT GG
and

5'-*CAG GCT GAA AAT CTT CTC TCA* GTG TCC AGC ACA CAC TAC AC;

pTrc vector lacking multiple cloning site

5'-*ATCTCCACAGATCAGGCAGGT* ACC ATG ATG ATG ATG ATG ATG
and

5'-*GGT GTA GTG TGT GCT GGA CAC-* TGA GAG AAG ATT TTC AGC CTG;

the underlined primer sections anneal to the specified template, although their 5'-extensions (italicized) are complementary to the corresponding primer sequence of the other PCR. Plasmid assembly is achieved by mixing the PCR products from each reaction (Klock, H. E. et al. (2008) Combining the polymerase incomplete primer extension method for cloning and mutagenesis with microscreening to accelerate structural genomics efforts. *Proteins* 71, 982-994), followed by transformation into chemically competent bacteria. A similar strategy was used to clone the AR-DBD+hinge into the Pan4 vector (avidity) expressing the N-terminal biotinylation sequence (GLNDIFEAQKIEWHE) and C-terminal His tag. YFP-AR plasmid was a gift from Dr. Jan Trapman (van Royen, M. E. et al. (2012) Stepwise androgen receptor dimerization. *J. Cell Sci.* 125, 1970-1979) and is based on pEYFP-C1 (Clontech™). YFP-V7 was constructed by polymerase incomplete primer extension method using the following primers and templates: AR-V7 insert from pcDNA3. AR-V7 template 5'-*GGT GCT GGA GCA GGT GCT GGA* ATG GAA GTG CAG TTA GGG CTG
and

5'-*GGA AAT AGG GTT TCC AAT GCT* TCA GGG TCT GGT CAT TTT GAG;

pEYFPC1 vector lacking the full-length AR

5'-*CAG CCC TAA CTG CAC TTC CAT* TCC AGC ACC TGC TCC AG
and

5'-*CTC AAA ATG ACC AGA CCC TGA* AGC ATT GGA AAC CCT ATT TCC.

Cell Culture, Transfection, and Luciferase Assays

PC3 human PCa cells (AATC) were serum-starved in RPMI 1640 media (Invitrogen™) supplemented with 5% charcoal-stripped serum (CSS) (RPMI 1640 medium with 5% CSS) for 5 days prior to transfection. For luciferase assays, PC3 cells were seeded in 96-well plates (5000 cells/well) in RPMI 1640 medium with 5% CSS for 24 h, followed by transfection with 50 ng of hAR or other nuclear receptor plasmid, 50 ng of ARR3tk-luciferase, and 0.3 µl/well TranslT20/20 transfection reagent (TT20, Mirus™) for 48 h. Cells were then treated with compounds at various concentrations and 0.1 nMR1881 (in 100% ethanol) for 24 h. GR or PR activation was stimulated with 1 nM dexamethasone or progesterone, respectively. ER-α transcriptional activity was measured with a MCF-7 cell line bearing the stable transfection of an estrogen-response element-luciferase reporter, with transcriptional activity stimulated by 1 nM estradiol. Cell lysis was carried out with 60 µl of 1X passive lysis buffer/well (Promega™)

20 µl of cell lysate from each well were mixed with 50 µl of luciferase assay reagent (Promega™), and luminescence was recorded on a TECAN™ M200pro plate reader. Luciferase assays with splice variant AR were performed the same way but with only 5 ng of pcDNA3.1 AR-V7 (to limit the high level of AR-V7 expression) and no R1881. R1-AD1 and TALEN-engineered R1-D567 cell lines have been described previously (Nyquist, M. D. et al. (2013) TALEN-engineered AR gene rearrangements reveal endocrine uncoupling of androgen receptor in prostate cancer. *Proc. Natl. Acad. Sci. U.S.A.* 110, 17492-17497). Assays with R1-AD1 and R1-D567 cells were performed as above but with transfection of only ARR₃tk-luciferase reporter and 10,000 cells/well.

Western Blots

Cell lysates (40 μl) from luciferase assays (96-well plate) were separated on a 10% SDS-polyacrylamide mini gel. Protein was transferred to methanol-charged PVDF membranes and probed with anti-AR441 (mouse, Sigma™) monoclonal primary antibody. Blots were also probed with polyclonal anti-actin (rabbit, Sigma™) to show equal loading and polyclonal anti-PARP/anti-cleaved PARP (rabbit, Sigma™) to test for induction of apoptosis. Lysates from CWR-R1 cells were additionally probed with polyclonal anti-FKBP5 (rabbit, Sigma™) following 2 days of incubation with compounds.

PSA Measurements

LNCaP cells maintained in RPMI 1640 medium with 5% CSS were incubated in 96-wells (10,000 cells/well) for 2 days in the same culture medium and in the presence of compounds and 1 nM R1881. Following the incubation period, 150 μl of the media was taken from each well, and PSA levels were quantified using a Cobas e411 analyzer (Roche Applied Science™) according to the manufacturer's instructions. The same instrument was used to analyze serum PSA from mice during the in vivo analysis.

Microarray Genetic Profile

LNCaP cells were grown for 24 h under the following four conditions: 1) DMSO without R1881; 2) DMSO with R1881 (1 nM); 3) compound 14449 at 400 nM with R1881; and 4) enzalutamide at 120 nM with R1881. Compound concentration followed approximately the IC50 concentration determined in luciferase reporter assays.

Each condition was repeated in triplicate. After 24 h, the total cellular mRNA was extracted from each of the 12 samples (four conditions three times), and the gene expression level of 50,737 transcripts was measured from custom Agilent microarrays.

The gene expression data were quantile normalized across all the samples and transformed into a log 2 scale. A two-sample t test was performed on the expression level of each transcript between condition 3 (compound 14449 with R1881) and condition 2 (DMSO with R1881), and between condition 4 (enzalutamide with R1881) and condition 2 (DMSO with R1881). A gene is considered to be differentially expressed if the p value from the two-sample t test is less than 0.05. Fisher's exact test and odds ratio were used to evaluate the overlap between different sets of differentially expressed genes.

Confocal Microscopy

Approximately 40,000 PC3 cells were seeded for 48 h on sterile coverslips placed within 12-well plates in RPMI 1640 medium with 5% CSS. Transfection of YFP-AR or YFP-V7 plasmids (100 ng per well) was performed using TT20 (3 μl) for 48 h. Cells were then treated with 10 nM R1881 and 25 μM compounds for 6 h. After aspiration of the media, cells were washed once with PBS and fixed in 4% paraformaldehyde overnight at 4° C., followed by mounting on charged cover slides using DAPI mount (Vector Laboratories). Images were taken on a Zeiss LSM 780 confocal spinning disk microscope controlled with Zen 2012 software. YFP and DAPI were visualized with excitation wavelengths of 508 and 388 nm, respectively.

Chromatin Immunoprecipitation (ChIP)

Androgen-deprived LNCAP cells were treated for 24 h with DMSO alone, DMSO+R1881, or compounds+R1881. DNA-protein crosslinking was performed with 1% formaldehyde treatment for 10 min at room temperature and quenched with 125 mM glycine for 5 min. Cell lysates ($1\times10^7$ cells/nil) were subjected to sonication with a Thermo Scientific™ ⅛-inch sonication probe and Sonic Dismembrator 550™ instrument to yield DNA fragments of 200-1000 bp in size. Immunoprecipitation of lysates ($3.3\times10^6$ cell eq) was performed with 5 μg of anti-AR-N20 antibody (Santa Cruz Biotechnology™) or 1 μg of rabbit isotype control IgG (Santa Cruz Biotechnology™) using a EZ-ChIP chromatin immunoprecipitation kit (Millipore™). Bound DNA was quantified by quantitative PCR (SYBR Green master mix, Invitrogen™) using the following primer sets: PSA enhancer, forward 5'-ATG GAGAAAGTGGCT-GTGGC and reverse 5'-TGCAGTIVG TGA GTG GTC AT; FKBP5 enhancer, forward 5'-CCC CCC TAT TTT AAT CGG AGT AC and reverse 5'-TTT TGA AGA GCA CAG AAC ACC CT; GAPDH promoter, forward 5'-TAC TAGCGGTTTTACGGGCG and reverse 5'-TCGAACAGG AGC AGA GAG CGA. The quantitative PCR results are presented as fold enrichment of PCR amplification over control IgG antibody and normalized based on the total input (nonprecipitated chromatin). Primers for the GAPDH promoter were used as a negative control lacking any androgen-response element.

Purification of AR-DBD Proteins

The plasmid encoding the AR-DBD+hinge was transformed into BL21 (DE3). BL21 cells designated for expression of biotin-labeled AR-DBD+hinge were co-transformed with the Pan4 AR-DBD+hinge (ampicillin selection) and biotin ligase expression vectors (pBir-Acm, chloramphenicol selection). Single colonies were grown in 2 liters of LB media supplemented with 50 μg/ml ampicillin and 35 μg/ml chloramphenicol (where appropriate) to $A_{600\ nm}=0.6$ before induction with 0.1 mM isopropyl β-D-1-thiogalactopyranoside for 3 h at 37° C. Cultures expressing the AR-DBD with the biotinylation sequence were simultaneously supplemented with 0.150 mM biotin during the induction step. Cell pellets were resuspended in ~20 ml of 50 mM Tris-HCl, pH 8.0, 300 mM NaCl, 5% glycerol (Buffer A) supplemented with 10 mM imidazole and incubated with 0.1 mg/ml chicken egg white lysozyme (Sigma™) and 0.1 mM PMSF protease inhibitor for 30 min on ice. Cell lysis was achieved by sonication, followed by centrifugation at 13,000×g for 30 min at 4° C. The supernatant was rotated with 2 ml of nickel-agarose beads (GE Healthcare™) for 1 h at 4° C. and then directly loaded onto a Poly-Prep 10-ml gravity chromatography column (Bio-Rad™). Washing was performed with 2×4 ml of Buffer A supplemented with 20 mM imidazole. Pure proteins were eluted in 500-μl fractions with 2 ml of Buffer A containing 250 mM imidazole.

EMSA (Gel Shift) Assays and Biolayer Interferometry Analysis

Electrophoretic mobility shift assays (EMSA) were performed using purified AR-DBD and dsDNA bearing the ARE 2 sequence. The ARE was formed by annealing the following complementary oligonucleotides in $H_2O$: upper strand, 5'-TAC AAA TAG GTT CTT GG AGTACT TTA CTAGGC ATG GAC AAT G, and lower strand, 5'-CAT TGT CCA T GCCTAG TAA AGTACT CCA AGA ACC TAT TTG TA. Positions of hexameric AREs are underlined. Scrambled DNA was annealed from the following sequences: upper strand, 5'-TAAAACGTGGTCCCTGGTACTGCCTT CGT-GCCA TTC GAT TTT, and lower strand, 5'-AAA ATC GAA TGG CAC GAA GGC AGT ACC AGG GAC CAC GTT TTA. Protein-DNA complexes were allowed to incubate on ice for 30 min in loading buffer (20 mM Tris, pH 8, 50 mM NaCl, 1 mM EDTA, 10 μg/ml poly(dI-dC), 5 mM MgCl2, 200 μl/ml BSA, 5% glycerol, and 1 mM DTT), followed by electrophoresis on 6% native-PAGE in 1×TBE, pH 8.0. Visualization of protein-DNA complexes was performed with SyberSafe™DNAstaining dye.

Biolayer interferometry analysis on a ForteBio Octet Red™ instrument was carried out using biotinylated AR-DBD+hinge in Buffer A with 5% DMSO throughout all experiments. The DBD (0.1 mg/ml) was loaded onto streptavidin sensors in 200 µl of buffer for 30 min, followed by blocking of free streptavidin sites with biocytin (10 µg/ml) for 10 min. DBD-loaded sensors were then pre-equilibrated in 50 µM compound or 5% DMSO alone for 100 s in the same buffer. The kinetics of DNA association were monitored by moving sensors into wells containing dsDNA (ARE, 3 µM) supplemented with 50 µM compound for 120 s. This was followed by dissociation in buffer+compound, but lacking DNA, for an additional 120 s. Biocytin-blocked control sensors (no AR-DBD) were subjected to the same experimental conditions, and nonspecific interactions with dsDNA were subtracted from each curve.

Assessment of Tumor Growth and PSA for Castration-Resistant LNCaP Xenografts 6-8-Week-old nude mice (Harlan Sprague-Dawley) weighing 25-31 g were subcutaneously inoculated with LNCaP cells (106 cells in BD Matrigel, BD Biosciences) at the posterior dorsal site. Tumor volume, body weight, and serum PSA levels were measured weekly. When serum PSA levels reached more than 25 ng/ml, mice were castrated. When PSA recovered to pre-castration levels, mice were randomized into three treatment groups as follows: vehicle, 10 mg/kg enzalutamide, or 100 mg/kg of compound 14449 and treated via intraperitoneal injection twice daily for 4 weeks. Calipers were used to measure the three perpendicular axes of each tumor to calculate the tumor volume. Mice were also weighed weekly and monitored daily for signs of toxicity, including death, lethargy, blindness, and disorientation

EXAMPLES

In Silico Hypothesis

1. Identification of a Potential Druggable Binding Site in the AR DBD

After comparing all the identified binding sites from the DBD dimer-DNA complex, DBD dimer, and DBD monomer, a potential binding site was identified in the DBD monomer, which is supposed to be able to interrupt the DBD-DNA binding if the compound binds. The binding site is mainly composed of residues from one alpha-helix including Arg568, Val564, and Phe565, and some polar residues Tyr576 and Gln574 from a loop. It is a region involving residues which make key interactions for the DNA binding, like the Arg568 which form van der waals contacts with Val564 and the nucleotide (Not shown).

2. Identification of Compounds Binding to AR DBD by Virtual Screening

The ZINC database was firstly screened against the detected binding site in AR DBD subunit by the docking program Glide. A total of 462,588 compounds with docking score higher than (<−4) was discarded, and compound were filtered by molecular weight, charges, and number of rings, and the remaining compounds (170,000) were submitted for eHiTs docking. 59,586 compounds were retained with eHiTs score below (<−3), and RMSD values were calculated for these compounds. 8,953 compounds with RMSD (<3 Å) were processed for the selection of potential virtual hits. Through visual inspection of the receptor-ligand interactions, 100 compounds were selected for experimental evaluation.

3. In Vitro Identification of AR Inhibitors Targeting AR DBD

1. Identification of Potent and Diversified AR Inhibitors

The selected compounds were assessed with a non-destructive eGFP assay that quantifies levels of AR transcriptional activity, and compounds belong to different chemical classes were identified (TABLE 1—Series 1-6), and particularly, a 4-(4-phenylthiazol-2-yl)morpholine compound (14228) showed high potency of AR transcriptional inhibition. This compound inhibits AR transcription and suppresses PSA level in a concentration-dependent manner, with $IC_{50}$s in low nanomolar range (0.274 µM and 0.188 µM, respectively). It was further measured for its ability of inhibiting the growth of prostate cancer cells in three cell lines, AR-positive LNCaP and MDV3100-resistant cell lines, and AR-negative PC3 cell line. It showed that the compound strongly inhibits the AR-positive prostate cancer cell lines, while no effect on the AR-negative cells, which indicates the potency of this compound was through the inhibition of AR (FIG. 3).

4. Compound 14228 not Interacting with Other Known Binding Sites in AR

As there are other known binding sites in AR including the hormone binding site (HBS), activation function-2 (AF2) site, binding function 3 (BF3) and N-terminal activation function-1 (AF1) site, we utilized other assays to rule out possible binding to those sites. The androgen displacement assay demonstrated that it does not displace androgen to occupy the AR HBS, so it is a non-competitive AR inhibitor. Neither does it displace the peptide in the AF2 binding site demonstrated by a fluorescence polarization peptide displacement assay for AF2. Furthermore, the biolayer interferometry (BLI) assay showed that there is no binding in the C-terminal ligand binding domain (LBD), so it is not a BF3 binder either. All these evidences suggest the compound does not bind to any binding site in the LBD. Then we used an AF1 assay to measure whether the potency of this compound comes from the inhibition of AF1 transactivation. The CREB and Gal4 plasmid were co-transfected into an AR-negative cell line PC3, and after the treatment there was no inhibition of the CREB and Gal4, which indicates it does not affect the AF1 (data not shown).

5. Direct Evidence that the Compound Binding to AR DBD

Figure 4:
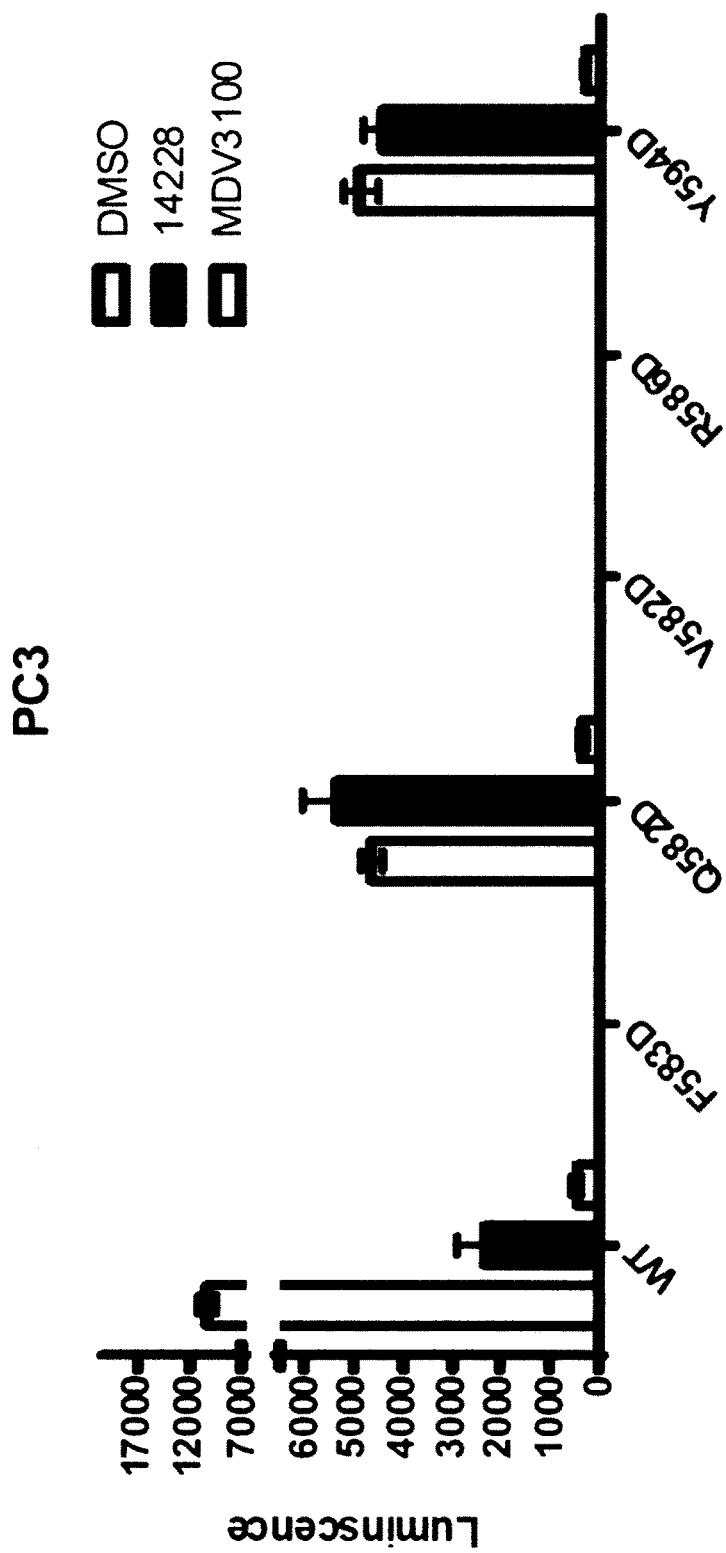
FIG. 4 The transcriptional activity of 14228 on the AR mutants (Glu592, Tyr594, Val582, Arg586, and Phe583) compared to wild-type AR.

To further prove the compound binds to AR DBD as hypothesized, we did mutation studies on the predicted binding site. Based on our molecular modeling, Val581, Phe582, Arg586, Glu591, and Tyr593 are key residues which may have hydrogen-bonding and hydrophobic interactions with the ligand. Thus, we mutated these residues into aspartic acid and tested our compound with these mutants. Among these mutants, when the Val581, Phe582, and Arg586 mutants were co-transfected with AR3TK-luciferase reporter into AR-negative PC3 cells, the mutants cannot activate luciferase expression in the luciferase assay (FIG. 4), and meanwhile, no AR expression was detected in the western blot (data not shown). The compounds do not inhibit the Glu591 and Tyr593 mutants (which can activate wild-type AR), which suggests the compound binds to AR DBD and that these two residues are critical for the binding affinity (FIG. 4).

Compound binding to AR DBD was further confirmed by a protein digestion assay. The AR DBD was not digested by trypsin in the presence of the compound 14288, while it was digested with vehicle or other antiandrogens like MDV3100 (data not shown).

6. Specificity of the Identified Compounds

As the DBD is a highly conservative domain in the nuclear receptors, compounds targeting this domain may have poor selectivity. To rule out the non-specificity problem, we measured the inhibition of our compounds in other nuclear receptors, like ER. The identified compounds were tested in breast cancer MCF7 cells transfected with the ERE-luciferase reporter, which did not show remarkable effect on ER inhibition (data not shown).

7. Structural Modification on 14228

As the initial hit compound 14228 showed favorable profiles, more analogues were purchased or synthesized based on the docking model (not shown). Structural modifications were made on the tripartite composition of 14228, the phenyl ring, thiazole and morpholine group (TABLE 1), and some analogues like 14370 showed improved activities compared to the parental compound.

8. Identification of a Partial AR Agonist Character of 14368

To circumvent resistance to conventional anti-androgens caused by mutations in the AR-LBD, we explored an alternative druggable binding site on the DBD segment of the AR and developed a series of 4-(4-phenylthiazol-2-yl)morpholines capable of selective inhibition of the receptor's activity by disrupting its interaction with DNA. One derivative of this chemical class, compound 14368, demonstrated a very efficient inhibition of AR transcription in a reporter assay and expression of the AR target gene, PSA, in LNCaP cells after R1881 stimulation (the corresponding eGFP $IC_{50}$ and PSA $IC_{50}$ values were 0.035 μM and 0.13 μM respectively). However, it was also observed that this inhibition was reversed at high concentrations of the compound (FIG. 1A-B), which suggested an agonistic effect. To verify these findings, we evaluated the effect of the compound using the same AR-regulated eGFP-expressing LNCaP cells without R1881 stimulation. In the absence of the androgen, 14368 was able to vigorously enhance AR transcriptional activity (FIG. 1C). Importantly, the observed agonistic effect of this compound occurred in LNCaP cells, which carry the T877A AR mutation. In order to validate that this effect is related to the presence of the T877A mutation, a luciferase reporter assay was used to study the transcriptional activity of wild type AR and the T877A-AR mutant in PC3 cells, which are AR negative. AR transcription in PC3 cells transiently transfected with wild type AR was inhibited by 14368 in a dose response manner in the presence of R1881 and showed only a basal level of transcriptional activity in the absence of androgen (FIG. 1D). In contrast, 14368 induced transcriptional activation of the T877A AR mutant at concentrations higher than 0.4 μM in both the presence and absence of R1881 (FIG. 1E). In addition, the agonistic effect was not observed at high concentrations of 14368 in R1-AD1 cells (in method described by Nyquist et al. 2013 PNAS 110: 17492-17497), which harbour a wild type form of the receptor (FIG. 1F). Together, these observations confirm that 14368 acts as an antagonist toward wild type AR while, at higher concentrations, it becomes an agonist in the presence of the T877A AR mutation.

9. Elimination of Partial Agonism of 4-(4-phenylthiazol-2-yl)morpholines

In order to eliminate the observed binding to the LBD of the human AR and the resulting partial agonistic action on the AR, we attempted to replace the phenyl fragment in the studied 4-(4-phenylthiazol-2-yl)morpholines with less hydrophobic heterocycles. A number of compounds were created containing various aromatic (14291), aliphatic (14403, 14406) and heterocyclic rings (14404, 14435, 14436, 14439) in place of the benzene fragment (see TABLE 2). These chemicals were custom-synthesized by the companies Life Chemicals (www.lifechemicals.com) and Enamine (www.enamine.net). Their purity and identity were confirmed by LC-MS and $^1$H NMR, respectively.

Figure 2:
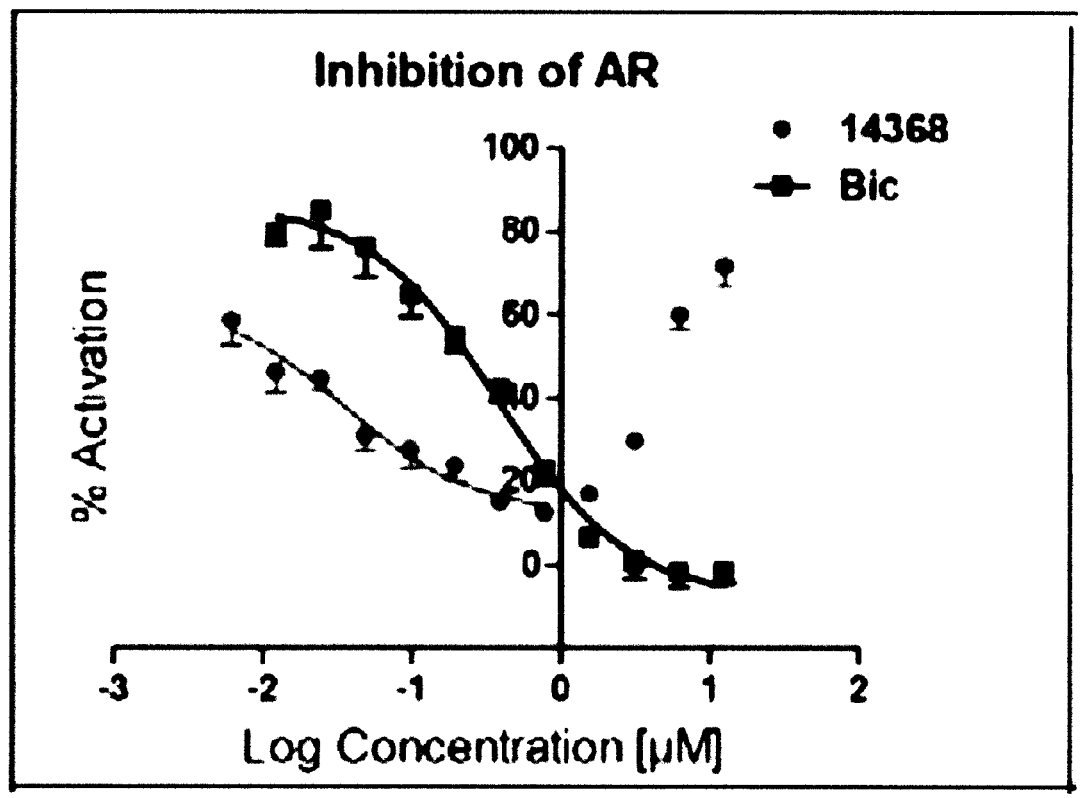
FIG. 2 Left panel: Dose-response curves of AR transcriptional inhibition by 14368, 14435, 14436, 14439, 14404 and bicalutamide (Bic) using eGFP AR transcriptional assay in the presence of 0.1 nM R1881. Right panel: Dose-response curves of androgen displacement by 14368, 14435, 14436, 14439, and 14404 using Polar Screen Androgen Receptor Competitor Green Assay Kit.
Figure 2:
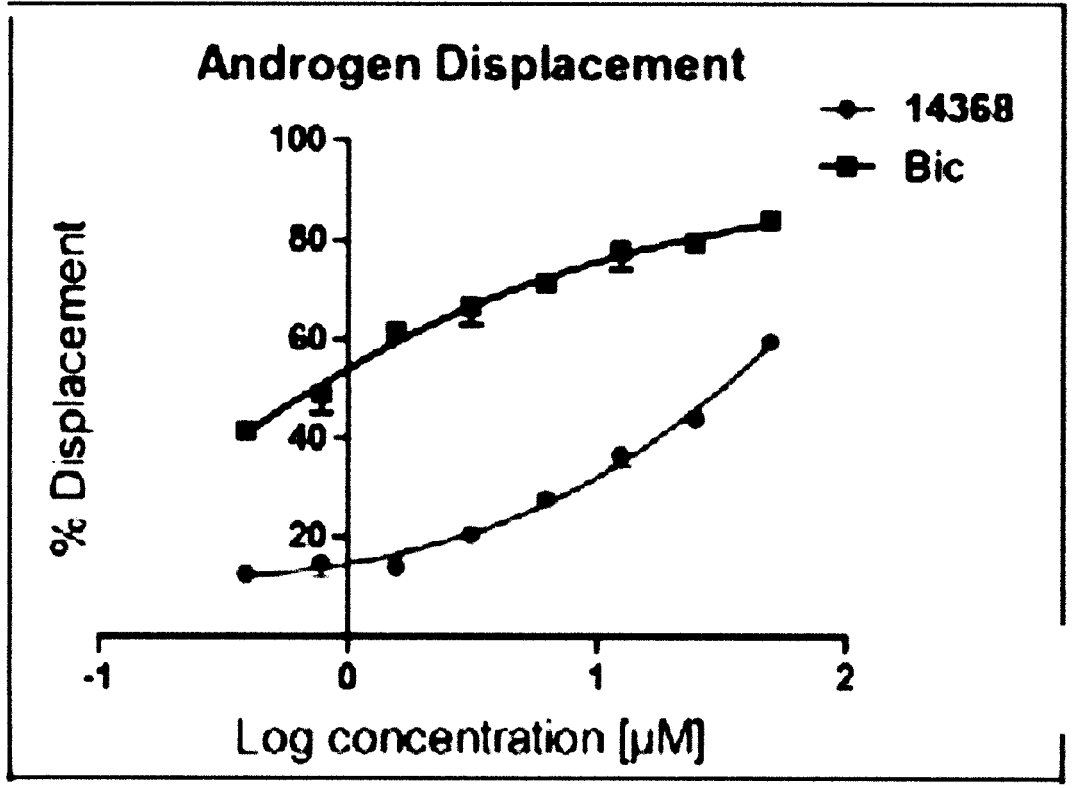
Figure 2:
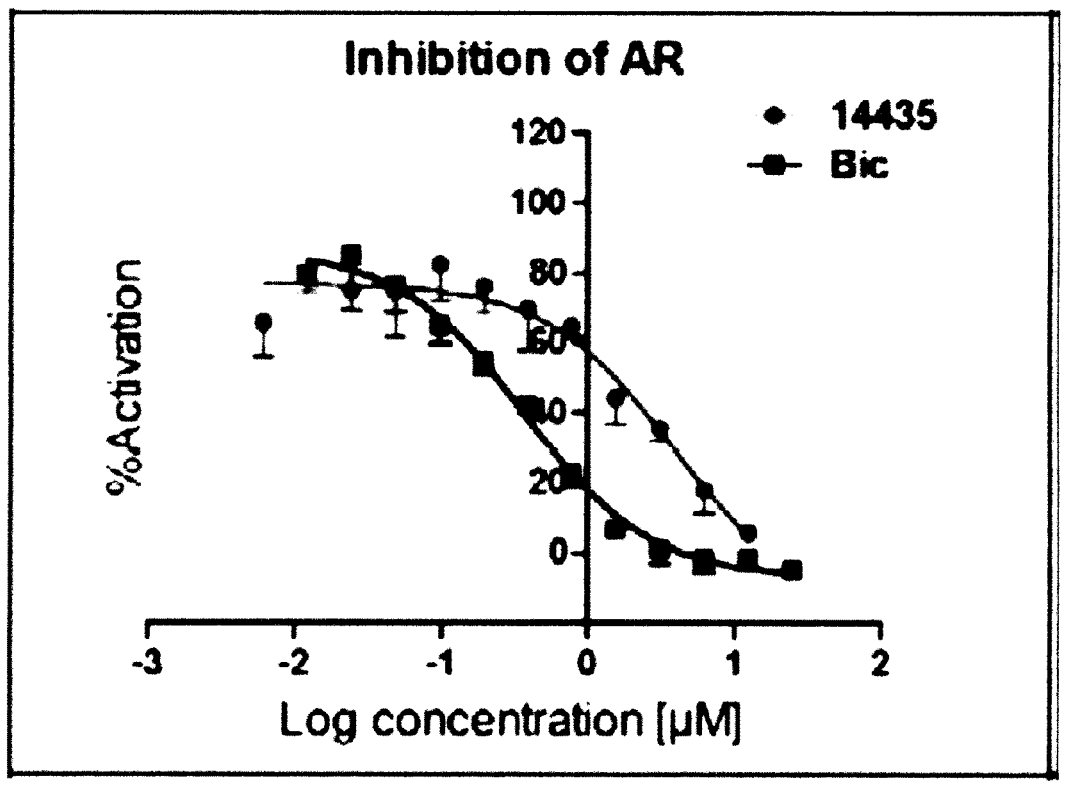
Figure 2:
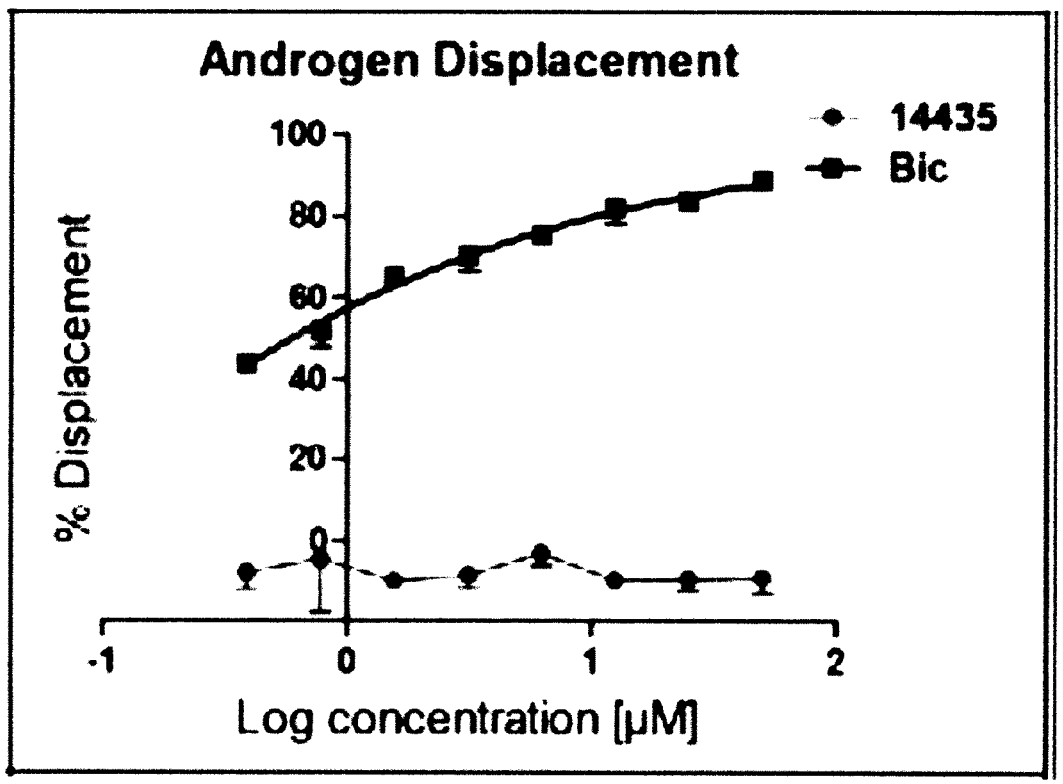
Figure 2:
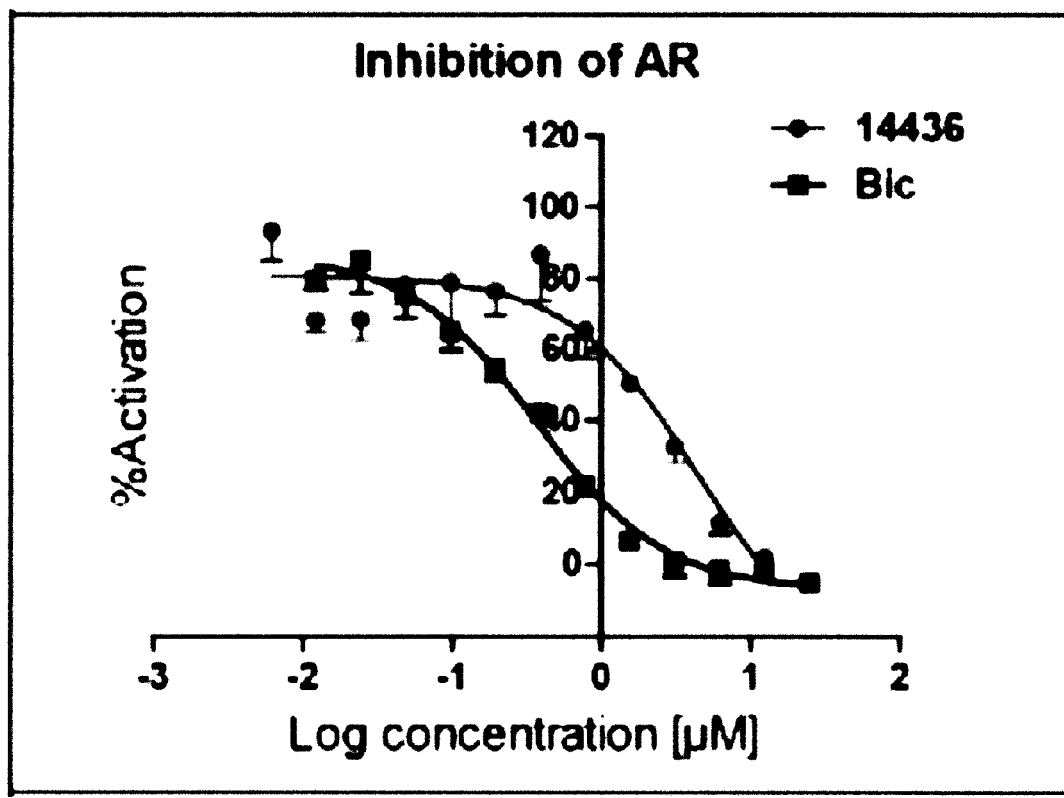
Figure 2:
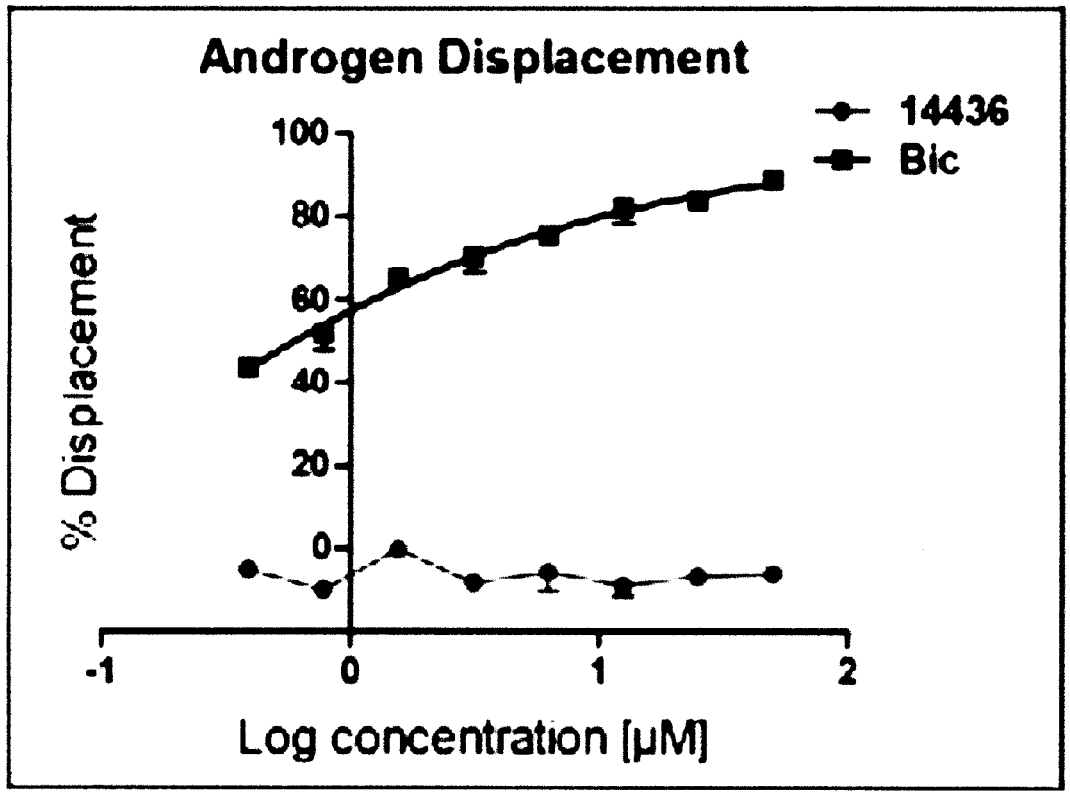
Figure 2:
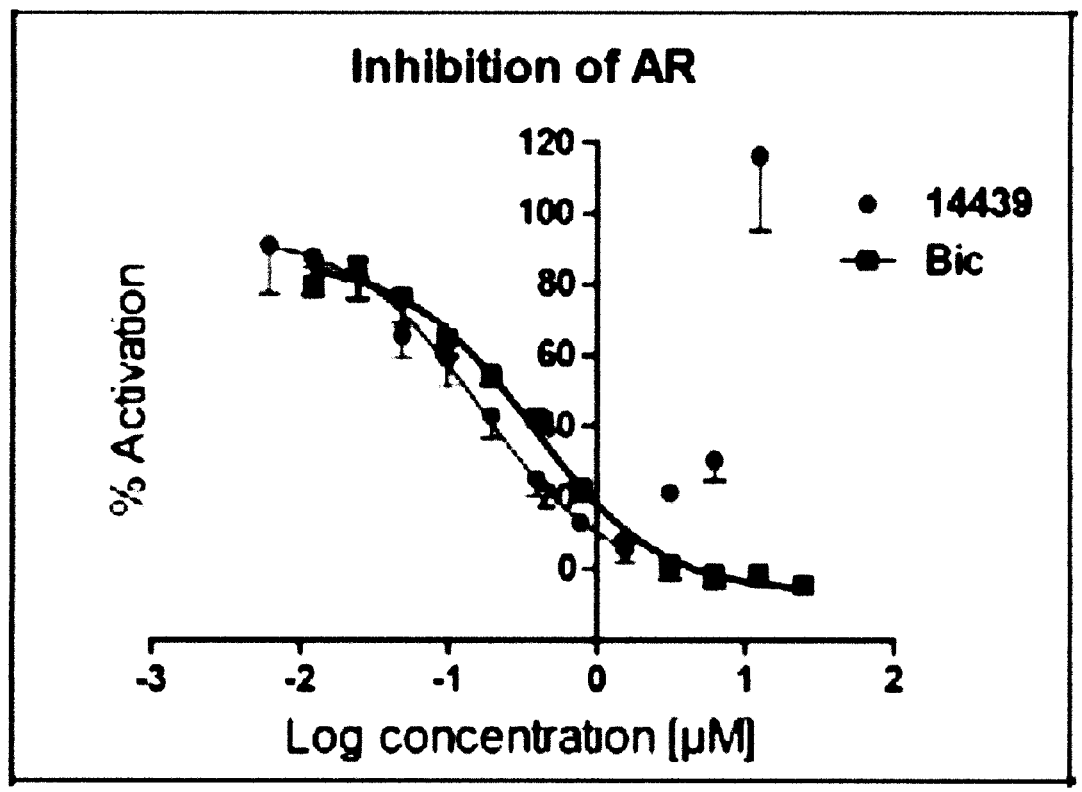
Figure 2:
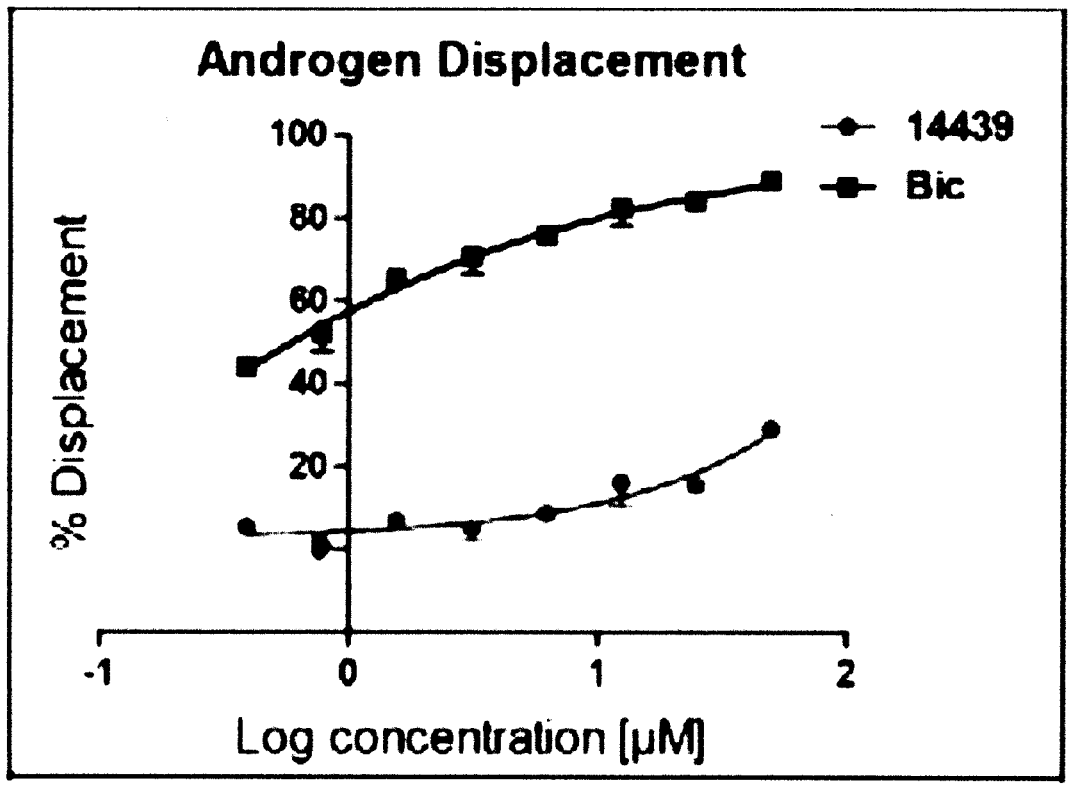
Figure 2:
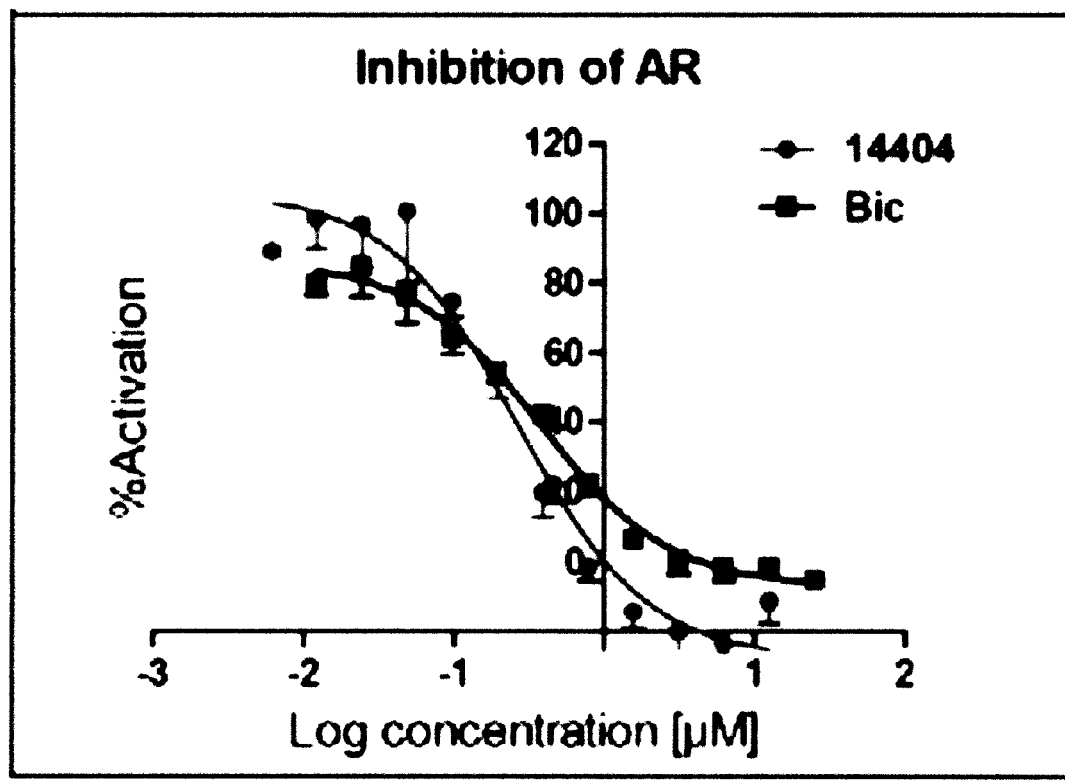
Figure 2:
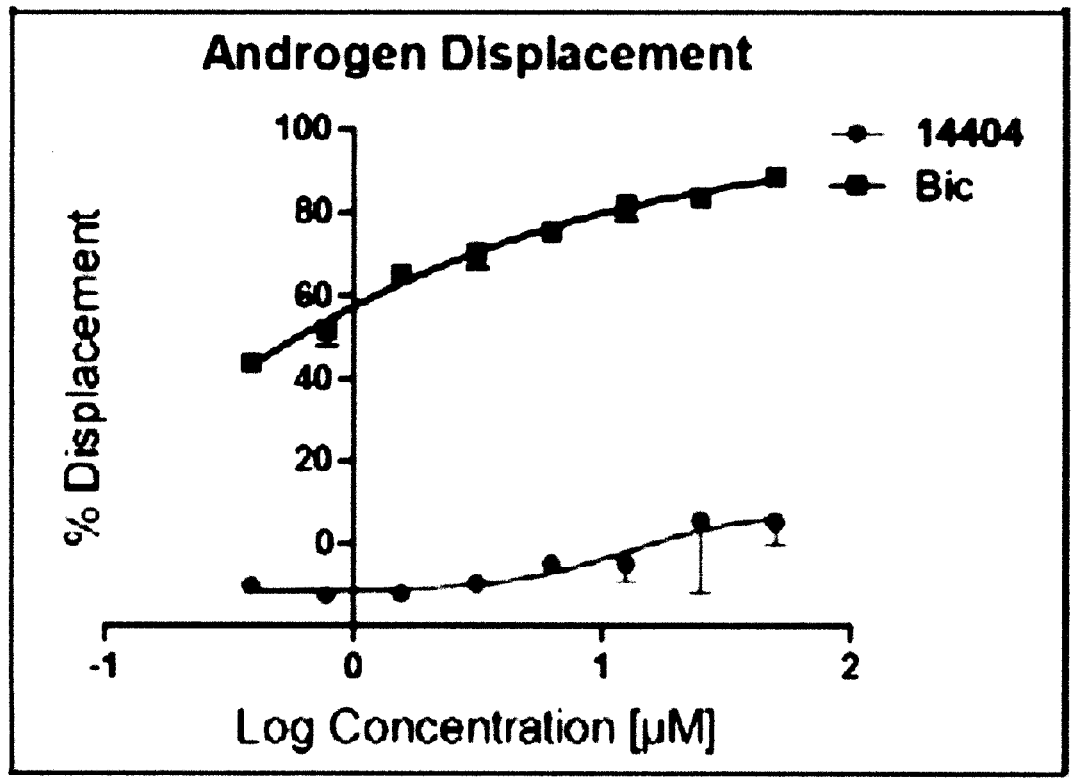
Figure 3A:
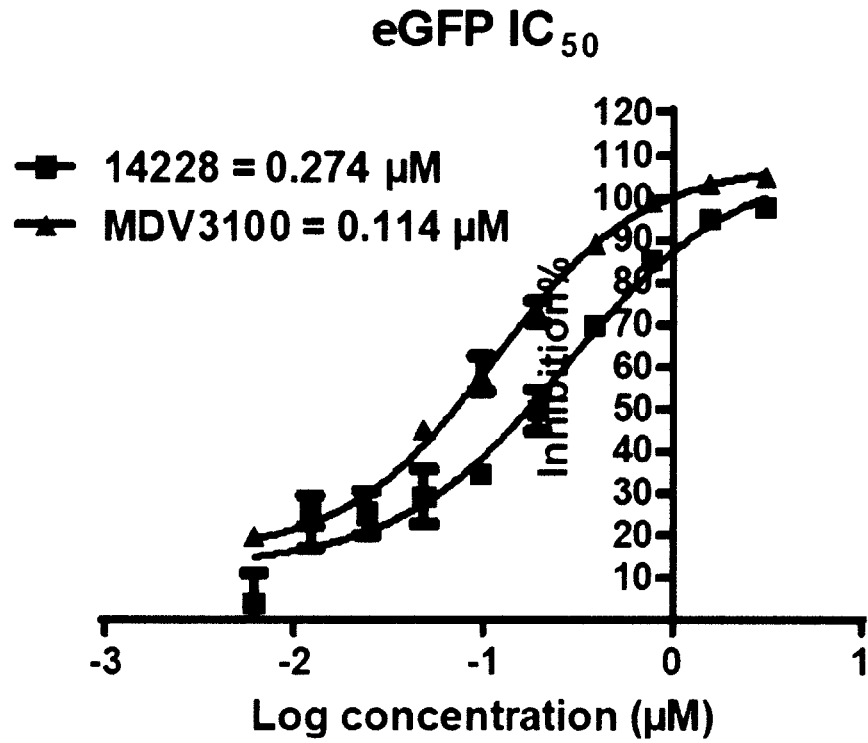
FIG. 3 shows in vitro profiles of 14228 including eGFP transcriptional activity, PSA, cell viability, androgen displacement and BLI.
Figure 3B:
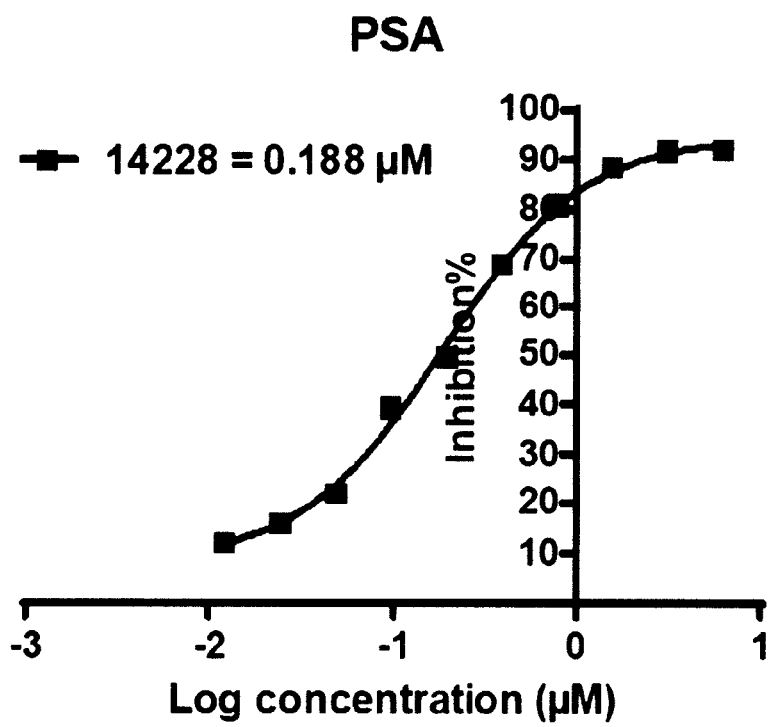
Figure 3C:
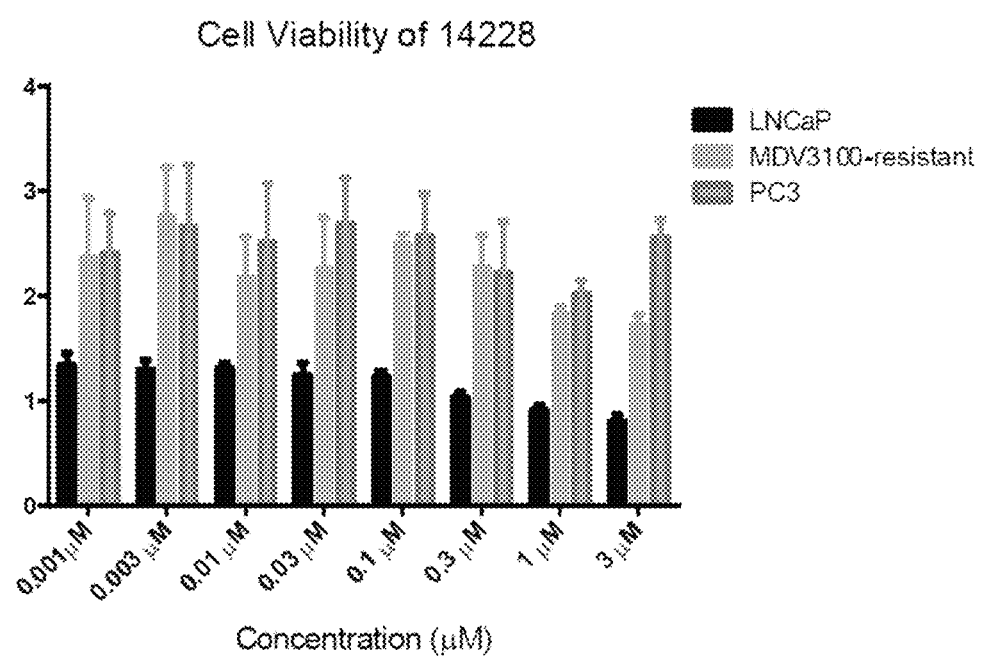
Figure 3D:
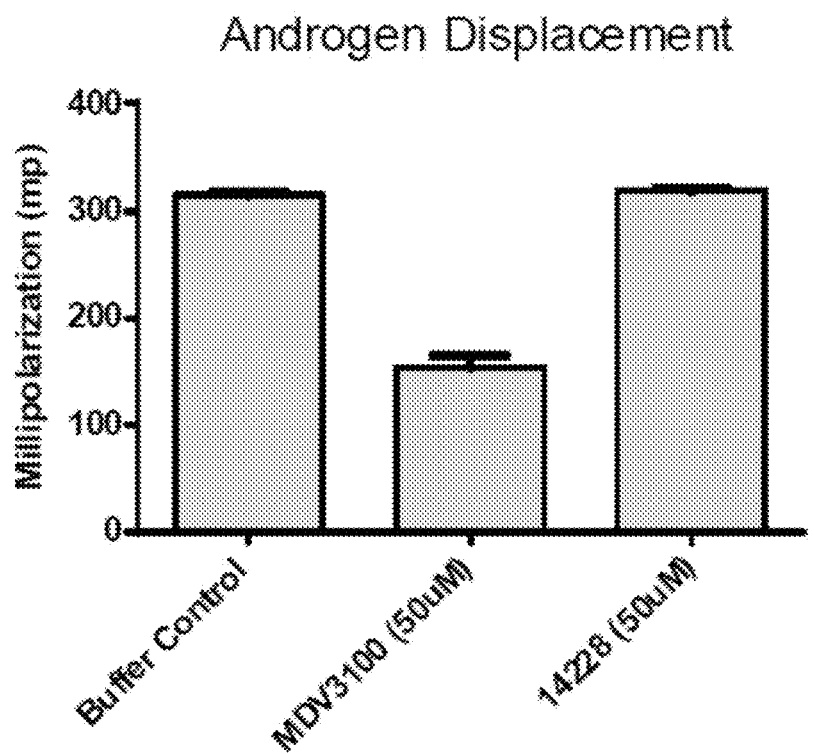
Figure 3E:
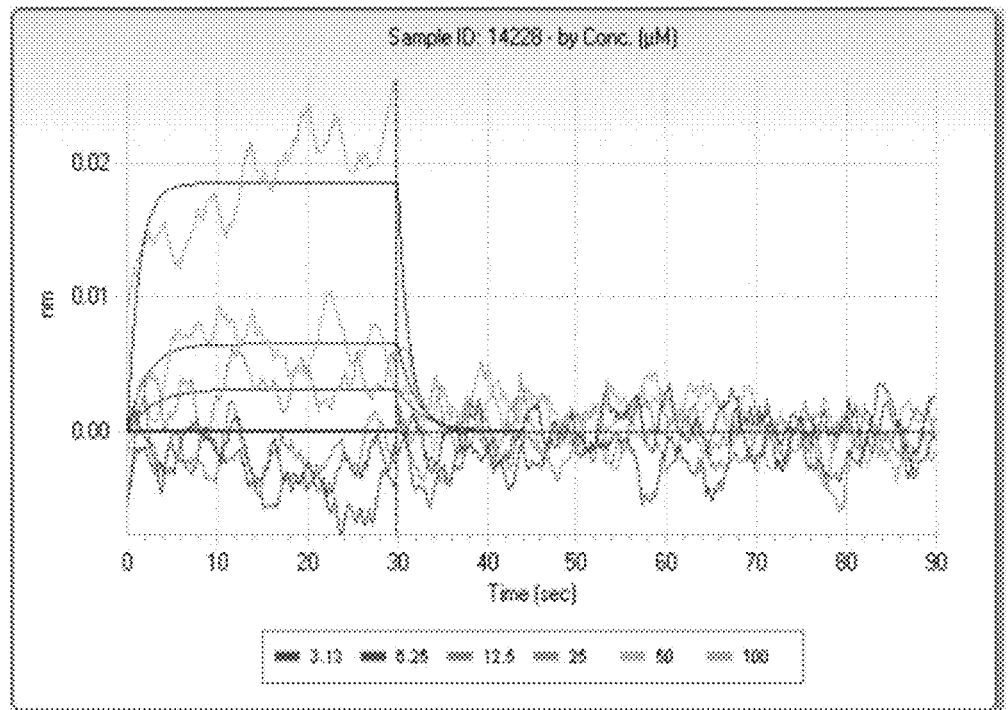

The ability of the above chemicals to displace DHT from the ABS site of recombinant wild type LBD was measured using a fluorescent polarization assay (PolarScreen™, Life Technologies) at various concentrations. The binding of 14368 to the ABS was detected in a concentration-dependent manner with the corresponding $IC_{50}$ established at ~30 μM (TABLE 2, FIG. 2). The replacement of the benzene ring with less hydrophobic heterocycles and bulkier aliphatic cycles could significantly reduce the DHT displacing ability of the compounds. Although some of the derivatives (14291, 14403, and 14406) lost their anti-AR activity, others, such as 14435, 14436, 14439 and 14404 maintained good potency against the mutated T877A form of AR, while showing no undesired partial agonistic effect.

TABLE 2

Structure and activity profiles of 4-(4-(3-fluoro-2-methoxyphenyl)thiazol-2-yl)morpholine derivatives

| ID | Structure | eGFP $IC_{50}$ (μM) | Androgen Displacement $IC_{50}$ (μM) |
|---|---|---|---|
| 14368 | 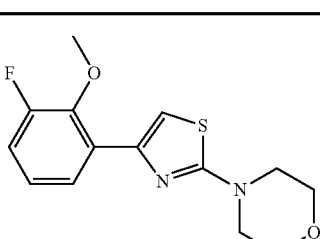 | 0.035 ± 0.02 | 31.28 |

TABLE 2-continued

Structure and activity profiles of 4-(4-(3-fluoro-2-methoxyphenyl)thiazol-2-yl)morpholine derivatives

| ID | Structure | eGFP IC$_{50}$ (μM) | Androgen Displacement IC$_{50}$ (μM) |
|---|---|---|---|
| 14404 | 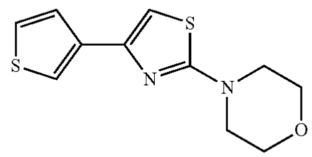 [SMILES: c1cc(-c2csc(N3CCOCC3)n2)cs1] | 0.27 ± 0.02 | No displacement |
| 14439 | 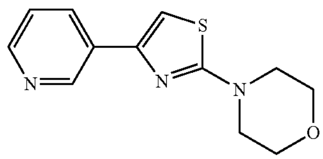 [SMILES: c1cncc(-c2csc(N3CCOCC3)n2)c1] | 0.16 ± 0.03 | low displacement |
| 14435 | 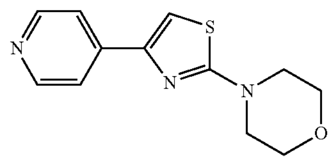 [SMILES: c1cc(-c2csc(N3CCOCC3)n2)ccn1] | 3.87 ± 1.26 | No displacement |
| 14436 | 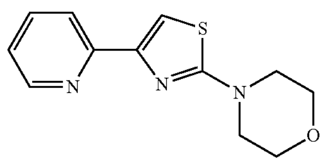 [SMILES: c1ccc(-c2csc(N3CCOCC3)n2)nc1] | 4.53 ± 0.26 | No displacement |
| 14403 | 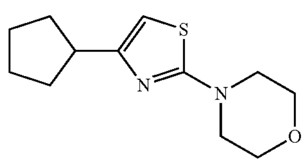 [SMILES: c1sc(N2CCOCC2)nc1C1CCCC1] | Low activity | — |
| 14406 | 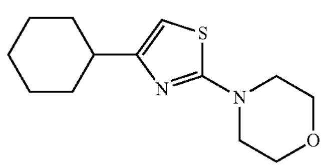 [SMILES: c1sc(N2CCOCC2)nc1C1CCCCC1] | Low activity | — |
| 14291 | 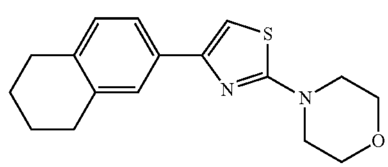 [SMILES: c1cc2c(cc1-c1csc(N3CCOCC3)n1)CCCC2] | Low activity | — |

10. Identification of a Potentially Drugable Binding Site on the AR DBD Surface

Figure 5:
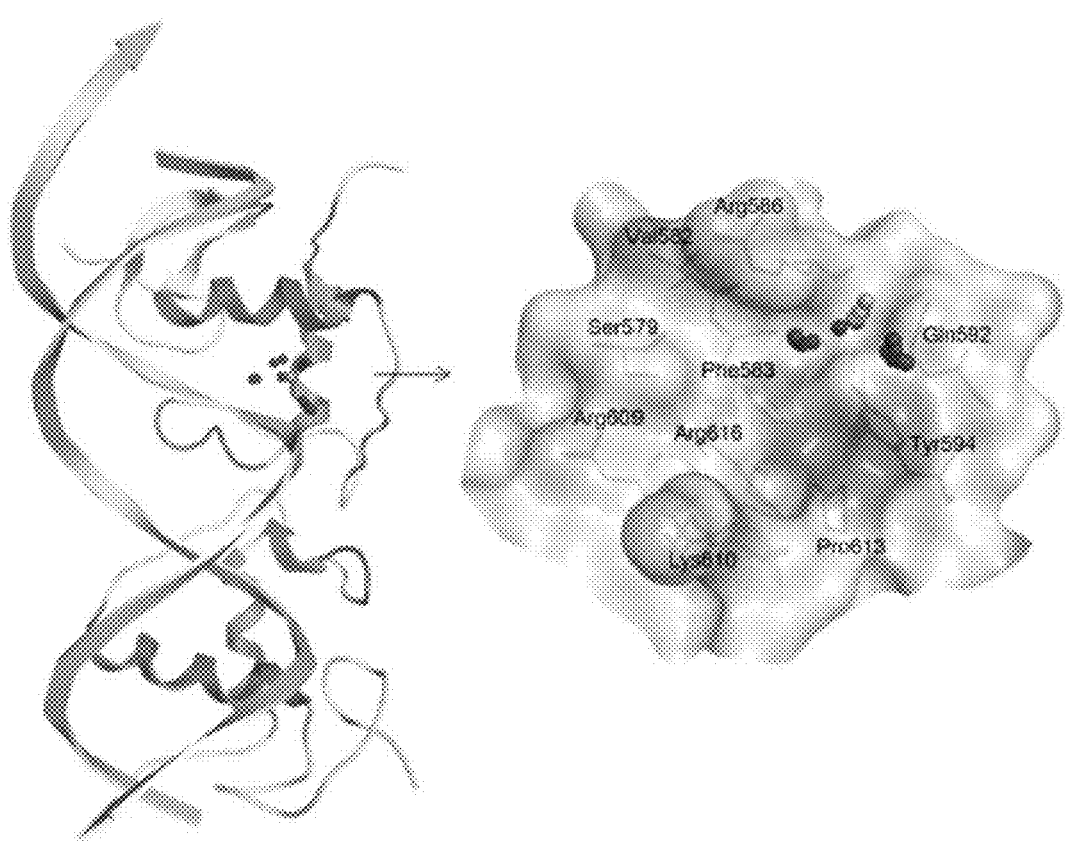
FIG. 5 shows a graphic representation of the predicted binding site on the human AR DBD homology model indicated by the dummy atoms. This site was enveloped by residues Ser579, Val582, Phe583, Arg586, Gln592, Tyr594, Arg609, Lys610 and Pro613 in human AR DBD, with the shaded areas between Phe583, Tyr594, Lys610 and Pro613, adjacent Val582 and to the right of Lys610 represent hydrophobic areas. Also, the shaded areas Arg586, Arg609, Arg616 and Lys610 represent polar areas.

The rat AR DBD dimer bound to two hexameric half-site AREs (PDB code: 1R4I) is the only crystal structure of the DBD region of the receptor available to date. As the sequences of rat and human AR DBDs are identical, the 1R4I structure was used as a template to build a homology model of the human AR DBD. The "hot spots" on the AR DBD dimer-ARE complex were predicted by a Site Finder module within the Molecular Operating Environment (MOE) 2011 package. A cavity underneath the P-box region of the AR DBD was considered as a potential site for small-molecule binding which may disrupt the AR DBD-ARE complex (FIG. 5). This cavity is mainly enveloped by residues Ser579, Val582, Phe583 and Arg586 of the recognition helix, as well as by polar residues Gln592 and Tyr594 belonging to the lever arm loop, and residues Pro613 and Arg616 from the other α-helix, together with the loop residues Arg609 and Lys610. The site is solvent exposed with specific residues predicted to play a key role in anchoring possible binding of small molecules. Thus, polar residues Ser579, Gln592 and Try594 around the periphery of the site could be characterised as available for hydrogen bonding, whereas Phe583 in the core of the site may provide additional hydrophobic interactions with potential binders.

11. Chemistry

All reagents and solvents were purchased from commercial suppliers and used without further purification unless otherwise stated. The reactions were monitored by thin layer chromatography (TLC) on precoated silica gel F254 plates (Sigma-Aldrich) with a UV indicator using ethylacetate/hexane (1:2 v/v). Yields were of purified product and were not optimized. The purity of the newly synthesized compounds was determined by LCMS analysis. The proton nuclear resonance (1H NMR) spectra were performed on a Varian GEMINI 2000 NMR spectrometer system with working frequency 400 MHz. Chemical shifts δ are given in ppm, and the following abbreviations are used: singlet (s), doublet (d), triplet (t), quartet (q), multiplet (m), and broad singlet (br s). All LC/MS data were gathered on an Agilent 1100 LC system. The compound solution was injected into the ionization source operating positive and negative modes with a mobile phase acetonitrile/water/formic acid (50:50:0.1% v/v) at 1.0 mL/min. The instrument was externally calibrated for the mass range m/z 100 to m/z 650.

Scheme 1. Schemes for the synthesis of heteroaryl derivatives 14449 (25), 14408 (27), 14404 (28), 14451 (31), 14402 (32), 14448 (34), 14450 (36), 14464 (38), 14468 (40), and 14447 (41).

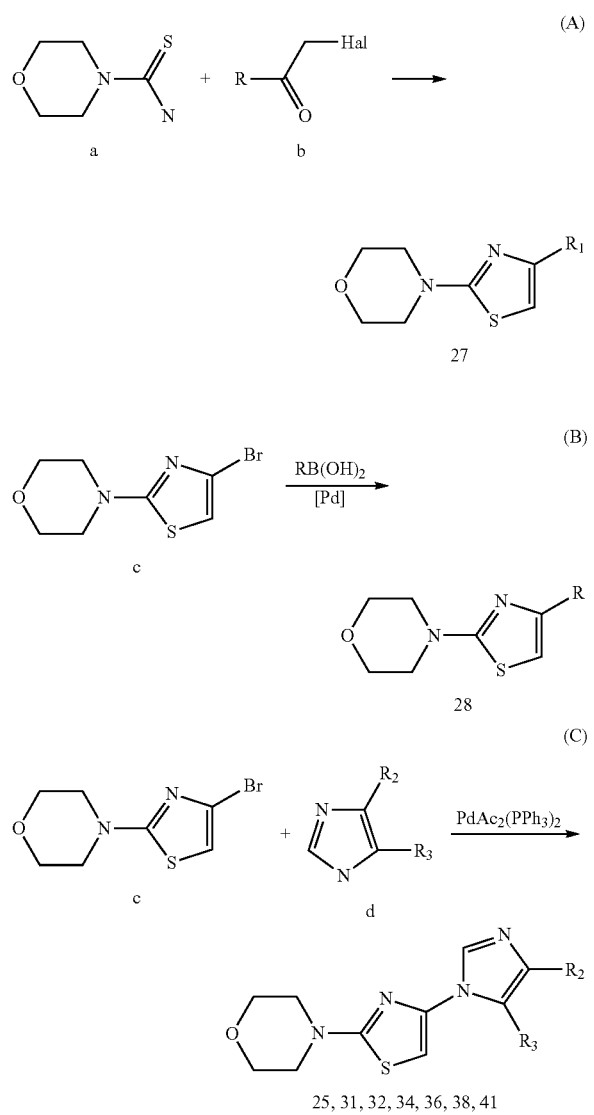

Reagents and conditions: (A) IPA, 100° C., 17-38%; (B) THF, H2O, K2CO3, PdCl2(PPh2C6H4SO3Na-m)2, 80° C., 54-73%; (C) toluene, PdAc2(PPh3)2, 110° C., 10 62%.

Synthetic Procedure for Compound 27 (Scheme 1(A))

A mixture of 10 mmol of thiourea (a) and 10 mmol of halogenated ketone (b) was dissolved in 10 mL of isopropanol. The formed solution was refluxed for 4h, and the organic solvent was removed under vacuum. The residue was treated with 20 mL of brine and extracted with 30 mL of ethylacetate (2 times). Combined organic layer was dried with sodium sulfate, filtered and evaporated. The obtained solid was purified by preparative HPLC (eluent EtOAc/Hexane=1/1) to give the final product as a solid.

4-(4-(4,5-dimethylthiophen-3-yl)thiazol-2-yl)morpholine (27)

$^1$H NMR (DMSO-d6, 400 MHz): 2.24 (3H, s), 2.36 (3H, s), 3.41-3.43 (4H, m), 3.73-3.76 (4H, m), 6.76 (1H, s), 7.33 (1H, MS (ESI): m/z (M+H)+281.1. Yield: 38%; purity 100% by LCMS.

Synthetic Procedure for Compound 28 (Scheme 1(B))

A mixture of 9.1 mmol of bromthiazole (Scheme 1(B), c), 11.8 mmol of corresponding boronic acid, 22.5 mmol of potassium carbonate and 0.1 mmol of a catalyst PdCl2(PPh2C6H4SO3Na-m)2 was dissolved in 100 mL of tetrahydrofuran and 16 mL of water. Then the reaction mixture was refluxed for 20 h.

After cooling it was extracted with 100 mL of ethylacetate. The organic layer was separated, dried with sodium sulfate, filtered and evaporated. The obtained residue was purified by preparative HPLC (eluent EtOAc/Hexane=1/1) to give the final product as a solid.

4-(4-(thiophen-3-yl)thiazol-2-yl)morpholine (28)

1H NMR (DMSO-d6, 400 MHz): 3.41-3.43 (4H, m), 3.72-3.74 (4H, m), 7.14 (1H, s), 7.49-7.55 (2H, m), 7.72-7.73 (1H, m). MS (ESI): m/z (M+H)+253.1. Yield: 54%; purity 95% by LCMS.

General Procedure for the Synthesis of Compounds 14449 (25), 14408 (27), 14404 (28), 14451 (31), 14402 (32), 14448 (34), 14450 (36), 14464 (38), 14468 (40), and 14447 (41) (Scheme 1(C))

A mixture of 4 mmol of bromthiazole (c), 12 mmol of corresponding imidazole (d), 0.1 mmol of catalyst PdAc2(PPh3) and 50 mL of toluene was refuxed for 24 h. After cooling the organic solvent was removed under vacuum. The resulting residue was purified by preparative HPLC (eluent EtOAc/Hexane=1/1) to give the final product as a solid. Compounds were additionally purified by reverse phase HPLC (eluent acetonitrile/water) with content of acetonitrile ranging from 20 to 80%.

4-4(4,5-dibromo-1H-imidazol-2-yl)morpholine (25)

$^1$H NMR (DMSO-d6, 400 MHz): 3.39-3.42 (4H, m), 3.70-3.73 (4H, m), 7.14 (1H, s), 7.80 (1H, s). MS (ESI): m/z (M+H)+395.0. Yield: 51%; purity: 98% by LCMS. M.p. 116-118C.

4-(4-(5-bromo-4-chloro-1H-imidazol-1-yl)thiazol-2-yl)morpholine (31)

$^1$H NMR (DMSO-d6, 400 MHz): 3.41-3.43 (4H, m), 3.71-3.73 (4H, m), 7.15 (1H, s), 8.16 (1H, s). MS (ESI): m/z (M+H)+351.0. Yield: 14%; purity 96% by LCMS.

4-(4-(4,5-dichloro-1H-imidazol-1-yl)thiazol-2-yl)morpholine (32)

$^1$H NMR (DMSO-d6, 400 MHz): 3.41-3.45 (4H, m), 3.71-3.73 (4H, m), 7.15 (1H, s), 8.14 (1H, s). MS (ESI): m/z (M+H)+305.1 Yield: 48%; purity 99% by LCMS.

4-(4-(4-chloro-1H-imidazol-1-yl)thiazol-2-yl)morpholine (34)

$^1$H NMR (DMSO-d6, 400 MHz): 3.42-3.44 (4H, m), 3.71-3.73 (4H, m), 6.97 (1H, s), 7.83 (1H, s), 8.17 (1H, s). MS (ESI): m/z (M+H)+271.1. Yield: 62%; purity 99% by LCMS.

4-(4-(4-bromo-5-chloro-1H-imidazol-1-yl)thiazol-2-yl)morpholine (36)

1H NMR (DMSO-d6, 400 MHz): 3.41-3.43 (4H, t), 3.70-3.72 (4H, m), 7.14 (1H, m), 8.15 (1H, s). MS (ESI): m/z (M+H)+351.0. Yield: 27%; purity 96% by LCMS.

4-(4-(4,5-diiodo-1H-imidazol-1-yl)thiazol-2-yl)morpholine (38)

$^1$H NMR (DMSO-d6, 400 MHz): 3.41-3.42 (4H, m), 3.71-3.73 (4H, m), 7.10 (1H, s), 8.10 (1H, s). MS (ESI): m/z (M+H)+488.9. Yield: 12%; purity 96% by LCMS.

4-(4-(4-chloro-5-iodo-1H-imidazol-1-yl)thiazol-2-yl)morpholine (40) $^1$H NMR (DMSO-d6, 400 MHz)

3.41-3.42 (4H, in), 3.70-3.71 (4H, m), 7.14 (1H, s), 8.14 (1H, s). MS (ESI): m/z (M+H)+397.5. Yield: 10%; purity 96% by LCMS.

4-(4-(4-bromo-1H-imidazol-1-yl)thiazol-2-yl)morpholine (41)

$^1$H NMR (DMSO-d6, 400 MHz): 3.42-3.43 (4H, m), 3.71-3.74 (4H, m), 6.98 (1H, s), 7.88 (1H, s), 8.18 (1H, s). MS (ESI): m/z (M+H)+316.1. Yield: 53%; purity 99% by LCMS.

Synthesis procedures for the rest compounds (4-4-(3,4-difluoro-2-methoxyphenyl)thiazol-2-yl)morpholine (26), 2-fluoro-6-(2-morpholinothiazol-4-yl)phenol (29), 4-(4-(4-fluoro-2-methoxyphenyl)thiazol-2-yl)morpholine (30), 2,3-difluoro-6-(2-morpholinothiazol-4-yl)phenol (33), 5-fluoro-2-(2-morpholinothiazol-4-yl)phenol (35), 4-(5-methyl-4-phenylthiazol-2-yl)morpholine (37), 4-(4-pyridin-2-yl)thiazol-2-yl)morpholine (39), 4-(4-(pyridine-4-yl)thiazol-2-yl)morpholine (42), 3-fluoro-4-methoxyl-5-(2-morpholinothiazol-4-yl)phenol (43) and 4-(4-(3-fluoro-2-methanesulfonyl-phenyl)-thiazol-2-yl)morpholine (44), and compounds (72-84) follow from the above.

Compounds described herein may be synthesized as described herein, using modified methods described herein or by methods known to a person of skill in the art.

ADDITIONAL REFERENCES

Lack, N. A., P. Axerio-Cilies, et al. (2011). Journal of Medicinal Chemistry 54(24):8563-73.
Tavassoli, P., R. Snoek, et al. (2007). Prostate 67(4): 416-426.

The following examples (i.e. 12-17) are set out in more detail in Dalai K. et al. "Selectively Targeting the DNA-binding Domain of the Androgen Receptor as a Prospective Therapy for Prostate Cancer" THE JOURNAL OF BIOLOGICAL CHEMISTRY VOL. 289, NO. 38, pp. 26417-26429, Sep. 19, 2014 (published online 1 Aug. 2014).

12. Luciferase Reporter Assay

Using a luciferase reporter assay in PC3 cells driven by the ARR3tk probasin-based promoter (Snoek, R. et al. (1998) Differential transactivation by the androgen receptor in prostate cancer cells. *Prostate* 36, 256-263), two compounds predicted to bind to the AR-DBD showed dose-dependent inhibition of the transiently expressed full-length human AR (data not shown, 14228 and 14449, IC50=2.36 and 0.340 µM, respectively) without affecting AR protein expression (data not shown). 14337 (pyrvinium)

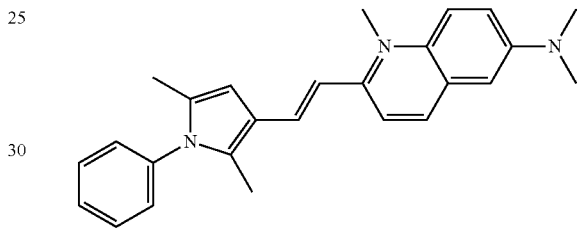

was recently reported to inhibit the full-length and splice variant AR forms by targeting the DBD (Lim, M. et al. (2014) Ligand-independent and tissue-selective androgen receptor inhibition by pyrvinium. *ACS Chem. Biol.* 9, 692-702), and could also inhibit AR transcriptional activity (data not shown, IC50=0.194 µM). Control experiments demonstrate that 14449 could inhibit the AR to level comparable with enzalutamide (data not shown, IC50=0.314 µM). Western blots against PARP confirm that compound treatment did not affect total PARP levels nor did it generate any PARP cleaved product, with the exception of 14337 (data not shown). These results indicate that pyrvinium (14337) strongly induces apoptosis, whereas DBD inhibitors (14228/14449) exhibit little or no toxicity.

To validate the site of action of AR-DBD binders, we introduced point mutations at residues that are predicted to interact with the lead compounds. Two positions (Tyr-594 and Gln-592) that were identified in the region with amino acid differences among related nuclear receptors (data not shown) could bear aspartate substitutions without abolishing full-length AR activity. Whereas the Y594D and Q592D mutants could be inhibited by enzalutamide, luciferase expression was not affected by 14228 and only by high concentration (≥25 µM) of 14449 (data not shown). In contrast, pyrvinium strongly inhibited both AR mutants (data not shown), suggesting that the compound engages residues other than Tyr-594/Gln-592 in the surface-exposed pocket or instead binds to a different location on the DBD surface. Western blot analysis confirms that the expression of mutant AR proteins was not changed by drug inhibition (data not shown). Introducing an acidic residue at these positions may prevent hydrophobic interactions necessary for supporting compound binding.

Figure 6:
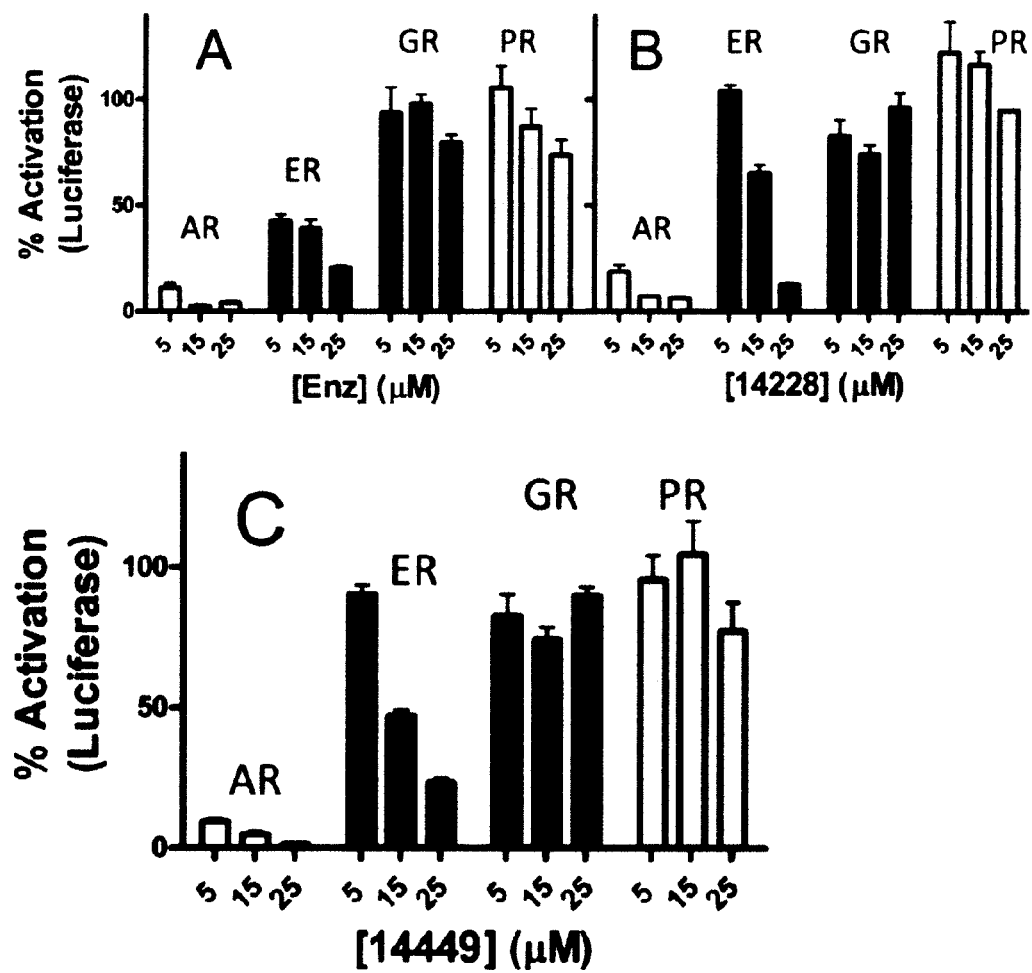
FIG. 6 shows a bar graph of a selection of DBD-interacting compounds having specificity for AR, wherein Enzalutamide (enz) is shown in graphs (A), 14228 (B), and 14449 (C) tested at the indicated concentrations in luciferase assays against transiently expressed AR, GR, and PR or against endogenous ER-_ in MCF-7 cells and AR, GR, and PR activity was assessed with the ARR3tk-luciferase reporter. MCF-7 cells include a stably transfected estrogen-response element-luciferase gene. 100% refers to luciferase activity of each receptor with 0.1% DMSO only (Errors bars represent the mean_S.D. six replicates. enz, enzalutamide).

In addition to introducing a charged amino acid into the DBD, we also tested Y594A and Q592A mutants, both of which could be inhibited by 14228/14449 but with significantly higher IC50 values (data not shown, ~3-6 μM) compared with wild type AR (data not shown). It is possible that removing the Gln or Tyr side chains creates additional space in the pocket to allow compound entry but reduced ability to inhibit AR activity. The resulting increase in IC50 values further supports the importance of Tyr-594 and Gln-592 residues to compound binding that is compromised when their side chains are removed. To determine whether our compounds cross-react with the DBDs of related nuclear receptors, we performed assays with full length ER, GR, and PR (FIG. 6). Luciferase constructs contained the appropriate response region for the corresponding nuclear receptor with $ARR_3tk$ used for AR/GR/PR and estrogen-response element for ER. 14228/14449 showed inhibition of ER transcriptional activity at concentrations higher than 5 μM (FIGS. 6, B and C, black bars) but were several fold less effective when compared with inhibition of the AR (white bars). All three tested compounds were completely ineffective on the transcriptional activity of full-length GR and PR, even when administered at 25 μM concentration (FIG. 6, dark gray and light gray bars, respectively). Remarkably, enzalutamide showed considerable cross-reactivity against the full-length ER, approaching inhibition levels comparable with that against the AR (FIG. 6, black bars). These data suggest that the developed compounds possess potent inhibitory effects against the AR, bind to the intended target site on the ARDBD, and show little or no cross-reactivity.

Figure 7:
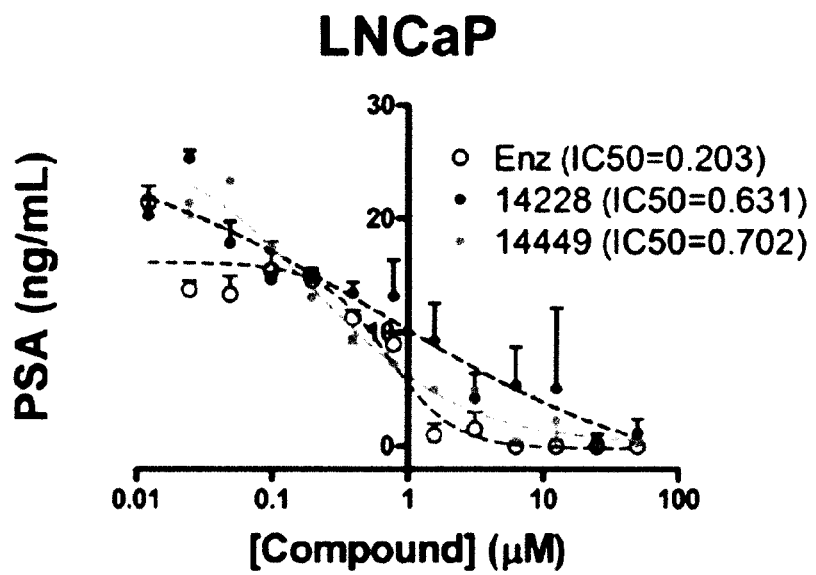
FIG. 7 shows the effect of DBD-interacting compounds on the expression of AR target genes, A is a line plot showing the secreted PSA the from LNCaP cells that were treated with 1 nM R1881 and compounds (i.e. enzalutamide, 14449 and 14228) for 2 days at the indicated concentrations, with the secreted PSA quantified by analyzing 150 µl of cell culture media from each well from two independent experiments. B is a bar graph showing gene expression changes of AR target genes and a non-androgen-responsive gene (α-actin, ACTB) in the presence of R1881, compound 14449, and enzalutamide (Enz). *=a significant reduction in gene expressions (p value<0.05) based on two-sample t test between 14449+R1881 and DMSO+R1881 and between enzalutamide+R1881 and DMSO+R1881.
Figure 7:
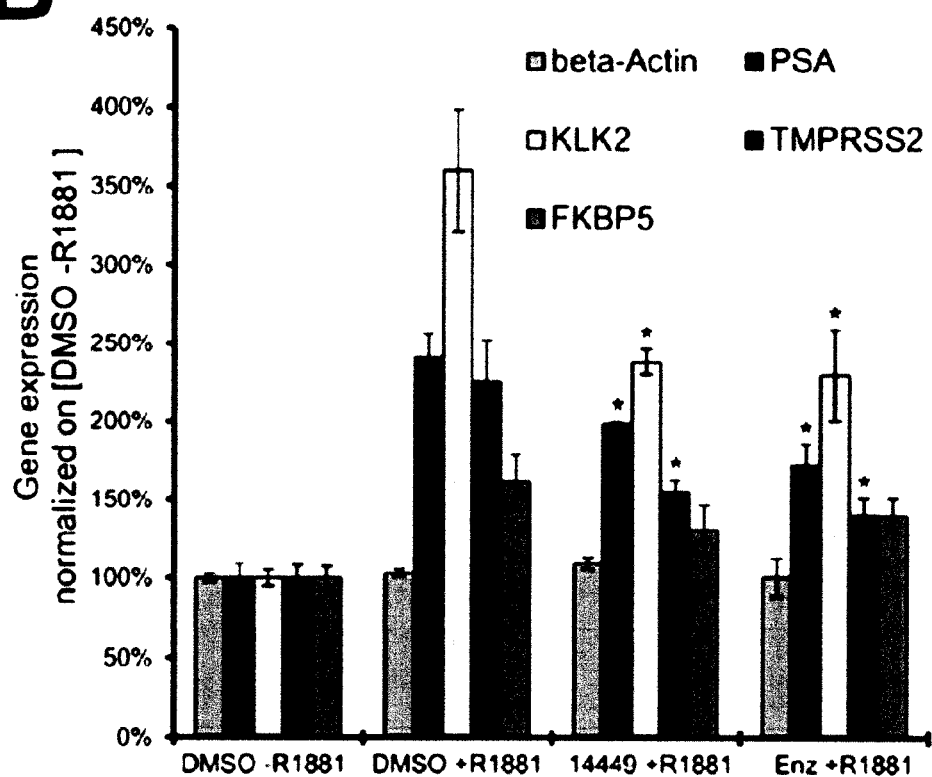

13. DBD-Interacting Compounds Down-Regulate Expression of Androgen-Responsive Genes in LNCaP Cells To assess the ability of 14228/14449 to block transcription of naturally occurring AR-regulated genes, LNCaP cells were treated simultaneously with R1881 and compounds, followed by measurement of secreted PSA (FIG. 7A). The results show a dose-dependent inhibition by 14228/14449 and enzalutamide with corresponding IC50 values all established at sub-micromolar concentrations.

Using a chemo-genomic approach (Bredel, M., and Jacoby, E. (2004) Chemogenomics: an emerging strategy for rapid target and drug discovery. *Nat. Rev. Genet.* 5, 262-275), a more extensive analysis of gene expression was conducted using the lead inhibitor 14449. To determine any effect on the expression of androgen- or genotoxin-responsive genes, LNCaP cells were treated with 14449 (400 nM) or enzalutamide (120 nM), in the presence of R1881, to compare transcriptional responses using Agilent™ gene expression microarrays (FIG. 7B). Several well known AR target genes (Nelson, P. S. et al. (2002) The program of androgen-responsive genes in neoplastic prostate epithelium. *Proc. Natl. Acad. Sci. U.S.A.* 99, 11890-11895; and Magee, J. A. et al. (2006) Direct, androgen receptor-mediated regulation of the FKBP5 gene via a distal enhancer element. *Endocrinology* 147, 590-598), which include KLK3 (PSA), KLK2, TMPRSS2, and FKBP5, increased in gene expression under the presence of R1881 (comparing DMSO+R1881 against DMSO−R1881) with fold changes of 2.42, 3.60, 2.25, and 1.61, respectively. Following treatment with 14449+R1881, gene expressions of KLK3, KLK2, and TMPRSS2 were all reduced significantly with fold changes of 0.82, 0.66, and 0.69, respectively, as compared with R1881 treatment only. The reduction of expression of these AR target genes by 14449 is comparable with that by enzalutamide with fold changes of 0.71, 0.64, and 0.62. There was a decrease (fold change 0.81) of FKBP5 expression by 14449; however, the p value of 0.08 did not meet the 0.05 cut-off based on the two-sample t test, likely due to the small sample size. Both compounds and enzalutamide showed no effect on the expression of a nonandrogen regulated gene, β-actin (ACTB). To identify other down-regulated genes, the following criteria were applied to all the 50,737 transcripts measured on the Agilent™ microarrays: p value<0.05 based on two-sample t test and 2) fold change≤0.85. A total of 354 genes were downregulated by 14449, among which 112 were also downregulated by enzalutamide. The overlap of down-regulated genes between the two compounds was significant with a p value of Fisher's exact test less than 2.20E-16 and odds ratio of 45.86. In addition, the list of down-regulated genes by either 14449 and/or enzalutamide was compared with a total of 86 genes that have been previously shown to be up-regulated by androgens in LNCaP cells (Nelson, P. S. et al. (2002) The program of androgen-responsive genes in neoplastic prostate epithelium. *Proc. Natl. Acad. Sci. U.S.A.* 99, 11890-11895). 12 of the 354 down-regulated genes by 14449 are up-regulated by androgens (significant overlap: p value=2.73E-08, odds ratio=9.55), and 15 of the 314 down-regulated genes by enzalutamide are up-regulated by androgens (significant overlap: p value=3.34E-12, odds ratio=14.27). The genes KLK2, KLK3 (PSA), and TMPRSS2 are among 10 genes that are upregulated by androgens, but down-regulated by both 14449 and enzalutamide. The two sets of mutually exclusive down-regulated genes resulting from 14449 or enzalutamide treatment indicates profoundly different mechanisms of action of each compound to inhibit AR signaling. Finally, to identify any potential genotoxic effect from the two chemicals, up-regulated genes by either 14449 or enzalutamide were compared with a list of 31 genes, the expression of which has previously been shown to increase in the presence of genotoxins (Ellinger-Ziegelbauer, H. et al. (2009) Characterization and interlaboratory comparison of a gene expression signature for differentiating genotoxic mechanisms. *Toxicol. Sci.* 110, 341-352). This set of genotoxin-responsive genes includes a number of p53 target genes and others involved in apoptosis, DNA repair, DNA damage response, and stress response. None of the genotoxin-responsive genes showed any significant change of expression by 14449. Three known representative genes that were unaffected included CASP1 (caspase 1, apoptosis, fold change=1.00, p value=0.73), XPC (xeroderma pigmentosum complementation group C, DNA repair, fold change=1.03, p value=0.59), and ATF3 (activating transcription factor 3, stress response, fold change 0.99, p value=0.89). Collectively, the results demonstrate that the developed AR DBD inhibitors can significantly down-regulate expression of known AR-regulated genes to levels comparable with that by enzalutamide, with no cytotoxicity induced.

14. DBD-Interacting Compounds Inhibit Transcriptional Activity of AR Splice Variants Because most AR splice variants retain the DBD domain, we tested for inhibition of the transcriptional activity of AR-V7. Using the same luciferase reporter assay, the activity of transiently expressed AR-V7 was reduced with increasing concentrations of 14228/14449 or pyrvinium without altering AR-V7 expression (data not shown).

Control experiments with enzalutamide showed no effect on AR-V7 activity (data not shown) and are consistent with the absence of the LBD from this variant. Notably, the compounds did not achieve complete inhibition and were less effective against the transcriptional activity of AR-V7 (IC50=4-8 μM) when compared with inhibition of the full-length receptor. We reasoned that the DBDs of the full-length and splice variant ARs would share a similar protein structure. Accordingly, we introduced the Y594D mutation into the AR-V7 coding sequence to determine whether this mutation could abolish drug inhibition. The transcriptional activity of AR-V7Y594D could not be inhibited by 14228/14449 (data not shown), suggesting the binding location of the compounds are similar on all forms of the AR. As with the full-length AR bearing this mutation, AR-V7Y594D could still be strongly inhibited by pyrvinium (data not shown).

Transient AR-V7 expression may not reflect physiological protein concentrations in cells. To investigate the effect of our compounds on endogenous expression levels, we used a pair of isogenic cell lines that express either full-length AR (R1-AD1 or the AR v567es variant (R1-D567). R1-D567 cells were derived from the R1-AD1 cell line by TALEN-mediated deletion of AR exons 5-7, reflecting an AR gene rearrangement discovered in patient-derived LuCaP 86.2 xenograft tissue (Nyquist, M. D. et al. (2013) TALEN-engineered AR gene rearrangements reveal endocrine uncoupling of androgen receptor in prostate cancer. *Proc. Natl. Acad. Sci. U.S.A.* 110, 17492-17497). Following transfection of ARR3tk-luciferase plasmid into these cell lines, 14228/14449 could inhibit both wild type and AR v567es transcriptional activity with increasing concentrations (data not shown). Western blots demonstrate no effect of the compounds on protein expression of either form of the AR (data not shown). We also performed Western blots for the naturally occurring AR-regulated FK506-binding protein 5 (FKBP5). FKBP5 protein expression was reduced in R1-AD1 and R1-D567 cells following treatment with 14228/14449, whereas enzalutamide treatment only affected R1-AD1 cells expressing the full-length AR (data not shown). These results agree with the observed reduction in FKBP5 mRNA levels after siRNA knockdown of v567es in R1-D567 cells (Nyquist, M. D. et al. (2013) TALEN-engineered AR gene rearrangements reveal endocrine uncoupling of androgen receptor in prostate cancer. *Proc. Natl. Acad. Sci. U.S.A.* 110, 17492-17497).

15. DBD-Interacting Compounds do not Impede AR Nuclear Translocation

Enzalutamide and other inhibitors of the ARLBD are thought to block nuclear localization of the AR, thereby preventing it from initiating transcription (Ferraldeschi, R., et al. (2013) Abiraterone and novel antiandrogens: overcoming castration resistance in prostate cancer. *Annu. Rev. Med.* 64, 1-13; and Rathkopf, D., and Scher, H. I. (2013) Androgen receptor antagonists in castration-resistant prostate cancer. *Cancer J.* 19, 43-49). In contrast to this mechanism of conventional anti-androgens, we predicted that DBD-interacting compounds would exert their effect on nuclear AR. To test this idea, we transfected PC3 cells with plasmids encoding YFP-tagged full-length AR (yellow fluorescent protein, YFP-AR-van Royen, M. E. et al. (2012) Stepwise androgen receptor dimerization. *J. Cell Sci.* 125, 1970-1979) and splice variant AR-V7 (YFP-V7). Both YFP-AR and YFP-V7 were able to drive luciferase expression and could be inhibited by 14228/14449, demonstrating that the YFP tag did not affect AR transcriptional activity or compound inhibition (data not shown). Upon treatment with R1881 and enzalutamide, confocal microscopy images revealed considerable levels of YFP-AR in the cytosol compared with control experiments (data not shown). Conversely, 14228/14449 did not prevent R1881-stimulated nuclear localization of YFP-AR with no fluorescence signal observed in the cytosol (data not shown). Control experiments show that enzalutamide or 14228/14449 could not stimulate any nuclear localization in the absence of R1881 (data not shown). YFP-V7 completely localized in the nucleus under all conditions, even without R1881 (data not shown), which agrees with the known property of splice variants to spontaneously undergo nuclear translocation (Watson, P. A. et al. (2010) Constitutively active androgen receptor splice variants expressed in castration-resistant prostate cancer require full-length androgen receptor. *Proc. Natl. Acad. Sci. U.S.A.* 107, 16759-16765). Together, these results suggest that our compounds influence the activity of the AR and its splice variants inside the cell nucleus, consistent with directly affecting DBD functions.

16. Compounds Diminish DNA Binding by the AR at the Chromatin Level and In Vitro Since the developed AR DBD inhibitors are predicted to bind near the protein-DNA interface on the AR-DBD, the compounds should affect AR binding to the enhancers (bearing AREs) of androgen-regulated genes. Following ChIP analysis (AR-N20 antibody) of chromatin from LNCaP cells treated with R1881 and compounds, both 14428 and 14449 reduced AR pulldown of the PSA and FKBP5 enhancer compared with R1881 treatment alone (data not shown). Control experiments revealed no pull down of the enhancers in the absence of R1881, after enzalutamide treatment or under any condition with the GAPDH promoter negative control.

Given that our compounds do not block nuclear translocation (data not shown), the ChIP results suggest 14228/14449 blocks the interaction of the AR with androgen-response elements in the nucleus. To directly probe DNA interactions, we explored the binding of recombinant AR-DBD with an oligonucleotide containing two hexameric AREs. Purified human AR-DBD and hinge region (residues 558-689, AR-DBD+hinge) were incubated with ARE 42-bp double-stranded stranded DNAs (dsDNA) and analyzed by native-PAGE. The protein was able discriminate between the ARE and a scrambled control (data not shown), but 14228/14449 could not prevent protein-DNA complex formation (data not shown). We speculated that gel shift may be insufficient to detect small but significant changes in DNA binding because the acrylamide matrix might dissociate the hydrophobic compound from the protein surface. To circumvent this limitation, we used a biotinylated AR-DBD linked to streptavidin-coated sensors for use in biolayer interferometry analysis. The biotinylated DBD was exposed to the ARE oligonucleotide in the presence of DMSO or compounds. The observed association kinetics revealed a significantly slower rate of dsDNA binding in the presence of 14228/14449 as compared with enzalutamide and DMSO controls, although dissociation remained relatively unchanged (data not shown). The same experiment performed with the biotinylated AR-DBD bearing the Y594D mutation revealed the directly and demonstrate specific inhibition of transcriptional activity despite high sequence conservation with other receptors. Related DBD domains from ER, GR, and PR may have enough structural differences with the AR-DBD such that the surface-exposed pocket is either changed or absent. Remarkably, Gln-592 of the AR is not conserved with any other related nuclear receptor. This residue, along with Tyr-594, might contribute to the unique shape and chemistry of the surface-exposed pocket on the DBD, and consequently, when mutated, counteracts drug inhibition.

The properties of a surface-exposed or buried pocket may predictably be altered through mutagenesis. For example, a single amino acid substitution of T877A converts AR antagonists into agonists (Taplin, M. E. et al. (1995) Mutation of the androgenreceptorgene in metastatic androgen-independent prostate cancer. *N. Engl. J. Med.* 332, 1393-1398), and this conversion can be rationalized by crystal structures of AR-LBD in complex with drugs (Lallous, N. et al. (2013) Targeting alternative sites on the androgen receptor to treat castration-resistant prostate cancer. *Int. J. Mol. Sci.* 14, 12496-12519). Here, substitution of aspartic acid or alanine residues at Tyr-594 and Gln-592 of the AR had a dramatic effect on the ability of two compounds to inhibit AR transcriptional activity, providing compelling evidence for action upon the DBD domain. Possible interactions between the compounds and other domains of the AR are not excluded, but the fact that the transcriptional activity of splice variants could be affected (data not shown) strongly argues for some preference toward the DBD. Notably, 14449 displayed inhibition of Y594D and Q592D mutants at ≥25 µM concentration (data not shown), suggesting that either the mutations shift the binding equilibrium of the compound or indeed that 14449 is able to engage the LBD or NTD domains as secondary targets.

The inhibitory effect of 14228/14449 was weaker against the splice variants when compared with the full-length AR. A maximum of 70-90% inhibition for transiently expressed V7 (data not shown) and 50-70% for endogenously produced V567es (data not shown) could be achieved. These levels of inhibition are similar to that of EPI-001, which could achieve ~80% inhibition of the AR(1-653) truncation mutant, lacking the LBD, when tested at 25 µM concentration on PC3 cells co-transfected with ARR$_3$tk-luciferase reporter (Andersen, R. J. et al. (2010) Regression of castrate-recurrent prostate cancer by a small-molecule inhibitor of the amino-terminus domain of the androgen receptor. *Cancer Cell* 17, 535-546).

We demonstrate a dramatic difference between the nuclear localization profile of YFP-AR in the presence of a known antiandrogen (enzalutamide) and 14228/14449 (data not shown). Although unimpeded nuclear localization does not strictly rule out 14228/14449 action upon the LBD, it clearly illustrates a different mechanism than enzalutamide activity, which promoted significant retention of the YFP-AR in the cytosol, likely by displacing R1881 and altering the AR protein structure (Watson, P. A. et al. (2010) Constitutively active androgen receptor splice variants expressed in castration-resistant prostate cancer require full-length androgen receptor. *Proc. Natl. Acad. Sci. U.S.A.* 107, 16759-16765; and Tran, C. et al. (2009) Development of a second-generation antiandrogen for treatment of advanced prostate cancer. *Science* 324, 787-790). It also suggests that 14228/14449 action must occur in the nucleus, a requirement to disrupt protein-DNA interactions. The fact that YFP-V7 completely localized to the nucleus in the presence or absence of drugs (data not shown) also agrees with a previous report indicating that enzalutamide could not cause AR-V7 to re-enter the cytosol (Watson, P. A. et al. (2010) Constitutively active androgen receptor splice variants expressed in castration-resistant prostate cancer require full-length androgen receptor. *Proc. Natl. Acad. Sci. U.S.A.* 107, 16759-16765).

The observed nuclear localization dynamics agree with the ability of the compounds to affect AR binding to chromatin or to alter association of dsDNA with the purified AR-DBD (data not shown). 14228/14449 may not totally abolish DNA binding, but rather weakens or modulates the binding in such a way as to prevent transcriptional activation by nuclear AR. Clarifying the exact mode of interference of AR binding to androgen-response elements by 14228/14449 will be an important area of investigation.

17. In Vivo Xenograft Assay

Figure 8:
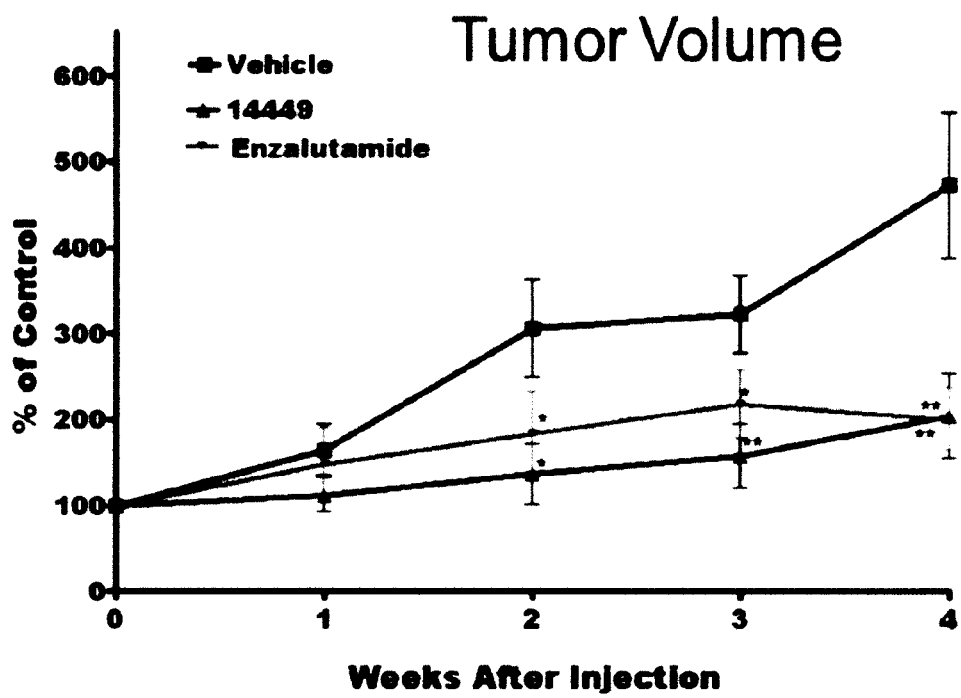
FIG. 8 shows that compound-14449 reduces tumor volume and abolishes PSA production in a LNCaP xenograft modelof castrated mice which were dosed twice daily with 14449 (100 mg/kg) or enzalutamide (Enz) (10 mg/kg) for 4 weeks and assessed for LNCaP xenograft tumor volume (A) and serum PSA (B), wherein the data are presented as mean±S.E., n=4. p value<0.05 was considered significant (*) compared with vehicle control; p value<0.001 was considered extremelysignificant (**) compared with vehicle control.
Figure 8:
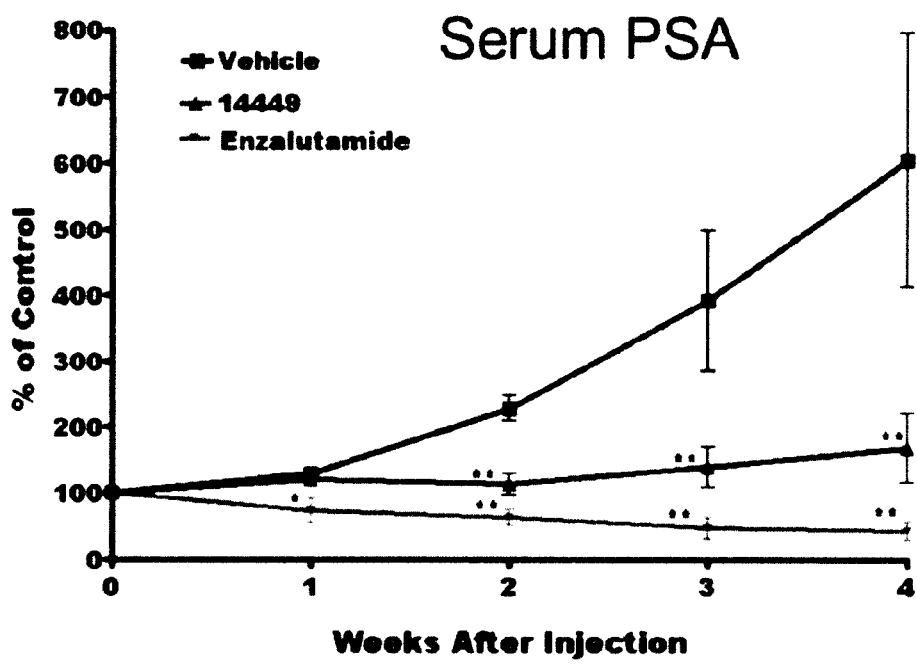

Finally, we showed that compound 14449 has favorable therapeutic characteristics in vivo (FIG. 8). In addition to having no observable toxic effect on animals, both tumor volume and PSA expression were inhibited to levels comparable with enzalutamide treatment. Thus, targeting DNA binding by the AR can be as effective in vivo as preventing nuclear translocation by enzalutamide (Tran, C. et al. (2009) Development of a second-generation antiandrogen for treatment of advanced prostate cancer. *Science* 324, 787-790) or by blocking co-factor recruitment at the AR-NTD by EPI-001 (Andersen, R. J. et al. (2010) Regression of castrate-recurrent prostate cancer by a small-molecule inhibitor of the amino-terminus domain of the androgen receptor. *Cancer Cell* 17, 535-546). The ability for 14449 to affect tumor xenografts from a variety of other cell lines, both androgen-sensitive and -independent, is currently underway. Recently, the compound pyrvinium pamoate (14337) was reported to inhibit the transcriptional activity of full length/splice variant ARs (Lim, M. et al. (2014) Ligand-independent and tissue-selective androgen receptor inhibition by pyrvinium. *ACS Chem. Biol.* 9, 692-702). Modeling of the AR-DBD-DNA interface (Protein Data Bank code 1R4I) was used to rationalize that pyrvinium interacts with the same surface-exposed pocket that is proposed here but in the conserved area of Lys-610 to Pro-613 possibly explaining the cross-reactivity of this compound with ER and GR (Lim, M. et al. (2014) Ligand-independent and tissue-selective androgen receptor inhibition by pyrvinium. *ACS Chem. Biol.* 9, 692-702). Direct evidence for an interaction with this pocket was not given, but replacing the DBD on the full-length AR with the LexA protein prevented drug inhibition, suggesting that pyrvinium binds somewhere on the DBD (Lim, M. et al. (2014) Ligand-independent and tissue-selective androgen receptor inhibition by pyrvinium. *ACS Chem. Biol.* 9, 692-702). Here, we revealed the general toxicity of pyrvinium (data not shown) and the inability to inhibit the AR bearing the Q592D and Y594D mutations. Although pyrvinium strongly inhibits the androgen signaling pathway, its cross-reactivity with other nuclear receptors and disruption of Wnt/β-cat signaling by binding at nanomolar concentrations to casein kinase family members (Thorne, C. A. et al. (2010) Small-molecule inhibition of Wnt signaling through activation of casein kinase 1α. *Nat. Chem. Biol.* 6, 829-836) makes the suitability for specific AR inhibition unclear, at least until less promiscuous derivatives of the compound are developed.

The identification of specific AR-DBD inhibitors with activity toward AR splice variants has excellent potential for treatment of enzalutamide-resistant or AR-variant driven castration-resistant PCa.

The following example (i.e. 18) is set out in more detail Li, H. et al. (2014) Discovery of small-molecule inhibitors selectively targeting the DNA-binding domain of the human androgen receptor. *J. Med. Chem.* 10.1021/jm500802j.

18. AR Inhibitory Activity, PSA Suppression and Anti-Proliferative Activity of 14449

A synthetic analogue 25 (i.e. 14449), bearing 4, 5-dibromoimidazole, displayed 2-fold improved activities (eGFP IC50=0.12±0.01 µM; PSA IC50=0.17 µM, FIGS. 9A and B) compared to compound 6 (i.e. 14228), reaching the level of activity of the latest FDA approved PCa drug, Enzalutamide (eGFP IC50=0.11±0.01 µM; PSA IC50=0.12 µM). In addition, compound 25 (i.e. 14449) and other halogen-containing analogues (Estebanez-Perpina, E. et al. A surface on the androgen receptor that allosterically regulates coactivator binding. Proc. Natl. Acad. Sci. U.S.A. 2007, 104, 16074-

Figure 9:
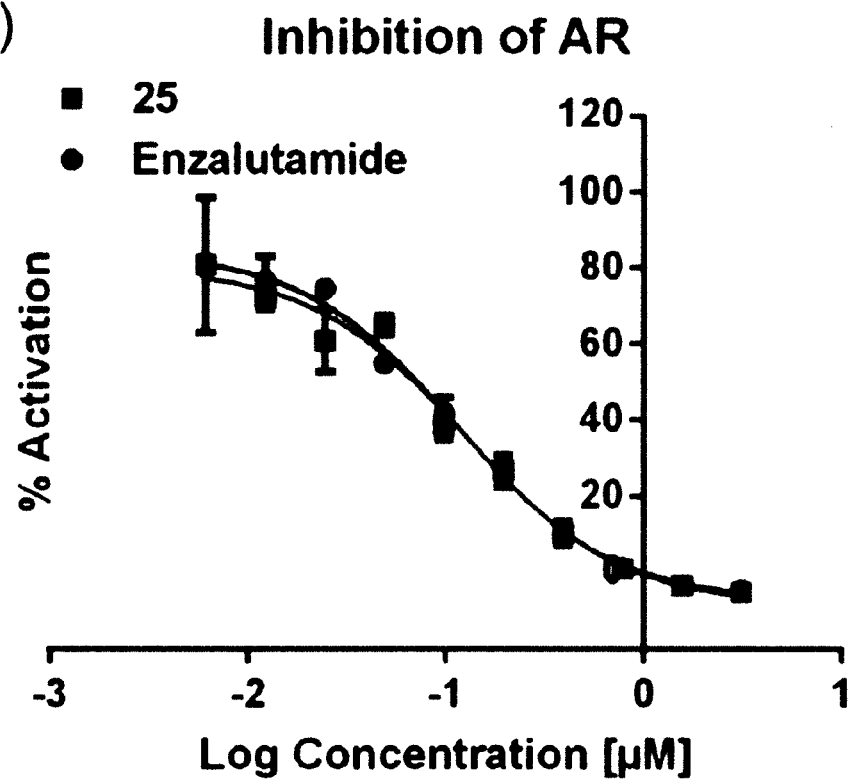
FIG. 9 shows a series of plots, (A) AR inhibitory activity of compound 25 (i.e. 14449) is compared to Enzalutamide using LNCaP eGFP cells in the presence of 0.1 nM R1881 by measuring the fluorescence; (B) PSA suppression by these compounds was evaluated by measuring the PSA secreted into the media using the same LNCaP eGFP cells; and (C) antiproliferative effect of 25 (i.e. 14449) on LNCaP, MR49F (Enzalutamide-resistant) and PC3 cells using MTS assay, wherein the LNCaP, MR49F, and PC3 cells were treated with the inhibitor at various concentrations for 3 days in the presence of 0.1 nM R1881.
Figure 9:
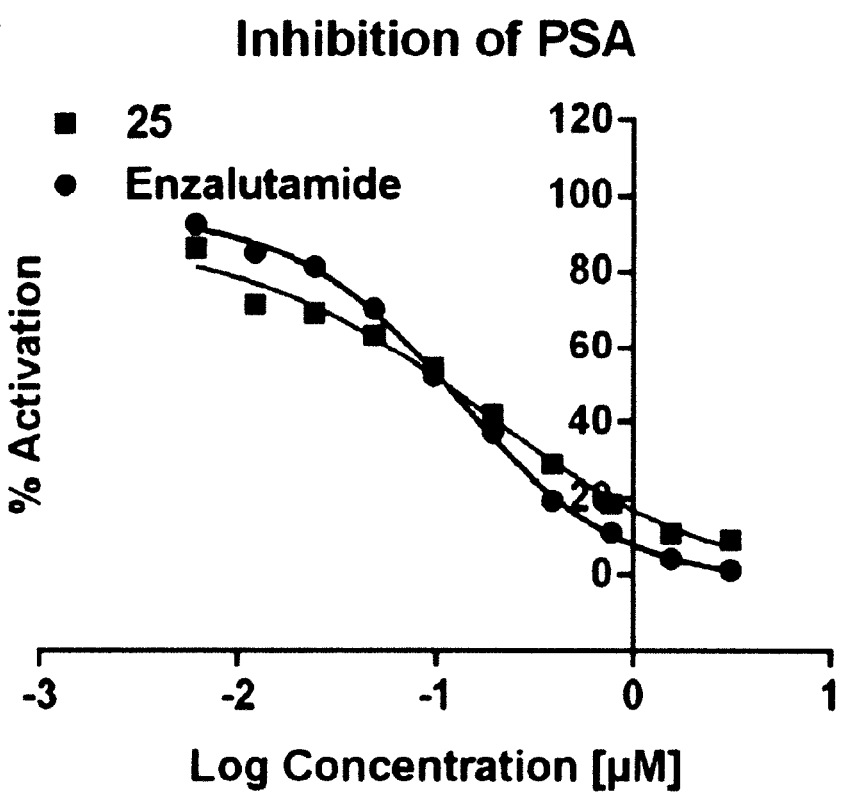
Figure 9:
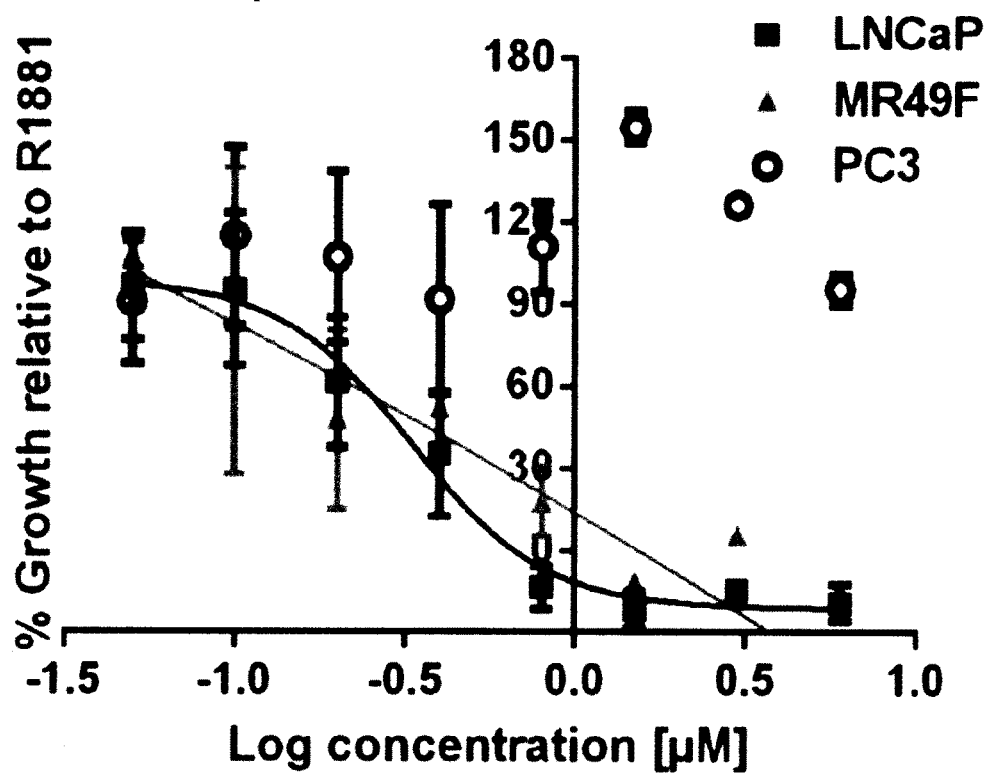

16079; and Li, H. et al. Identification of novel androgen receptor antagonists using structure- and ligand-based methods. J. Chem. Inf. Model. 2013, 53, 123-130.) are fully stable in media. With such promising inhibitory activity toward AR transcription and PSA expression, we further evaluated the ability of 25 to inhibit the growth of AR-dependent PCa cells in the AR-positive LNCaP system. Following hormone activation of the AR (0.1 nM R1881), compound 25 (i.e. 14449) elicited a concentration-dependent inhibition of the cell growth. A similar potency for cell-growth inhibition was achieved when 25 (i.e. 14449) was evaluated against the newly developed Enzalutamide-resistant cell line, MR49F (Kuruma, H. et al. A novel antiandrogen, Compound 30, suppresses castration resistant and MDV3100-resistant prostate cancer growth in vitro and in vivo. Mol. Cancer Ther. 2013, 12, 567-576). Importantly, compound 25 (i.e. 14449) is ineffective in inhibiting the proliferation of AR-negative PC3 cells, supporting the mechanism of its action through specific interaction with the AR rather than by means of generic toxicity (FIG. 9C).

Furthermore, a site-directed mutagenesis study of the predicted binding site residues indicates showed that compounds 14228 and 14449 bind directly to the site. Wildtype hAR and hAR mutant plasmids (S579D, V582D, F583D, R586D, Q592D, Y594D, and K610D) were transfected with a ARR$_3$tk luciferase reporter into PC3 cells, and the transcriptional activities of tested compounds 14228, 14449 and Enzalutamide at 10 μM were measured based on the luminescence. Compounds 14228 and 14449 were shown to inhibit the transcription of AR-V7 in a concentration-dependent manner. Wildtype hAR/ARV7 plasmids were co-transfected into PC3 cells with the ARR3tk-luciferase reporter and treated with compound 14228, 14449 and Enzalutamide.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to an embodiment of the present invention. Any priority document(s) and all publications, including but not limited to patents and patent applications, cited in this specification are incorporated herein by reference as if each individual publication were specifically and individually indicated to be incorporated by reference herein and as though fully set forth herein. The invention includes all embodiments and variations substantially as hereinbefore described and with reference to the examples and drawings.

What is claimed is:
1. A method for treating prostate cancer, the method comprising administering to a subject in need thereof, a therapeutically effective amount of a compound having the formula,

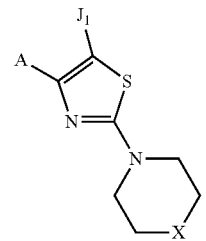

wherein
J$_1$ is selected from the group consisting of H, CH$_2$CH$_3$, CH$_3$, Cl, Br, I, F, COOH, and OH,
A is selected from the group consisting of:

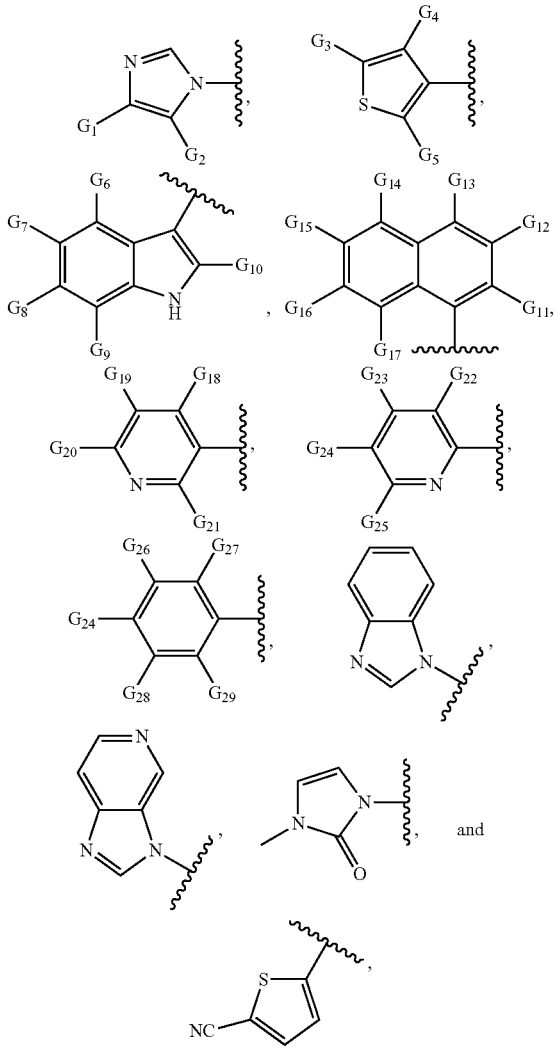

wherein
G$_1$ and G$_2$ are independently Br, Cl, I, CH$_3$, H, F or OH, provided that G$_1$ and G$_2$ are not both Br, Cl, I, or H;
G$_3$ is Cl, H, CH$_3$, Br, I, F or OH;
G$_4$ is Cl, H, Br, I, F or OH, or G$_4$ is CH$_3$ provided that both G$_3$ and G$_5$ are not both H;
G$_5$-G$_{10}$ are independently selected from H, CH$_2$OH, Cl, Br, I, F and OH;

$G_{11}$-$G_{17}$ are independently selected from H, $CH_2OH$, Cl, Br, I, F and OH;
$G_{18}$-$G_{21}$ are independently selected from H, $CH_2OH$, Cl, Br, I, F and OH;
$G_{22}$-$G_{25}$ are independently selected from H, $CH_2OH$, Cl, Br, I, F and OH;
$G_{26}$-$G_{29}$ are independently selected from H, $CH_2OH$, Cl, Br, I, F and OH; and
X is O, S, or $CH_2$.

2. The method of claim 1, wherein $J_1$ is H.

3. The method of claim 1, wherein the compound has the formula,

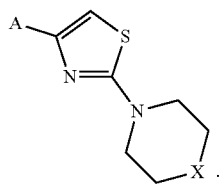

4. The method of claim 3, wherein X is O or S.

5. The method of claim 3, wherein A is selected from

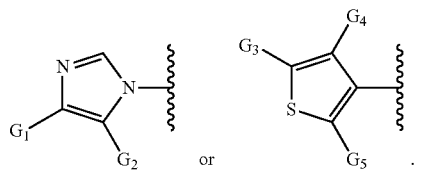

6. A method for treating prostate cancer, the method comprising administering to a subject in need thereof, a therapeutically effective amount of a compound having the formula,

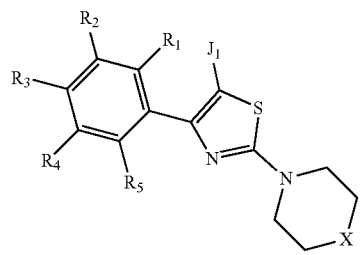

wherein
$J_1$ is H, $CH_2CH_3$, $CH_3$, Cl, Br, I, F, COOH, or OH, provided that when $J_1$ is $CH_3$, $R_1$ is not OH;
$R_1$ is H, $OCH_3$, OH, $CH_3$, $NH_2$, Cl, $SO_2CH_3$, $OCH(CH_3)_2$, $O(CH_2)_2OCH_3$, Br, I, CN, $CH_2OH$, $CH_2CH_3$, $OCH_2CH_3$, $NHCH_3$, CN, or $CF_3$;
$R_2$ is H, $CF_3$, OH, $CH_3$, CN, $NH_2$, $CH_2OH$, $SO_2CH_3$, $OCH(CH_3)_2$, $O(CH_2)_2OCH_3$, $CH_2CH_3$, or $OCH_2CH_3$; or
$R_2$ is selected from F, Cl, Br and I, provided that $R_1$ is not one of Cl F, Br or I;
$R_3$ is H, F, CN, Cl, OH, $SCH_3$, $OCH_3$, $O(CH_2)_2OCH_3$, $CH_3$, $NH_2$, $SO_2CH_3$, $OCH(CH_3)_2$, $NHCH_3$, Br, I, $CH_2OH$, $CH_2CH_3$, $OCH_2CH_3$, or $CF_3$;
$R_4$ is H, $CH_3$, $NHCH_3$, OH, $CH_2OH$, F, CN, Cl, $SCH_3$, $OCH_3$, $O(CH_2)_2OCH_3$, $NH_2$, $SO_2CH_3$, $OCH(CH_3)_2$, $NHCH_3$, Br, I, $CH_2CH_3$, $OCH_2CH_3$, or $CF_3$;
$R_5$ is H, $CH_3$, $NHCH_3$, OH, $CH_2OH$, F, CN, Cl, $SCH_3$, $OCH_3$, $O(CH_2)_2OCH_3$, $NH_2$, $SO_2CH_3$, $OCH(CH_3)_2$, $NHCH_3$, Br, I, $CH_2CH_3$, $OCH_2CH_3$, or $CF_3$;
X is O, S, or $CH_2$;
provided that the compound is not one of the following:

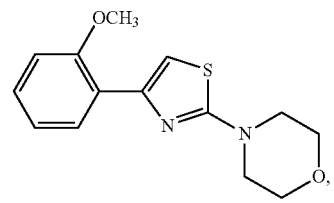

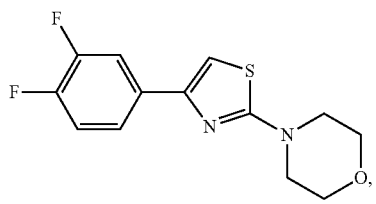

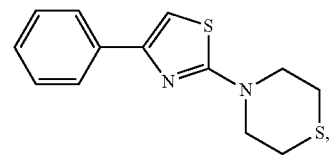

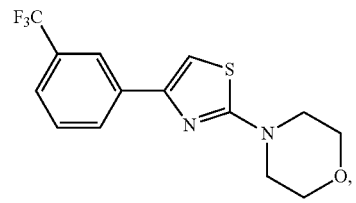

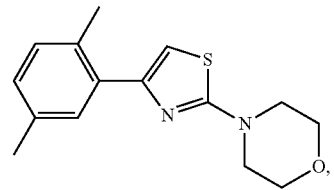

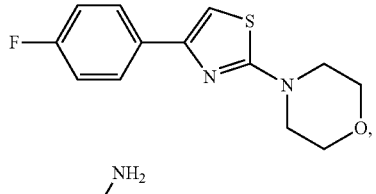

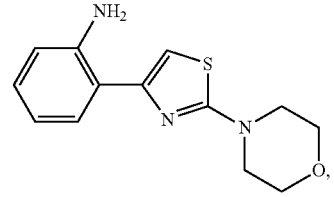

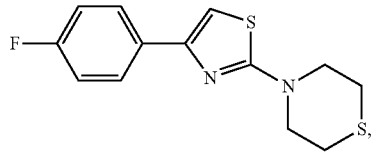

-continued
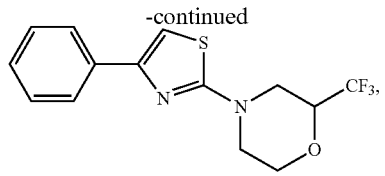
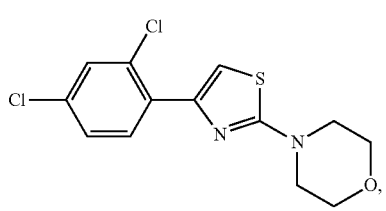
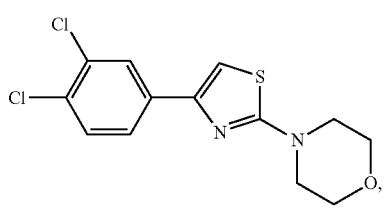
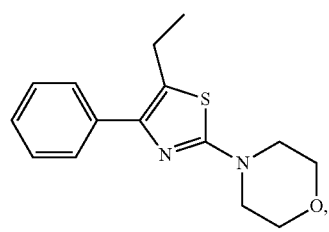
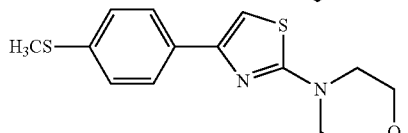
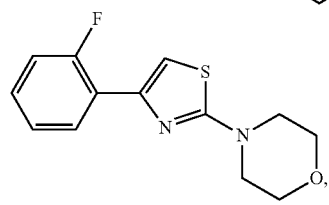
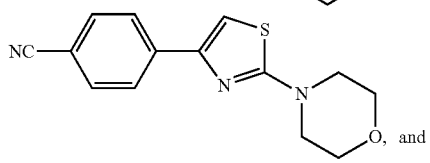, and
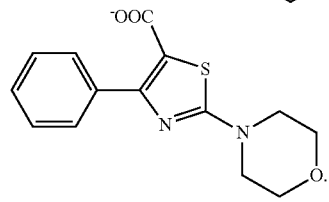.
7. The method of claim 6, wherein the compound is selected from the group consisting of:
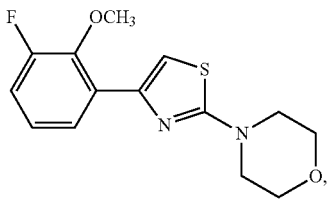
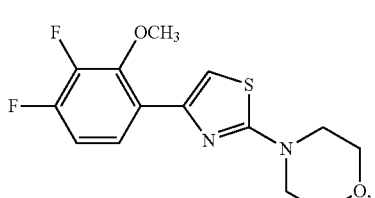
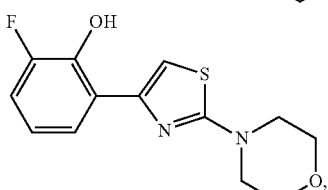
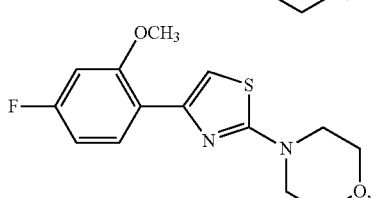
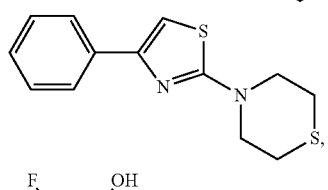
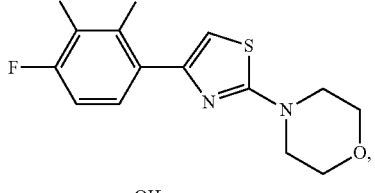
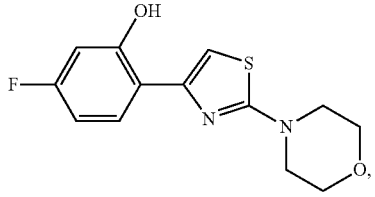
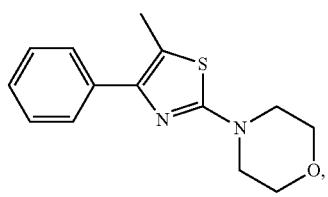

-continued
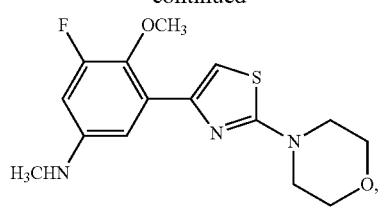
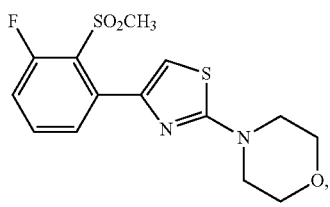
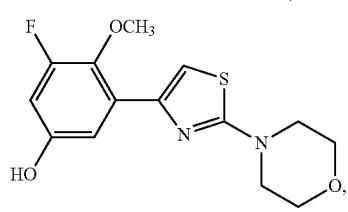
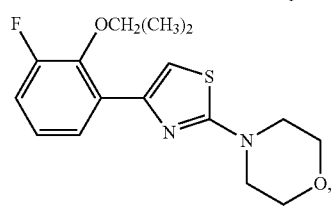
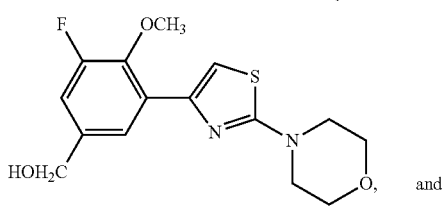
and
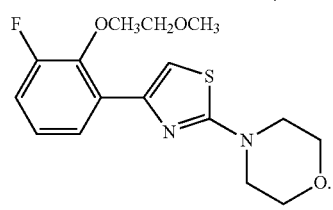
8. The method of claim 1, wherein the compound is selected from the group consisting of:
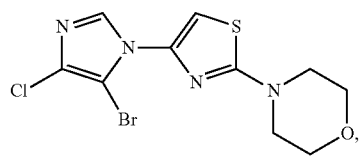
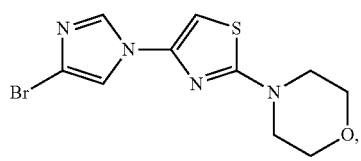
-continued
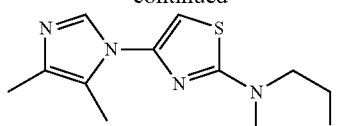
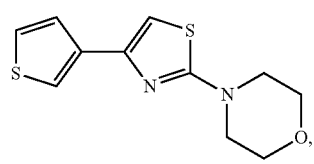
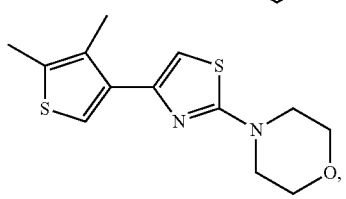
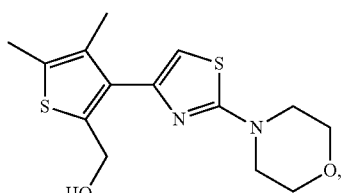
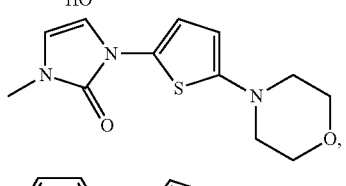
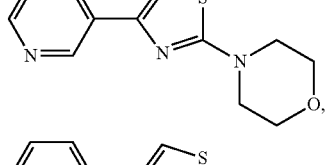
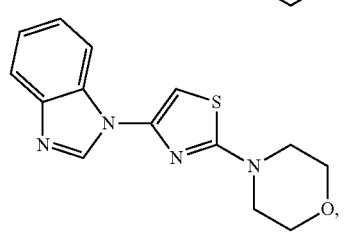

-continued

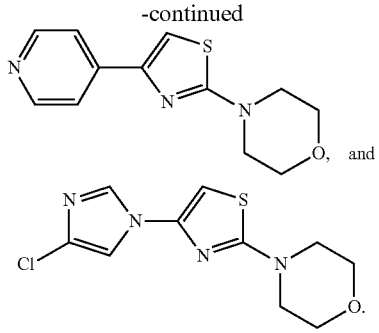
and

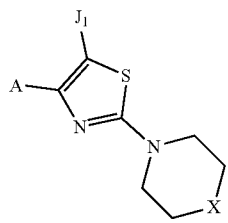

9. A pharmaceutical composition comprising a pharmaceutically acceptable carrier and a compound having the formula,

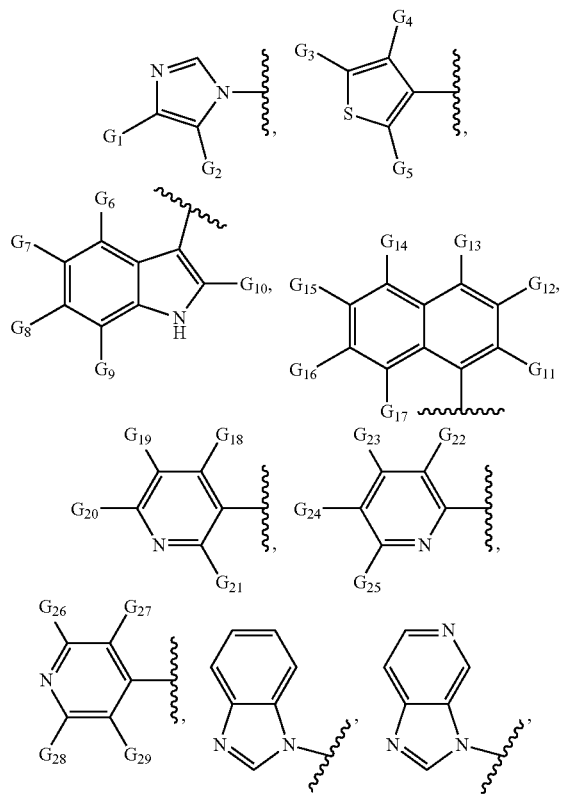

wherein $J_1$ is selected from the group consisting of H, $CH_2CH_3$, $CH_3$, Cl, Br, I, F, COOH, and OH, A is selected from the group consisting of:

-continued

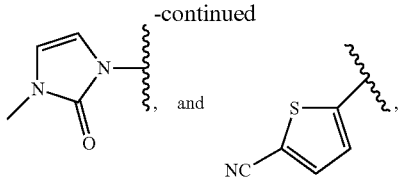
and wherein
- $G_1$ and $G_2$ are independently Br, Cl, I, $CH_3$, H, F or OH, provided that $G_1$ and $G_2$ are not both Br, Cl, I, or H;
- $G_3$ is Cl, H, $CH_3$, Br, I, F or OH;
- $G_4$ is Cl, H, Br, I, F or OH, or $G_4$ is $CH_3$ provided that both $G_3$ and $G_5$ are not both H;
- $G_5$-$G_{10}$ are independently selected from H, $CH_2OH$, Cl, Br, I, F and OH;
- $G_{11}$-$G_{17}$ are independently selected from H, $CH_2OH$, Cl, Br, I, F and OH;
- $G_{18}$-$G_{21}$ are independently selected from H, $CH_2OH$, Cl, Br, I, F and OH;
- $G_{22}$-$G_{25}$ are independently selected from H, $CH_2OH$, Cl, Br, I, F and OH;
- $G_{26}$-$G_{29}$ are independently selected from H, $CH_2OH$, Cl, Br, I, F and OH; and
- X is O, S, or $CH_2$.

10. A commercial package comprising instructions for use in treatment of prostate cancer and a compound having the formula,

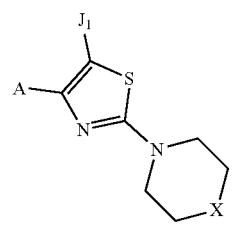

wherein $J_1$ is selected from the group consisting of H, $CH_2CH_3$, $CH_3$, Cl, Br, I, F, COOH, and OH, A is selected from the group consisting of:

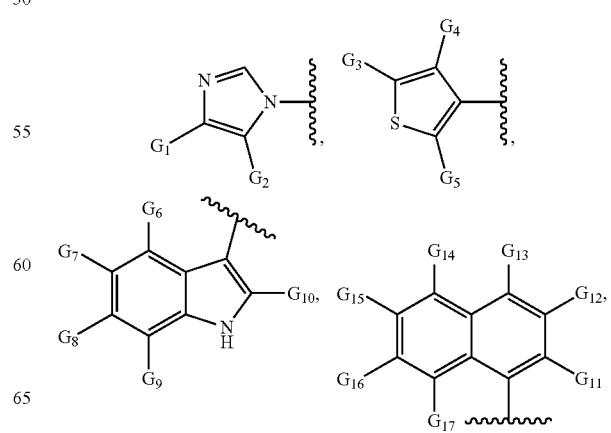

-continued

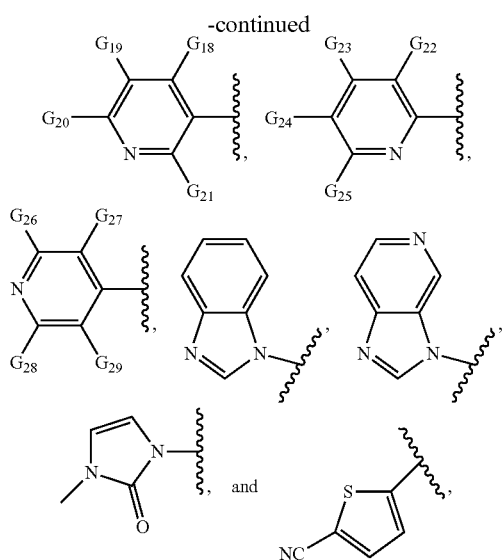

wherein
G₁ and G₂ are independently Br, Cl, I, CH₃, H, F or OH, provided that G₁ and G₂ are not both Br, Cl, I, or H;
G₃ is Cl, H, CH₃, Br, I, F or OH;
G₄ is Cl, H, Br, I, F or OH, or G₄ is CH₃ provided that both G₃ and G₅ are not both H;
G₅-G₁₀ are independently selected from H, CH₂OH, Cl, Br, I, F and OH;
G₁₁-G₁₇ are independently selected from H, CH₂OH, Cl, Br, I, F and OH;
G₁₈-G₂₁ are independently selected from H, CH₂OH, Cl, Br, I, F and OH;
G₂₂-G₂₅ are independently selected from H, CH₂OH, Cl, Br, I, F and OH;
G₂₆-G₂₉ are independently selected from H, CH₂OH, Cl, Br, I, F and OH; and
X is O, S, or CH₂.

11. A compound having the formula:

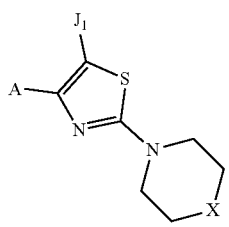

wherein
J₁ is selected from the group consisting of H, CH₂CH₃, CH₃, and F;
A is selected from the group consisting of:

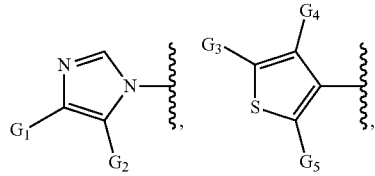

-continued

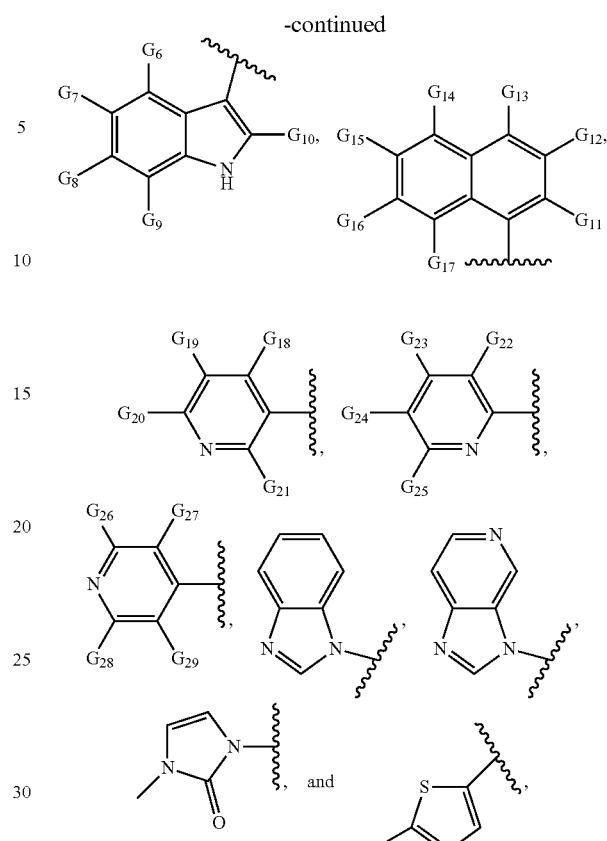

wherein
G₁ and G₂ are independently Br, Cl, I, CH₃, H, F, or OH, provided that G₁ and G₂ are not both Br, Cl, I, or H;
G₃ is Cl, H, CH₃, Br, I, F, or OH, provided that G₃ and G₅ are not both Cl;
G₄ is Cl, H, Br, I, F, or OH;
G₅-G₁₀ are independently selected from H, CH₂OH, Cl, Br, I, F, and OH;
G₁₁-G₁₇ are independently selected from H, CH₂OH, Cl, Br, I, F and OH;
G₁₈-G₂₁ are independently selected from H, CH₂OH, Cl, Br, I, F and OH;
G₂₂-G₂₅ are independently selected from H, CH₂OH, Cl, Br, I, F and OH;
G₂₆-G₂₉ are independently selected from H, CH₂OH, Cl, Br, I, F, and OH; and
X is O, S, or CH.

12. The compound of claim 11, wherein J is H.
13. The compound of claim 11, wherein A is selected from

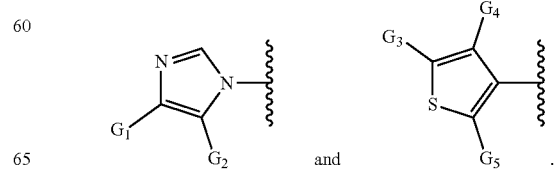

14. The compound of claim 11, wherein the compound is selected from the group consisting of:
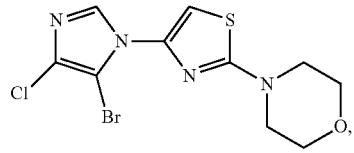
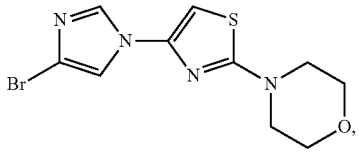
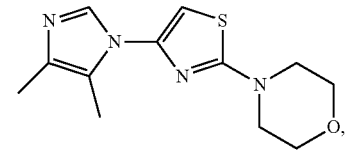
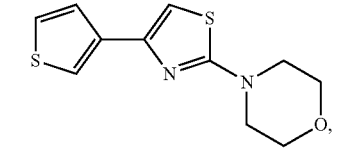
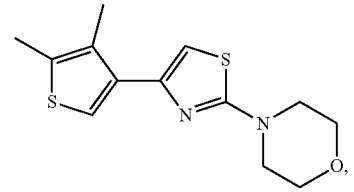
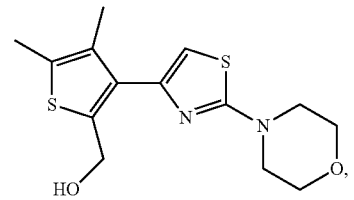
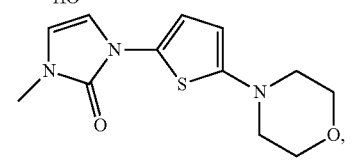
-continued
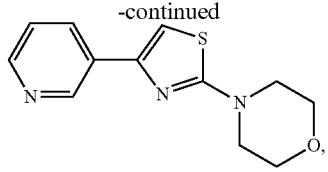
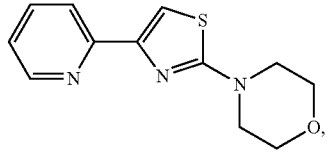
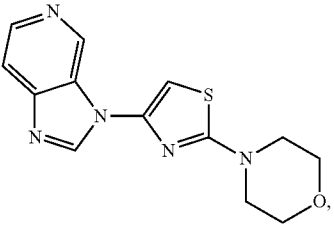
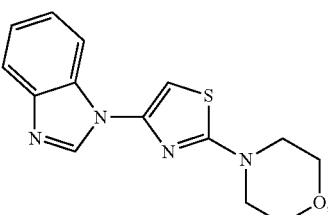
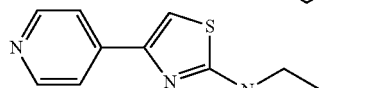
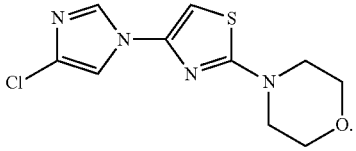
15. A pharmaceutical composition comprising a compound of claim 11 and a pharmaceutically acceptable carrier.
16. A commercial package comprising a therapeutically effective amount of a compound of claim 11 and instructions for use in treatment of prostate cancer.
* * * * *